(12) United States Patent
Fischer

(10) Patent No.: US 11,213,378 B2
(45) Date of Patent: Jan. 4, 2022

(54) SYSTEMS AND METHODS FOR MESH AUGMENTATION AND PREVENTION OF INCISIONAL HERNIA

(71) Applicant: THE TRUSTEES OF THE UNIVERSITY OF PENNSYLVANIA, Philadelphia, PA (US)

(72) Inventor: John Patrick Fischer, Philadelphia, PA (US)

(73) Assignee: THE TRUSTEES OF THE UNIVERSITY OF PENNSYLVANIA, Philadelphia, PA (US)

(*) Notice: Subject to any disclaimer, the term of this patent is extended or adjusted under 35 U.S.C. 154(b) by 124 days.

(21) Appl. No.: 16/151,926

(22) Filed: Oct. 4, 2018

(65) Prior Publication Data

US 2019/0029788 A1    Jan. 31, 2019

Related U.S. Application Data

(63) Continuation of application No. 15/076,204, filed on Mar. 21, 2016, now Pat. No. 10,136,984, which is a
(Continued)

(51) Int. Cl.
*A61F 2/00* (2006.01)
*A61B 17/068* (2006.01)
(Continued)

(52) U.S. Cl.
CPC ...... *A61F 2/0063* (2013.01); *A61B 17/00491* (2013.01); *A61B 17/064* (2013.01);
(Continued)

(58) Field of Classification Search
CPC ............ A61F 2/0063; A61F 2/0095; A61F 2220/0016; A61B 50/33; A61B 50/15;
(Continued)

(56) References Cited

U.S. PATENT DOCUMENTS

| 5,544,664 A | 8/1996 | Benderev et al. |
| 5,830,221 A | 11/1998 | Stein et al. |

(Continued)

FOREIGN PATENT DOCUMENTS

| EP | 1 595 504 A1 | 11/2005 |
| WO | WO 2007/059199 A2 | 5/2007 |
| WO | WO 2010/009327 A1 | 9/2010 |

OTHER PUBLICATIONS

U.S. Appl. No. 15/076,204 (US 2017/0319319), filed Mar. 21, 2016 (Nov. 9, 2017).
(Continued)

*Primary Examiner* — Erich G Herbermann
(74) *Attorney, Agent, or Firm* — Baker Botts L.L.P.

(57) ABSTRACT

Techniques for mesh augmentation and prevention of incisional hernia, including systems and methods for affixing mesh to a fascial incision. A mesh strip can be integrated with one or more uni-directional fasteners. Each fastener can include an anchoring mechanism adapted for affixation to anterior abdominal wall fascia and a mating interface. An applicator can include tension arms adapted to interface with the mating interfaces of the fasteners to maintain a vertical tension of the mesh strip and a handle coupled with the tension arms adapted to spread the tension arms and thereby control a horizontal tension of the mesh strip. The mesh strip can be configured to be aligned over a fascial incision using the applicator and affixed under tension to anterior abdominal wall fascia by tissue penetration of the anchoring mechanisms of the one or more fasteners.

21 Claims, 48 Drawing Sheets

Related U.S. Application Data continuation of application No. PCT/US2016/020685, filed on Mar. 3, 2016.

(60) Provisional application No. 62/127,470, filed on Mar. 3, 2015, provisional application No. 62/232,098, filed on Sep. 24, 2015.

(51) Int. Cl.
  *A61B 17/064* (2006.01)
  *A61B 50/33* (2016.01)
  *A61B 17/00* (2006.01)
  *A61B 50/15* (2016.01)

(52) U.S. Cl.
  CPC ............ *A61B 17/068* (2013.01); *A61B 50/33* (2016.02); *A61F 2/0095* (2013.01); *A61B 50/15* (2016.02); *A61B 2017/00398* (2013.01); *A61B 2017/00424* (2013.01); *A61B 2017/00477* (2013.01); *A61B 2017/0641* (2013.01); *A61B 2017/0647* (2013.01); *A61B 2017/0688* (2013.01); *A61F 2002/0072* (2013.01); *A61F 2220/0016* (2013.01)

(58) Field of Classification Search
  CPC ............ A61B 17/00491; A61B 17/064; A61B 17/068; A61B 2017/00398; A61B 2017/00424; A61B 2017/00477; A61B 2017/0641; A61B 2017/0647; A61B 2017/0688; A61B 2002/0072
  See application file for complete search history.

(56) References Cited

U.S. PATENT DOCUMENTS

| | | | |
|---|---|---|---|
| 6,334,446 B1 | 1/2002 | Beyar | |
| 6,387,041 B1 | 5/2002 | Harari et al. | |
| 2004/0176785 A1 | 9/2004 | Hermann et al. | |
| 2005/0049638 A1 | 3/2005 | Mandelbaum | |
| 2005/0288691 A1* | 12/2005 | Leiboff | A61F 2/0063 606/151 |
| 2007/0038220 A1 | 2/2007 | Shipp | |
| 2007/0185506 A1 | 8/2007 | Jackson | |
| 2008/0167520 A1 | 7/2008 | Benderev | |
| 2008/0188874 A1 | 8/2008 | Henderson | |
| 2009/0204130 A1 | 8/2009 | Kantsevoy et al. | |
| 2009/0216264 A1* | 8/2009 | Friedman | A61B 17/0057 606/213 |
| 2009/0324720 A1* | 12/2009 | He | A61L 31/145 424/484 |
| 2010/0312357 A1 | 12/2010 | Levin et al. | |
| 2011/0040311 A1* | 2/2011 | Levin | A61B 17/0469 606/151 |
| 2011/0054500 A1* | 3/2011 | Levin | A61B 17/068 606/151 |
| 2012/0149976 A1 | 6/2012 | Wirbisky et al. | |
| 2012/0184805 A1* | 7/2012 | Pulliam | A61L 31/16 600/37 |
| 2012/0209401 A1 | 8/2012 | Euteneuer et al. | |
| 2013/0018395 A1 | 1/2013 | Friedlander et al. | |
| 2014/0379007 A1* | 12/2014 | Soares Da Costa | A61F 2/0063 606/151 |
| 2016/0120631 A1 | 5/2016 | Murphy | |
| 2017/0172551 A1 | 6/2017 | Rao | |

OTHER PUBLICATIONS

U.S. Appl. No. 15/076,204, filed Oct. 25, 2018 Issue Fee Payment.
U.S. Appl. No. 15/076,204, filed Sep. 24, 2018 Notice of Allowance.
U.S. Appl. No. 15/076,204, filed Aug. 2, 2018 Response to Non-Final Office Action.
U.S. Appl. No. 15/076,204, filed Jul. 20, 2018 Applicant Initiated Interview Summary.
U.S. Appl. No. 15/076,204, filed May 3, 2018 Non-Final Office Action.
U.S. Appl. No. 15/076,204, filed Apr. 11, 2018 Applicant Initiated Interview Summary.
U.S. Appl. No. 15/076,204, filed Apr. 10, 2018 Amendment and Request for Continued Examination (RCE).
U.S. Appl. No. 15/076,204, filed Feb. 23, 2018 Final Office Action.
U.S. Appl. No. 15/076,204, filed Dec. 18, 2017 Response to Non-Final Office Action.
U.S. Appl. No. 15/076,204, filed Nov. 24, 2017 Non-Final Office Action.
U.S. Appl. No. 15/076,204, filed Nov. 6, 2017 Response to Restriction Requirement.
U.S. Appl. No. 15/076,204, filed Sep. 29, 2017 Restriction Requirement.
International Search Report and Written Opinion dated Jul. 26, 2016 in International Application No. PCT/U52016/02685.
Supplementary Partial European Search Report dated Oct. 18, 2018 in EP Application No. 16759493.
U.S. Appl. No. 16/119,276 (US 2019/0059871), filed Aug. 31, 2018 (Feb. 28, 2019).
U.S. Appl. No. 16/119,276, filed Mar. 4, 2019 Non-Final Office Action.
U.S. Appl. No. 16/119,276, filed Mar. 22, 2019 Response to Non-Final Office Action.
U.S. Appl. No. 16/119,276, filed Jun. 20, 2019 Final Office Action.
U.S. Appl. No. 16/119,276, filed Jul. 11, 2019 Amendment and Request for Continued Examination (RCE).
U.S. Appl. No. 16/119,276, filed Jul. 16, 2019 Applicant Initiated Interview Summary.
U.S. Appl. No. 16/119,276, filed Jul. 23, 2019 Adivisory Action.
U.S. Appl. No. 16/119,276, filed Aug. 9, 2019 Request for Continued Examination (RCE).
U.S. Appl. No. 16/119,276, filed Dec. 26, 2019 Non-Final Office Action.
U.S. Appl. No. 16/119,276, filed Feb. 27, 2020 Response to Non-Final Office Action.
U.S. Appl. No. 16/119,276, filed Apr. 22, 2020 Final Office Action.
U.S. Appl. No. 16/119,276, filed Jul. 13, 2020 Notice of Appeal Filed.

* cited by examiner

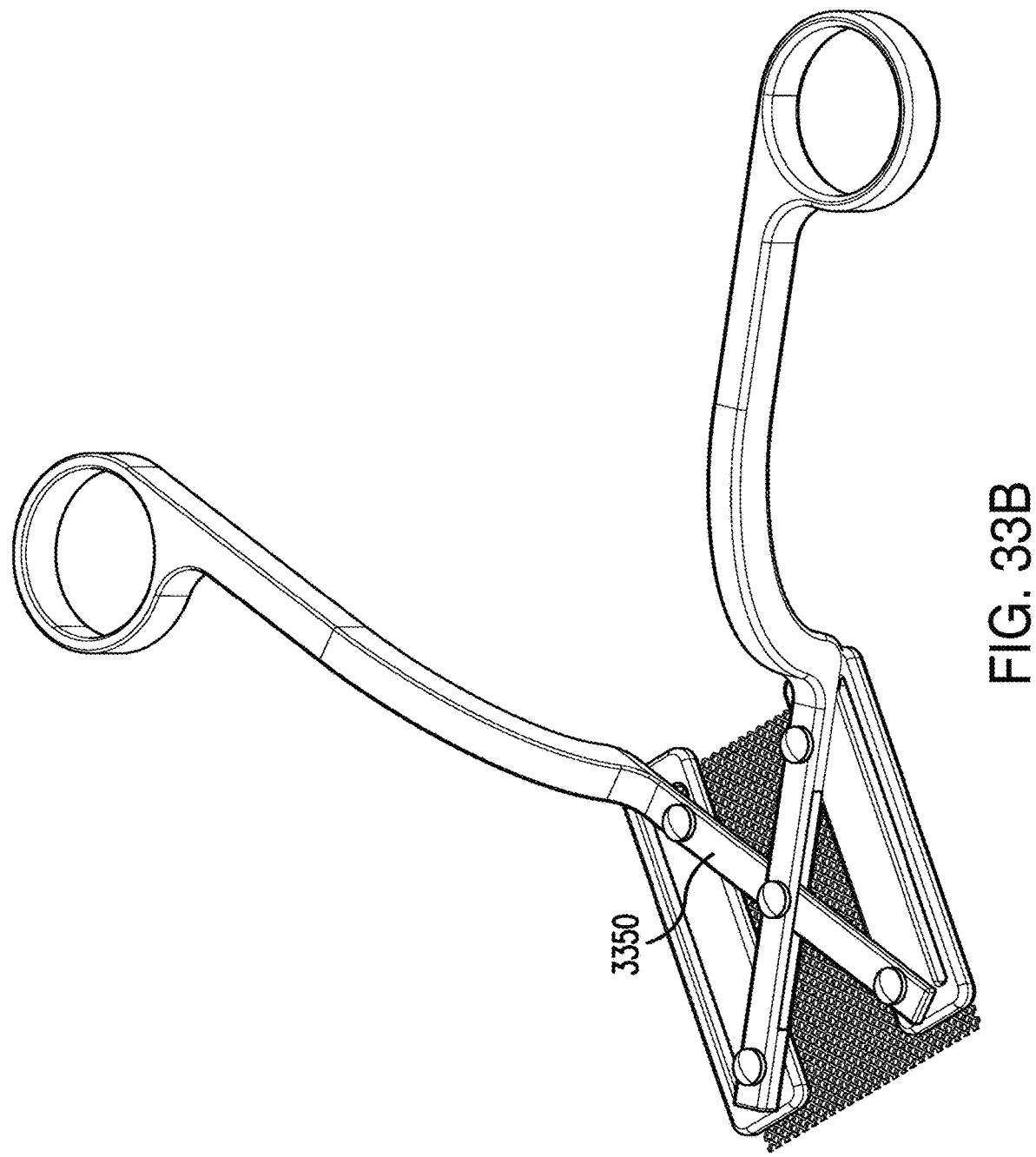

SYSTEMS AND METHODS FOR MESH AUGMENTATION AND PREVENTION OF INCISIONAL HERNIA

CROSS-REFERENCE TO RELATED APPLICATIONS

This application is a continuation of U.S. patent application Ser. No. 15/076,204, filed Mar. 21, 2016, which is a continuation of PCT Application No. PCT/US2016/020685 filed Mar. 3, 2016, which claims priority to U.S. Provisional Application No. 62/232,098, filed Sep. 24, 2015, and U.S. Provisional Application No. 62/127,470, filed Mar. 3, 2015, each of which are incorporated by reference herein in their entirety.

BACKGROUND

The disclosed subject matter relates generally to techniques and devices for spatially controlling and mechanically tensioning constructs for tissue reinforcement using integrated fastener-anchors, including techniques for reducing hernia risk following surgery via mesh onlay fixation to the abdominal wall fascia.

Incisional hernia (IH) is a protrusion of intra-abdominal contents, often intestines, through the abdominal wall, which can be the result of a failed or disrupted fascial closure after surgical incision through the abdominal fascia. The incidence of hernia can be approximately 13% and can be as high as 70% following incisions to the abdominal wall in certain high risk patient populations, and the cost burden for hernia is significant. Further, hernias can be debilitating for patients and associated with a significant decrease in quality of life.

IH are treated after they occur, typically and most effectively reinforced with mesh to reduce subsequent recurrence. However, even with certain available techniques, approximately 1 in 3 repaired hernias will recur, and with each failed repair the chance of success decreases and costs increases. The compounded challenge of failed repairs coupled with associated costs and morbidity, underscores the need for prevention.

One strategy to prevent IH is to use prophylactic mesh augmentation (PMA) at the index abdominal surgery procedure to reinforce the fascia of before herniation actually occurs. PMA can be implemented to reduce risk and morbidity, and contain cost in high risk patients undergoing abdominal fascial incisions. However, a simple, reliable, and precise mechanism and system to provide PMA is needed. Current challenges of widespread PMA adoption include the added operative, technical challenges related to mesh anchoring and fixation, variability in technique, and uncertain biomechanical benefit and mesh tensioning. Although suturing or fastening the mesh by hand can be effective, this can add operative time and may be subject to user technical ability. Person-to-person variability, added operative time, and biomechanical benefit are thus issues affecting adoption of this technique.

SUMMARY

The disclosed subject matter provides a mesh augmentation system that removes time-consuming hand-sewing of mesh through a simplified system utilizing pre-integrated mesh fastener-anchors.

In one aspect of the disclosed subject matter, systems for mesh augmentation are provided. In example embodiments, a system can include a mesh tension-applicator to engage with the mesh through a mating process with a uni-direction fastener. Following mating, the mesh can be spatially controlled and incrementally tensioned and precisely affixed to the anterior abdominal fascia or any other tissue construct. The disclosed subject matter can reduce technical intra-operative challenges of handling mesh and affixing it to the fascia that are encountered when hand-suturing.

In accordance with an exemplary embodiment, a system for affixing mesh to a fascial incision can include a mesh strip integrated with one or more pre-fabricated uni-directional fasteners, each fastener including an anchor adapted for affixation to anterior abdominal wall fascia and a mating interface. The system can include an applicator including tension arms adapted to interface with the mating components of the fasteners to maintain a vertical tension of the mesh strip and a handle coupled with the tension arms adapted to spread the tension arms and thereby control a horizontal tension of the mesh strip. The mesh strip can be aligned over a closed fascial incision using the applicator and the mesh strip can be affixed under tension to anterior abdominal wall fascia by tissue penetration of the anchors of the one or more fasteners.

In certain embodiments, the system can also include a tray or mechanism adapted to hold the mesh strip prior to interfacing with the applicator. The tray can include wells adapted to interface with the anchors of the one or more fasteners and support the mesh strip and fasteners during mating with the applicator. Trays can be stacked together and slid off when used intra-operatively. Additionally or alternatively, the applicator can include a tensiometer configured to measure and display the horizontal or vertical, incremental tension applied to the mesh strip. The applicator and its associated arms can also include a spring for out of plane affixation (e.g., where the fascia is uneven) of the fasteners and mesh strip to the fascia and/or an electro-mechanical actuator to affix the fasteners and the mesh strip to the fascia. In certain embodiments, the mating interfaces of the fasteners can include a post or a knob adapted to be received by a port of at least one of the tension arms, or a snap or a structural element having a hole therein adapted to receive at least one of the tension arms.

The disclosed subject matter also provides methods for affixing mesh to a fascial incision including aligning a mesh strip over a fascial incision using an applicator. The mesh strip can be integrated with one or more pre-fabricated uni-directional fasteners, each fastener including an anchor adapted for affixation to anterior abdominal wall fascia and a mating interface. The applicator can include tension arms adapted to interface with the mating interfaces of the fasteners to maintain a vertical tension of the mesh strip and a handle coupled with the tension arms adapted to spread the tension arms. An exemplary method can include controlling a horizontal tension of the mesh strip by using the handle to spread the tension arms and affixing the mesh strip under tension to anterior abdominal wall fascia by applying a force to the fasteners to thereby achieve tissue penetration of the anchors of the one or more fasteners. In certain embodiments, the force applied to the fasteners can be mediated mechanically or electro-mechanically through the applicator and by interfacing with the mating interface of each fastener and transduced into the mesh strip to allow pre-tensioned application into the fascia.

In accordance with another exemplary embodiment, a pre-fabricated mesh strip for affixation to a fascial incision can include a mesh strip and one or more uni-directional fasteners integrated with the mesh strip. Each fastener can include an anchor and a mating interface. Each anchor can be adapted for affixation to anterior abdominal wall fascia. Each mating interface can be adapted to interface with tension arms of an applicator to maintain a vertical tension of the mesh strip and control a horizontal tension of the mesh strip during affixation to anterior abdominal wall fascia.

In certain exemplary embodiments, the mesh strip can be formed from a permanent synthetic absorbable or non-absorbable mesh, a biologic mesh, or bio-absorbable mesh or a hybrid mesh formed from components of each. The mesh strip can be integrated with any number of uni-directional fasteners in various orientations and positions. In an exemplary embodiment, each fastener can be disposed at a corner of the mesh strip. The anchor of each fastener can include one or more barbed affixations adapted for a predetermined depth of fascia penetration. Each fastener can also include radial arms, each arm including a post for insertion into a hole of the mesh strip to thereby integrate the fastener with the mesh strip. In an exemplary embodiment the mesh may be anchored by the automated application of biologic or biomedical adhesive or glue, either discretely or in combination with mechanical anchoring.

In another aspect of the disclosed subject matter, a rapid, automated mesh onlay affixation and augmentation system is disclosed. In certain embodiments, the system can rapidly, precisely affix mesh to a primarily closed fascial incision of the abdominal wall of any kind, including the suture repair fascia after incisional access to the abdomen, after hernia repair and anterior fascial closure, and in circumstances where the anterior fascia can be reinforced. The system can be a medical grade, electro-mechanical or mechanical, composite plastic/metal, hand-held, disposable onlay, mesh affixing system that standardizes the advancement, tension-setting, and deployment of mesh in PMA procedures. The device can provide the interface for a piece of mesh, tacks, and fascia to be intimately and automatically affixed in a load-sharing or load-bearing manner.

In certain embodiments, the device can be designed ergonomically to facilitate ease of use and a narrow device-fascia-mesh-interface (DFMI) can allow for ease of use with minimal soft tissue undermining. The device can leverage the unique DFMI to precisely apply the minimum amount of mesh needed to augment closed fascia of the abdomen, such that mesh burden is minimized and so that the mesh can be applied precisely without irregularities. The device can accept spools of pre-rolled mesh, of different sizes (widths and lengths) and types (e.g., permanent synthetic absorbable or non-absorbable mesh, a biologic mesh, or bio-absorbable mesh or a hybrid mesh formed from components of each). The device can employ disposable cartridges of tacks (e.g., permanent or slow-absorbing) to affix the mesh (e.g., curved, tension sharing, uni-directional, or even screw-like tacks) and/or medical adhesive. The device can create tension across the mesh such that the anterior fascia is unloaded.

In the same or another embodiment of the disclosed subject matter, the device can integrate and automate three aspects of PMA: mesh tension-setting, mesh affixation, and mesh advancement. The integration and automation of these tasks can be accomplished using an internal, electromechanical or mechanical, mesh tensioning/displacement apparatus with a synchronous tacking mechanism. The device can rapidly affix tension-set mesh to the abdominal wall with subsequent automated advancement. Within the device, the mesh can laterally be displaced via two arms such that the mesh is stretched approximately <1 mm-5 mm bilaterally, and then rapidly and automatically affixed in <1-3 cm segments to the abdominal wall. The device also can have features to allow for safe visualization of repaired fascia so as to not deviate to one side, and can allow for placement of tacked mesh lateral to the suture repair.

By automating, standardizing, and integrating the aspects of successful PMA, the device in the same or another embodiment of the disclosed subject matter can reduce variation in technique, improve or optimize mesh reinforcement, and deliver a cost-efficient solution to certain high-risk laparotomies.

BRIEF DESCRIPTION OF THE DRAWINGS

Further features, the nature, and various advantages of the disclosed subject matter will be more apparent from the following detailed description and the accompanying drawings in which:

FIG. 33B depicts a perspective top view of the applicator of FIG. 33A.

Figure 1A:
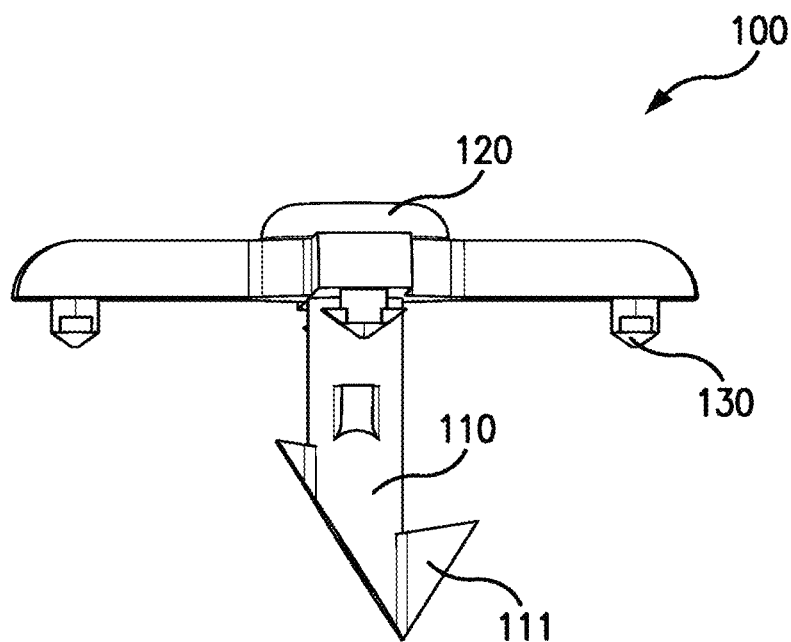
FIG. 1A illustrates a mesh fastener in accordance with an exemplary embodiment of the disclosed subject matter.

Throughout the drawings, the same reference numerals and characters, unless otherwise stated, are used to denote like features, elements, components or portions of the illustrated embodiments. Moreover, while the disclosed subject matter will now be described in detail with reference to the figures, it is done so in connection with the illustrative embodiments.

DETAILED DESCRIPTION

The disclosed subject matter provides systems and methods for mesh onlay fixation to abdominal wall fascia.

Generally, for purpose of illustration and not limitation, one aspect of the disclosed subject matter includes a custom mesh tension-applicator to engage with a pre-fabricated mesh strip through a mating process with a uni-direction fastener, then stretch and precisely affix a mesh strip to the anterior abdominal fascia. Assembled mesh-strips can have pre-fabricated fastener anchors and coupled to a mating interface element. As used herein, the term "mesh strip" is not limited to a mesh of any particular geometric. One of skill in the art will appreciate, for example, that a "mesh strip" can include a mesh construct of any geometry, size, or composition.

As embodied herein, the fastener-anchors can include a fastener for engaging with the applicator and an anchor for insertion into tissue, such as abdominal fascia. The fastener-anchors can be formed from a single piece or can include a plurality of pieces. For example, as described herein, the fastener for engaging with the applicator and the anchor for insertion into the fascia can be separate pieces coupled or affixed together. Alternatively, the fastener for engaging with the applicator and the anchor for insertion to the fascia can include different portions of a single piece. For purpose of clarity, the term "fastener," as used herein, can refer to the fastener-anchor collectively.

The applicator can interface with the mating interface allowing incremental, controlled device-mediated mesh tensioning and subsequent application. The fastener system can serve two functions: interaction/engagement and subsequent, incremental tension-setting via applicator; and penetration of the fascia and affixation of the mesh strip. Moreover, the applicator can have a spring to allow for out of plane fixation and can include a tensiometer to gauge how much tension the mesh is placed under. In this manner, surgeons can understand how much tension the mesh is placed under to gauge how much tension benefit may be achieved and the mesh can be applied.

Description will now be made to various embodiments of this aspect of the disclosed subject matter for purpose of illustration and not limitation. Although the embodiments described herein are described primarily with reference to abdominal fascial augmentation for hernia repair and/or hernia prevention through fascial reinforcement, one of skill in the art would appreciate that the subject matter disclosed herein can also be applied to a variety of other procedures. For example, in addition to being used to treat and augment hernia fascia closures, the disclosed subject matter can be utilized for open inguinal hernia repair for mesh reinforcement. As another example, for purpose of illustration and not limitation, the disclosed subject matter can also be utilized for laparoscopic surgery, including laparoscopic hiatal hernia, ventral or incisional hernia, inguinal hernia, or the like. Additionally, the disclosed subject matter can be utilized for augmentation and/or reinforcement of laparoscopic port sites following laparoscopic procedures.

Moreover, although the embodiments herein are described primarily with reference to the tensioning and affixation of mesh constructs, one of skill in the art will also appreciate that the disclosed subject matter can also include tensioning and applying other constructs, such as tissue, in a similar manner by integrating fasteners into those constructs. For example, the disclosed subject matter can be utilized to apply a tension-set soft tissue for skin closure or to incrementally close a wound subject to the application of tension. Other applications intended to fall within the scope of the disclosed subject matter include, for purpose of illustration and not limitation, reinforcement and re-contouring of the fascia after rectus fascia plication for abdominoplasty (using mesh), and tendon or joint repair, where tendon can be adapted into the fastener anchor and controlled and tensioned with an applicator so as to re-affix or reconstruct the tendon or joint capsule.

Figure 1B:
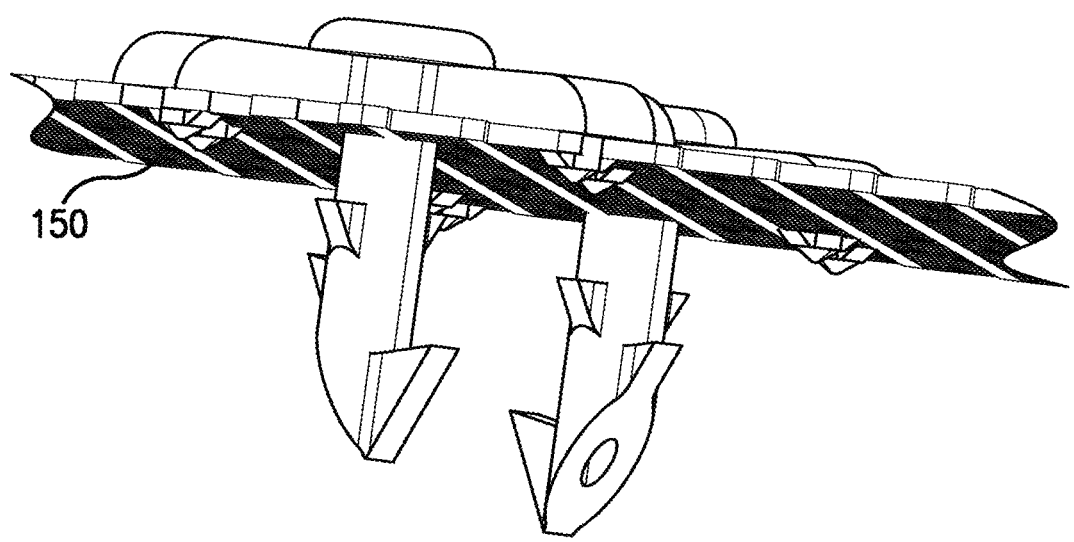
FIG. 1B illustrates a pre-integrated mesh-fastener in accordance with an exemplary embodiment of the disclosed subject matter.
Figure 1C:
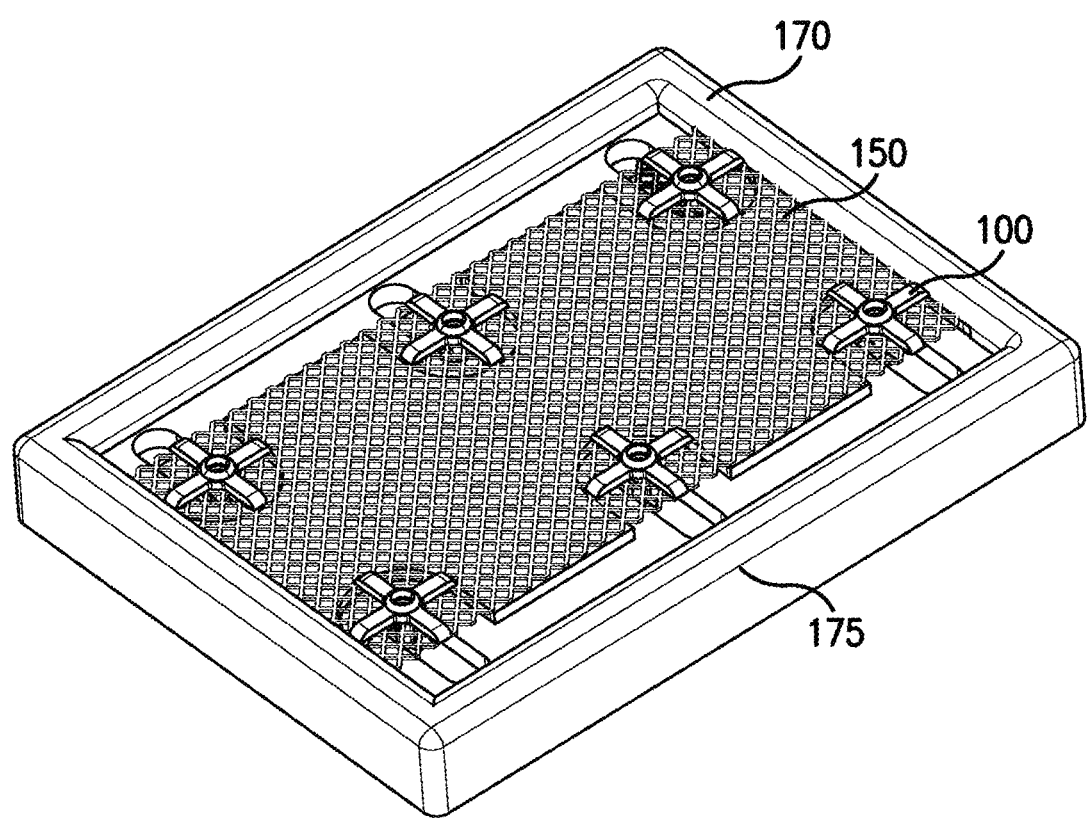
FIG. 1C illustrates a pre-assembled tray with mesh strip and integrated fasteners in accordance with an exemplary embodiment of the disclosed subject matter.

FIGS. 1A-1C depicts an exemplary embodiment of the disclosed subject matter. With reference to FIGS. 1A-1C, each fastener 100 can include an anchor 110. The anchor 110 can be adapted for affixation to anterior abdominal wall fascia. For example, the anchor 110 can include a barbed affixation having a length suitable for fascia penetration of a desired depth. In connection with an exemplary embodiment, the barbed affixation can be adapted for fascia penetration of 3.5 mm. The barbed affixation may include one or more barbs 111 for anchoring in the fascia. Additionally, various embodiments can include barbs differing in position, size, angle, direction, and the like. One of skill in the art will appreciate that the shape and configuration of anchor 110 depicted in FIGS. 1A-1C are exemplary and that a variety of other shapes and configuration are contemplated within the scope of the disclosed subject matter, including but not limited to those depicted in FIGS. 4A-4D, 6, 7, 8, 9, and 10.

Figure 12A:
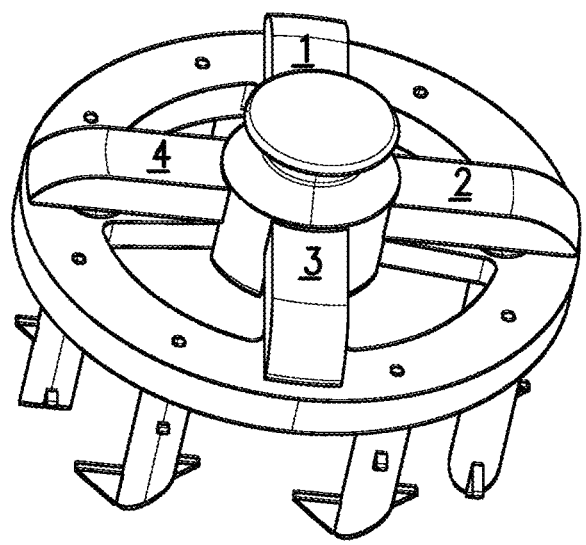
FIG. 12A illustrates a fastener with four radial support arms in accordance with an exemplary embodiment of the disclosed subject matter.
Figure 12B:
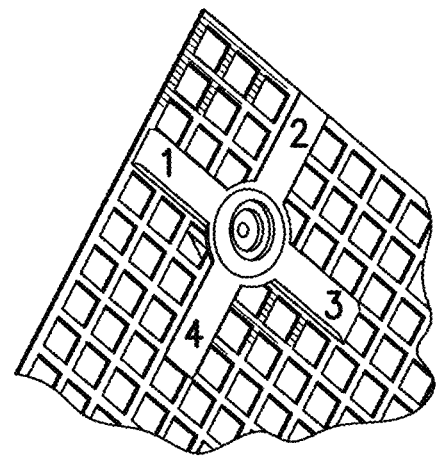
FIG. 12B illustrates a fastener with four radial support arms in accordance with another exemplary embodiment of the disclosed subject matter.
Figure 12C:
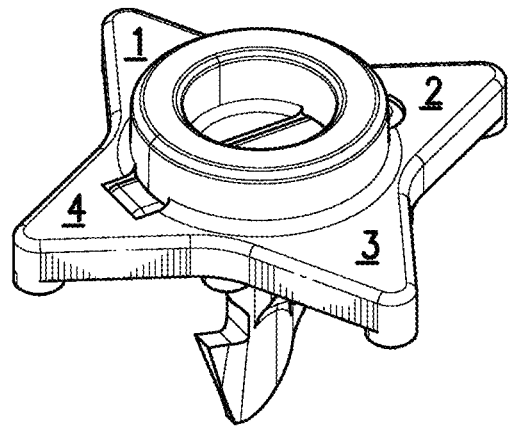
FIG. 12C illustrates a fastener with four radial support arms in accordance with another exemplary embodiment of the disclosed subject matter.

The fastener 100 can be adapted to be integrated with a mesh strip 150, for example as depicted in FIG. 1B. The fastener 100 can be disposed over the mesh strip 150 such that the anchor 110 is passed through a loop or hole of the mesh. Additionally and/or alternatively, and in accordance with an exemplary embodiment, the fastener can include a plurality of radial arms, each of which have one or more structural features suitable for integration with the mesh strip 150. For example, each radial arm can include a tab or post 130 that is short relative to the anchor 110 and can be inserted into a loop or hole of the mesh strip 150. In this manner, the fastener 100 can be integrated across a larger surface area of the mesh 150 to achieve stability during tensioning and enhance integration into mesh. For purpose of illustration, and not limitation, FIGS. 12A, 12B, and 12C illustrate fasteners with four radial arms (1, 2, 3 and 4) in accordance with various embodiments of the disclosed subject matter. Additionally and or alternatively, the fasteners can be pre-integrated with the mesh and manufactured together. For example, and not limitation, the fasteners can be integrally formed with or bonded to the mesh.

Figure 7:
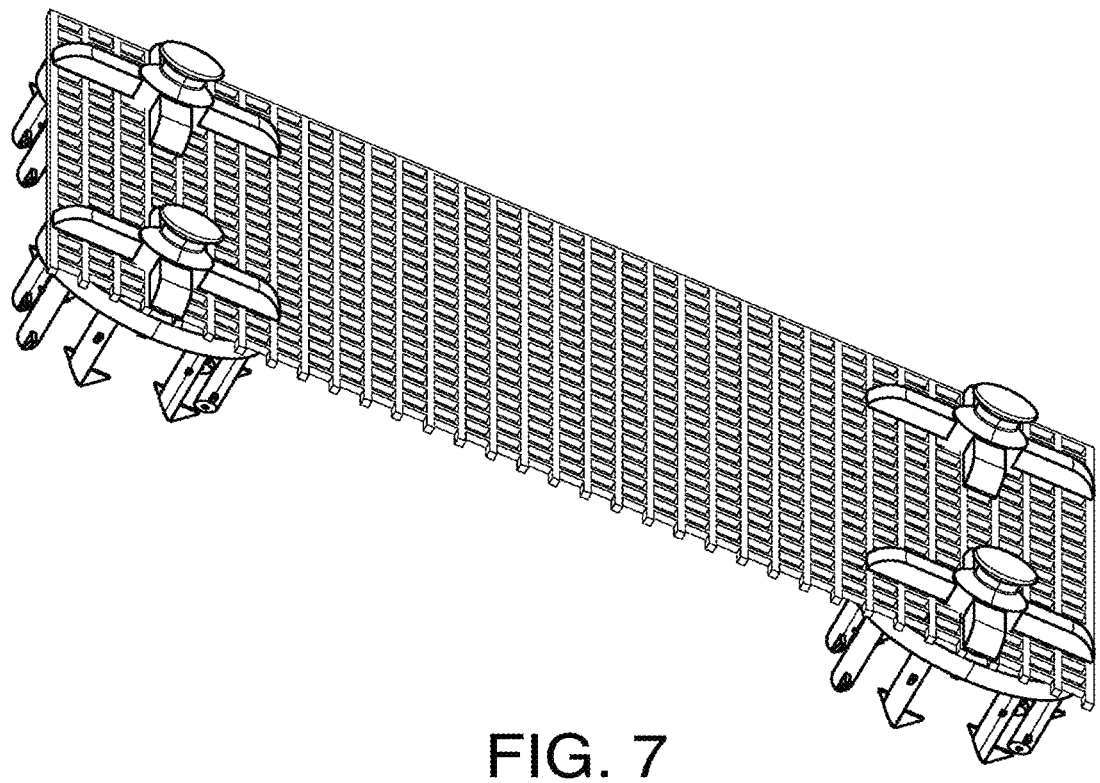
FIG. 7 illustrates a pre-integrated mesh-fastener in accordance with another exemplary embodiment of the disclosed subject matter.
Figure 8:
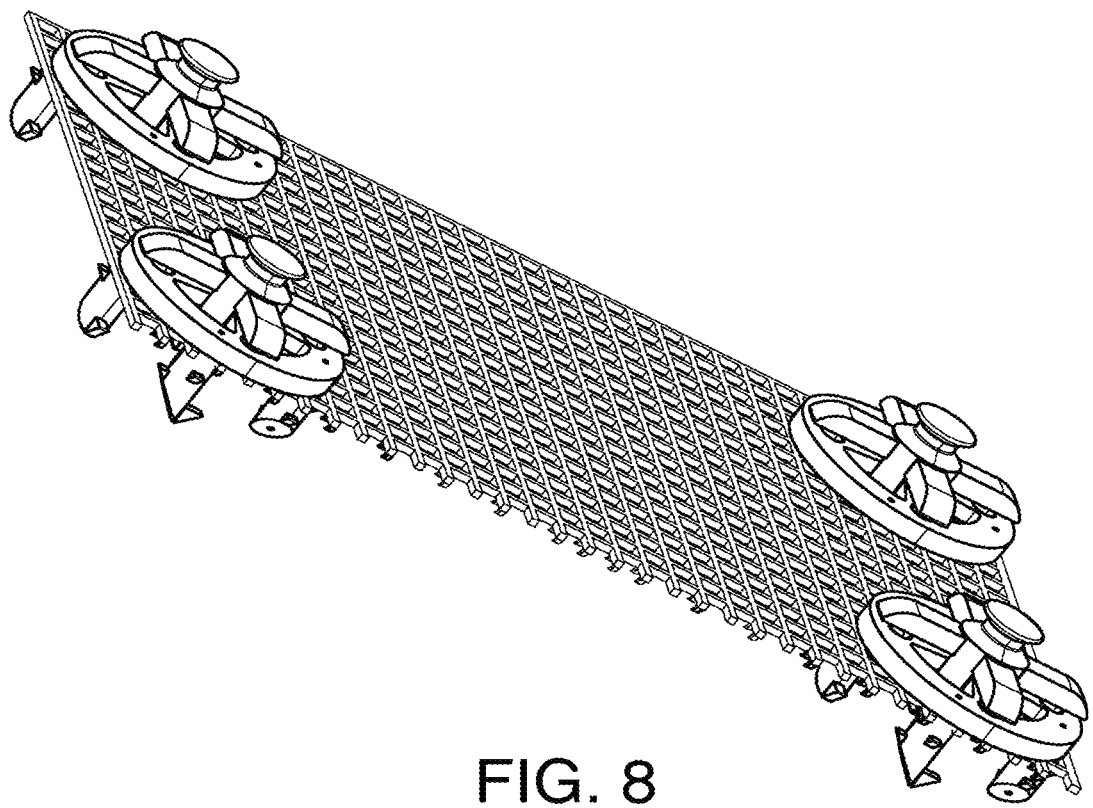
FIG. 8 illustrates a pre-integrated mesh-fastener in accordance with another exemplary embodiment of the disclosed subject matter.

In connection with embodiments which include a plurality of anchors, such as those depicted in FIGS. 7 and 8, the plurality of fasteners can be arranged radially outward from the center of the fastener and can be inserted into separate loops of the mesh. In this manner, the fastener can be integrated across a larger surface area of the mesh to achieve stability during tensioning. One of skill in the art will appreciate that the mesh strip 150 can be synthetic mesh, a biologic mesh, bio-absorbable mesh, or a variety of other meshes known to those of skill in the art.

Figure 4A:
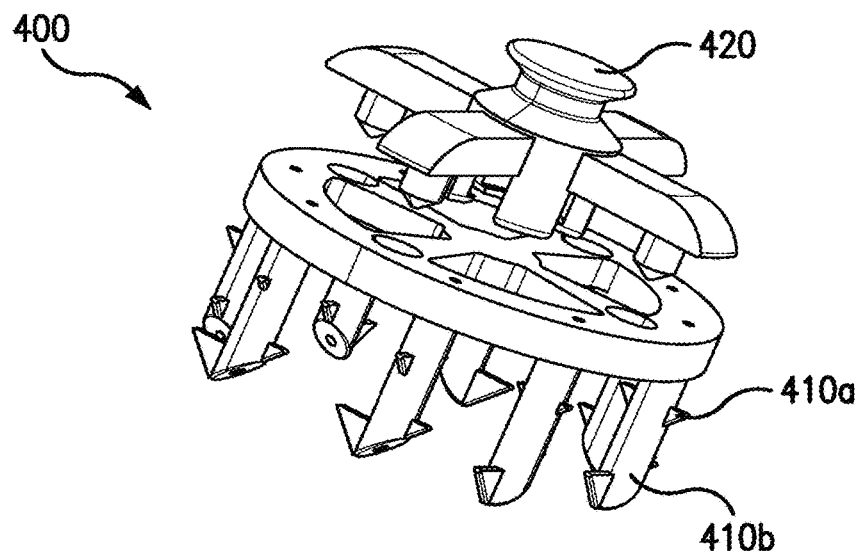
FIG. 4A illustrates a fastener in accordance with another exemplary embodiment of the disclosed subject matter.
Figure 4B:
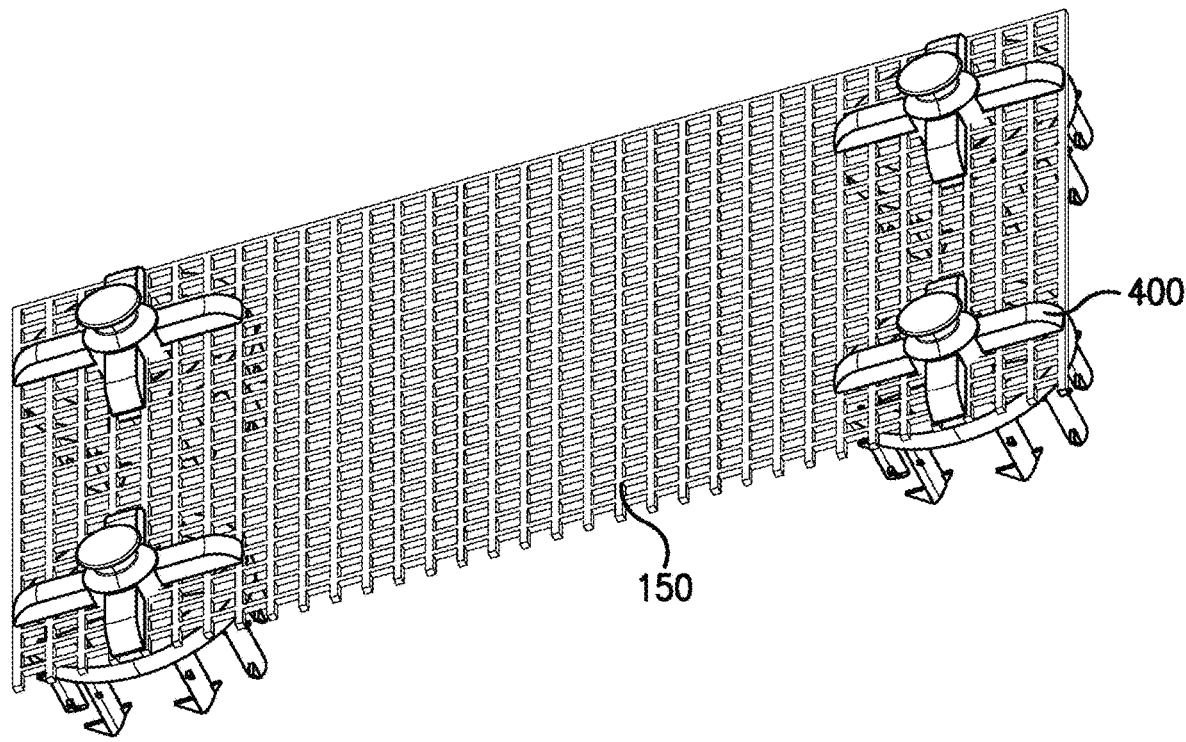
FIG. 4B illustrates an integrated mesh-anchor system with customized mesh strip and fasteners depicted in FIG. 4A in accordance with an exemplary embodiment of the disclosed subject matter.
Figure 4C:
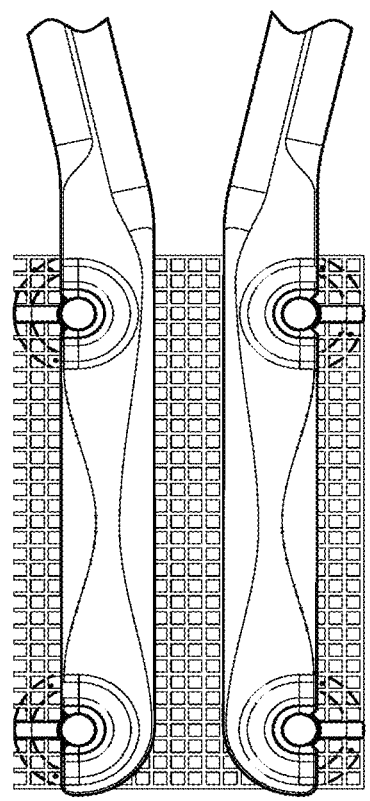
FIG. 4C is a schematic diagram of applicator tension arms mating with fasteners depicted in FIG. 4A in accordance with an exemplary embodiment of the disclosed subject matter.
Figure 4D:
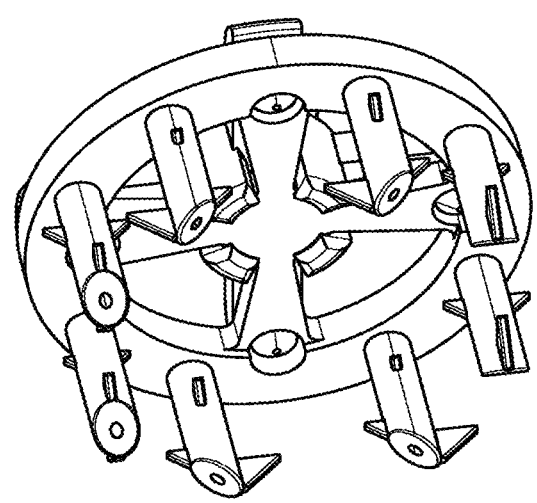
FIG. 4D illustrates a bottom view of the fastener of FIG. 4A.

Additionally and/or alternatively, with reference to FIGS. 4A-4D, which depict another exemplary embodiment of the disclosed subject matter, the fastener 400 can include at least two pieces. One piece can include structural features which allow for the receipt and affixation of the other piece. In connection with certain embodiments, this other piece can be an existing fastener. The fastener 400 can be integrated with the mesh strip by aligning the top piece, e.g., the piece that includes mating interface 420 on one side of the mesh 150 and aligning the other piece, e.g., the piece that includes one or more anchors 410a, 410b, on the other side of the mesh 150. The pieces can then be mated such that structural features of the top piece are inserted through loops or holes of the mesh, thereby integrating the fastener with the mesh. Additionally or alternatively, holes can be punched out of the mesh or other construct to accommodate the structural features and insertion of the fastener. In accordance with an exemplary embodiment, for purpose of illustration and not limitation, a snap-lock mechanism can be used to securely attach the top and bottom pieces of the fastener, as illustrated in FIG. 4D. The circumferential snap-lock can include structural elements on the top part of the fastener that hug the inner hub of the bottom piece. This can secure the mesh in between the fastener pieces. In connection with other embodiments, the top piece and the bottom piece can be mated using a variety of other configurations. For example, and not limitation, the pieces can be attached using a twist-in mechanism, a snap through mechanism, either from above or below. Moreover, the mating components can vary in their position and arrangement.

Figure 2A:
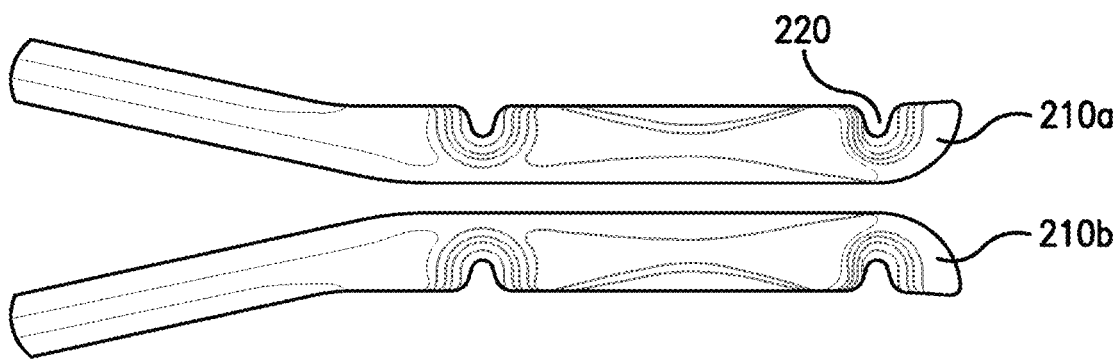
FIG. 2A depicts an image of tension applicator arms fabricated from an acrylonitrile butadiene styrene (ABS) material using the Fused Deposition Modeling (FDM) process in accordance with an exemplary embodiment of the disclosed subject matter.
Figure 2B:
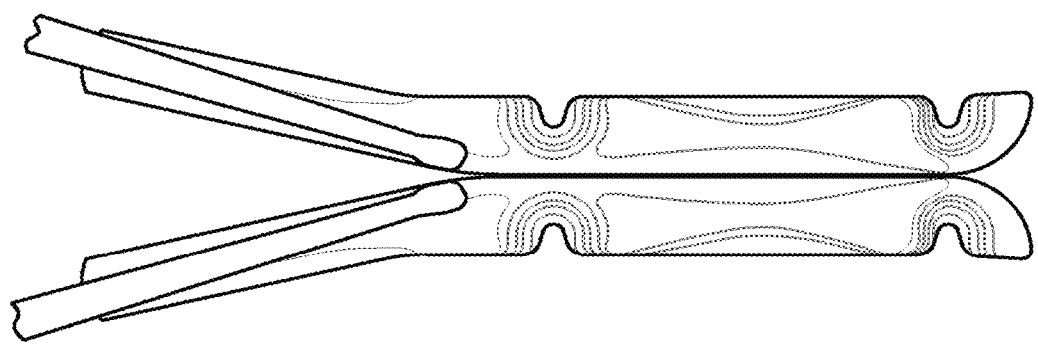
FIG. 2B depicts another image of tension applicator arms fabricated from an acrylonitrile butadiene styrene (ABS) material using the Fused Deposition Modeling (FDM) process in accordance with an exemplary embodiment of the disclosed subject matter.
Figure 2C:
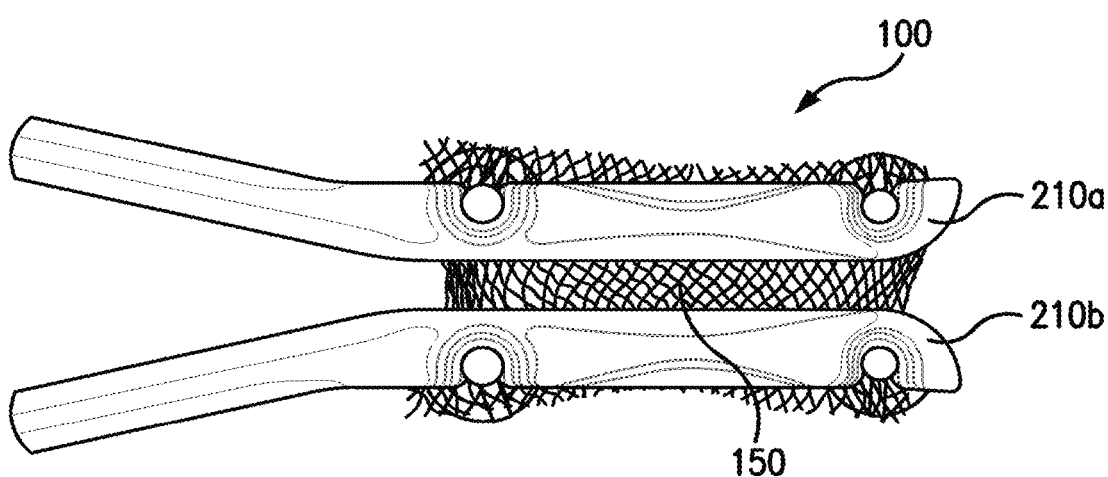
FIG. 2C illustrates a demonstration of device-mediated mesh tension in accordance with an exemplary embodiment of the disclosed subject matter.

The fastener 100 can also include a mating interface 120 adapted to interface with tension arms of an applicator. In an exemplary embodiment, the mating interface 120 can take the form of a post or knob. For example, with reference to FIGS. 2A-2C, the tension arms 210a, 210b of the applicator can include ports (e.g., port 220) adapted to receive the posts 120. In accordance with an exemplary embodiment, as depicted in FIGS. 2A-2C, the tension arms 210a and 210b can have a port for each fastener knob 120 and the ports can be spaced at a predetermined interval so as to maintain a predetermined vertical tension on the mesh strip 150.

One of skill in the art will appreciate that the shape and configuration of the mating interfaces 120 and the number and shape of the ports 220 can be varied as desired. For example, as illustrated by FIG. 4A, which depicts another exemplary embodiment of the disclosed subject matter, the fastener 400 can include a mating interface 420 comprising a post with a spool shape. As illustrated by FIG. 4C, the tension arms can mate with the mating interface 420 using a knob and hook mechanism to engage the fastener top with the applicator in order to allow for tensioning.

Figure 5:
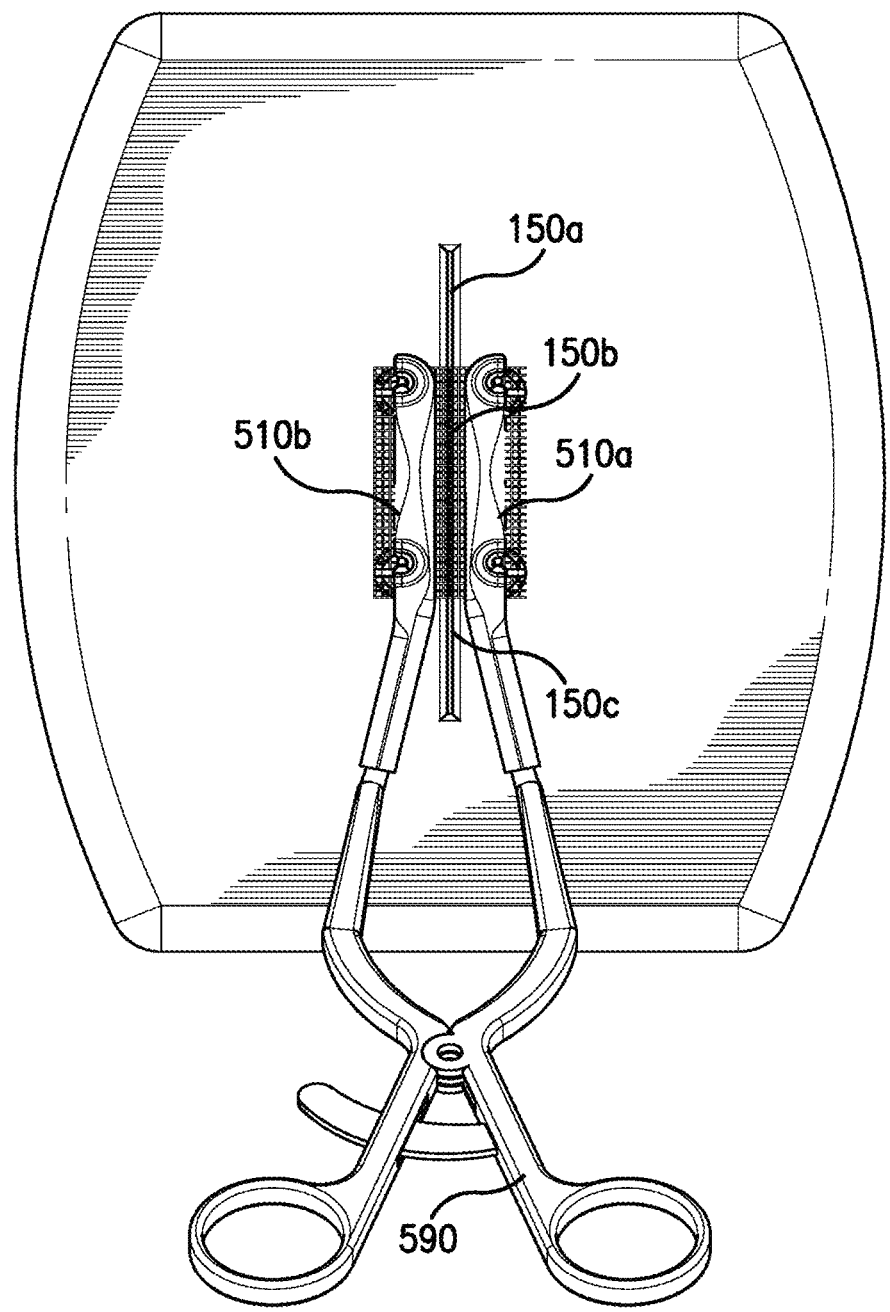
FIG. 5 illustrates a demonstration of an applicator and mesh-anchor strips being applied to abdominal wall fascia in accordance with an exemplary embodiment of the disclosed subject matter.

Alternatively, the mating interface may have a variety of other configurations, such as those depicted in FIGS. 6, 7, 8, 9, and 10. One of skill in the art will appreciate that the number and shape of the ports 220 of the tension arms 210a and 210b can be varied to accommodate the number and shape of the posts. For example, and as illustrated by FIG. 5, which depicts another exemplary embodiment of the disclosed subject matter, the tension arms 510a and 510b can include ports adapted to entirely receive the mating interface element of the fasteners.

Figure 11:
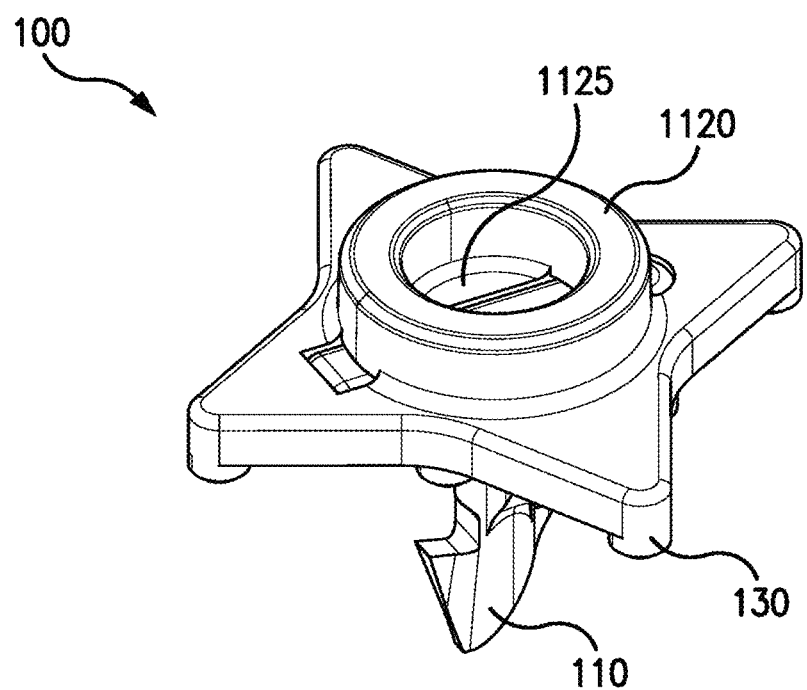
FIG. 11 illustrates a fastener in accordance with an exemplary embodiment of the disclosed subject matter.

In connection with an exemplary embodiment and with reference to FIG. 11, for purpose of illustration, the mating interface 120 can be a structural element 1120 including a hole 1125 at the top of the fastener 100 to allow for engagement with pins on the head of the applicator. Additionally, the applicator can include a spring for out of plane fixation. For example, the tension arms of the applicator can include telescoping elements that can be inserted into the hole 1125 of the mating interface, and the handle of the applicator can include a button for controlling an out of plane spring to securely mate the tensioning arms to the mating interface. This arrangement can reduce the effort to engage the applicator with the mating interface.

In connection with certain embodiments, the fasteners can include at least three pieces. The fastener can include the top fastener portion for mating with an applicator and a bottom portion for attaching the fastener portion to the mesh strip, for example as described above with reference to FIGS. 4A-4D. In accordance with these embodiments, the fasteners also include the anchor, which can be a separate piece. For example, and not limitation, the top fastener portion and the bottom portion can be configured to house the anchor when connected together from opposite sides of the mesh such as depicted in FIGS. 14A-14F. In this manner, the anchors need not be formed from the same material or be integral with either the top fastener portion or the bottom portion. As such, as embodied herein, conventional anchors can be used. That is, for example and in accordance with this embodiment, the top fastener portion and the bottom portion can be configured to house existing anchors.

As embodied herein, for purpose of illustration, fasteners in accordance with various embodiments can include three components. First, the fasteners can include a fastener portion or mating post for interfacing with the applicator as described herein. Second, the fasteners can include an anchor or tissue penetrating mechanism. This mechanism can be an existing anchor or tacks or a special purpose anchor configured to integrate with the system described herein. The anchor/tissue penetrating mechanism can, for example, snap into the fastener portion. Third, the fasteners can include an under piece or bottom piece that integrates with the fastener portion/mating post to lock the fasteners into the mesh to be controlled with our without the tissue penetrating mechanism. The anchor/tissue penetrating mechanism can, for example, snap into the fastener portion or the bottom piece.

Moreover, in certain embodiments, the fasteners need not be pre-integrated with an anchor. Rather, for example and not limitation, the fasteners can include a top fastener portion and a bottom portion for affixation to the mesh and can also include a target, such as a hole or sink, for receiving an anchor after tensioning has occurred. That is, the fasteners can be integrated into the mesh so that the applicator may be used to appropriately tension the mesh and then, once the mesh has been tensioned and positioned over a desired area, e.g., a fascial incision, the anchors can be inserted and the mesh can be affixed to the fascia, such as depicted in FIG. 32.

Figure 32:
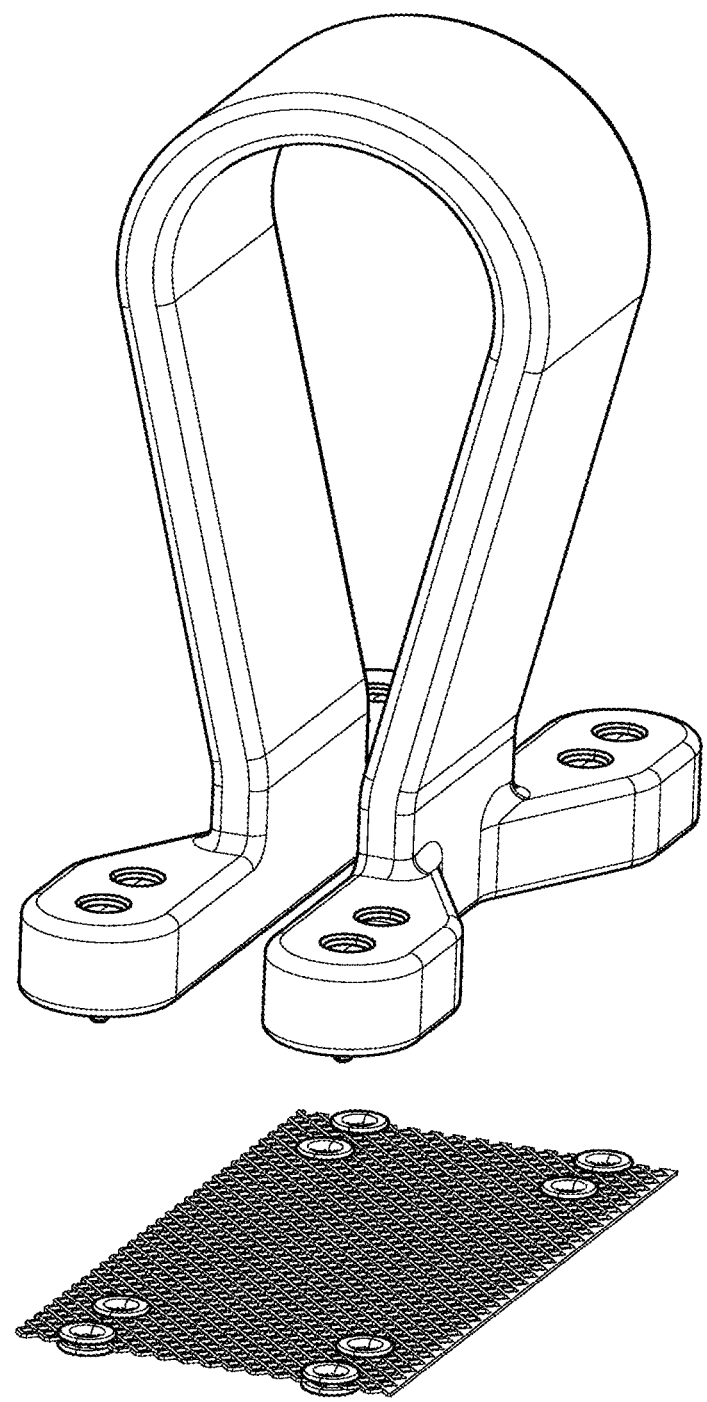
FIG. 32 depicts an applicator and mesh strip with integrated fasteners without anchors in accordance with an embodiment of the disclosed subject matter.

Additionally and/or alternatively, in connection with certain embodiments and with reference to FIG. 32, the fasteners can be interested into the mesh such that an applicator can tension the mesh and allow for subsequent insertion of tacks or anchors through other areas of the mesh. For example, the fasteners can have a grommet shape, and the applicator can have protrusions adapted to be inserted into the center of the fasteners to allow for tensioning. One of skill in the art will appreciate that the fasteners of this embodiments, as well as others, can be formed in the mesh or can be formed from separate pieces and integrated with the mesh. Once the mesh is tensioned, the surgeon can apply tacks or anchors and then release the applicator by withdrawing the protrusions from the fasteners.

Figure 33A:
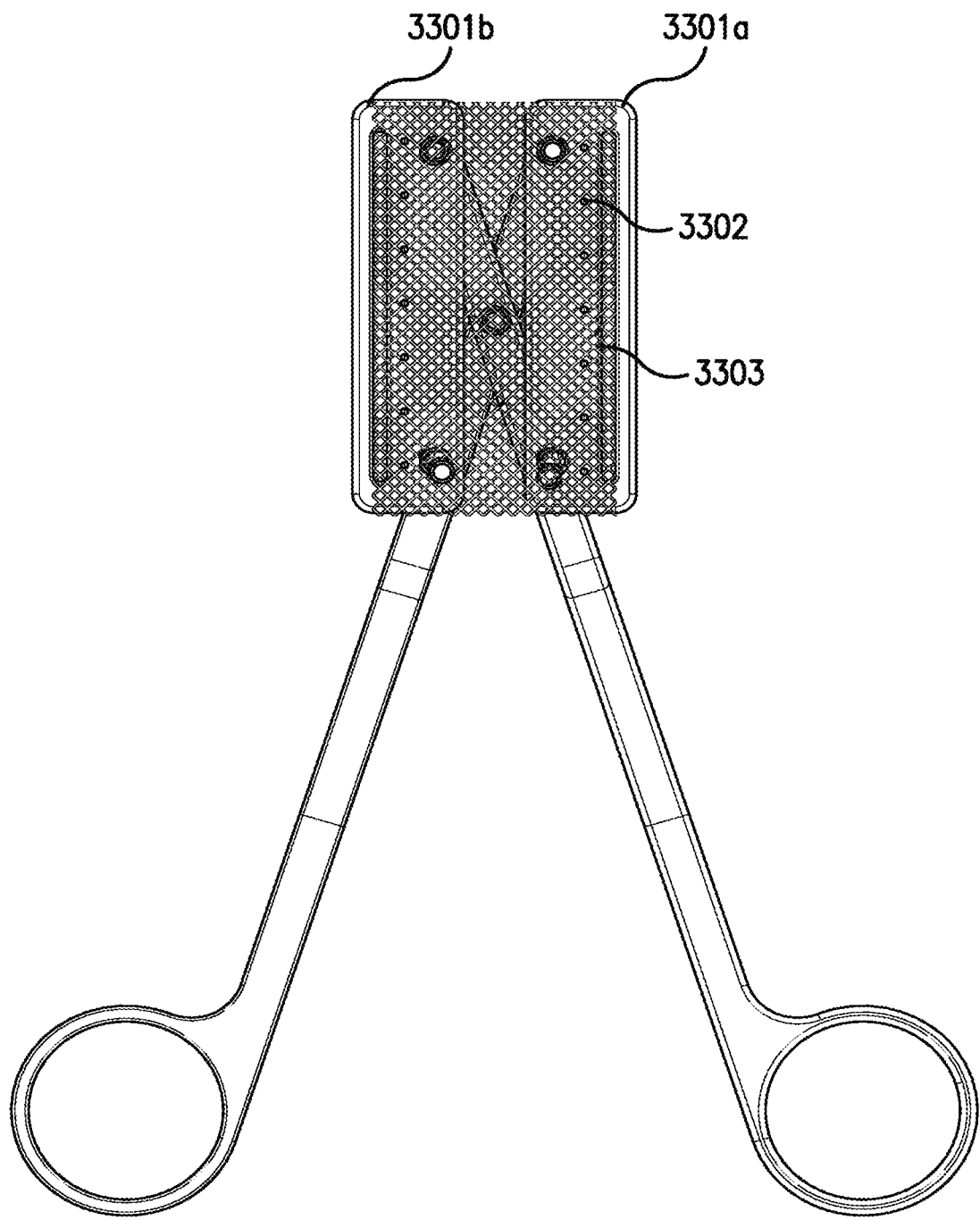
FIG. 33A depicts a bottom view of an applicator tensioning a mesh strip in accordance with an exemplary embodiment of the disclosed subject matter.
Figure 34A:
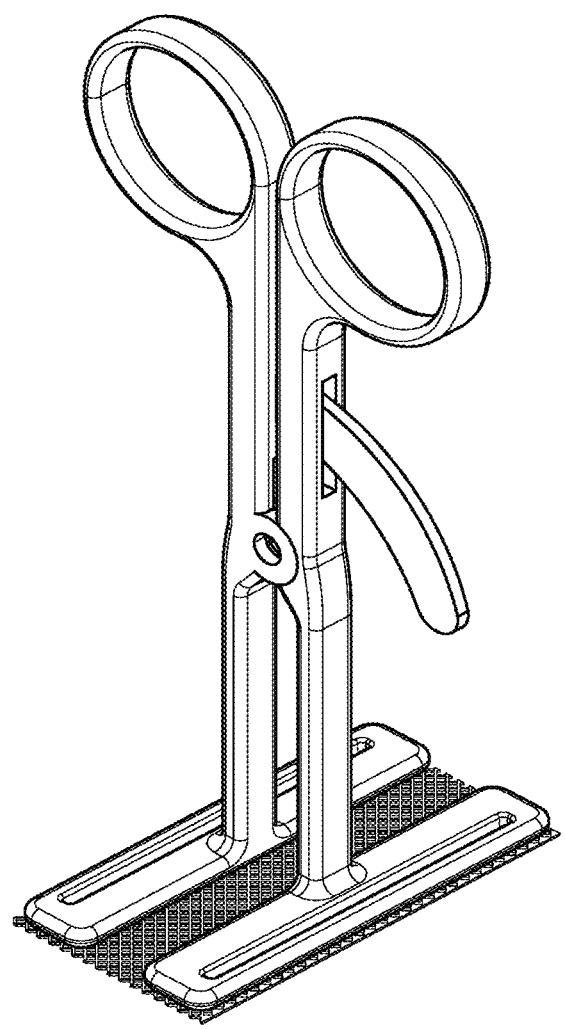
FIG. 34A depicts a perspective view of an applicator tensioning a mesh strip in accordance with an exemplary embodiment of the disclosed subject matter.
Figure 34B:
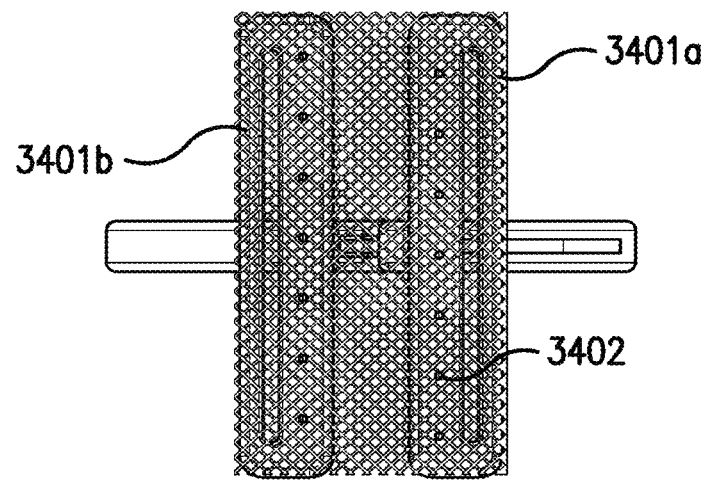
FIG. 34B depicts a bottom view of the applicator of FIG. 34A.

Additionally, in connection with certain embodiments and with reference to FIGS. 33A-33B and 34A-34B, a system for tensioning mesh strips can include an applicator configured to integrate itself into the mesh. For example, and not limitation, the applicator tensioning arms (3301*a* and 3301*b* in FIGS. 33A-33B; 3401*a* and 3401*b* in FIGS. 34A-34B) can include a plurality of protrusions (3302 in FIGS. 33A-33B; 3402 in FIGS. 34A-34B) shaped and adapted to be inserted into loops of the mesh strip. FIGS. 33A-33B illustrate an applicator in accordance with an exemplary embodiment of the disclosed subject matter in which handles are connected by rotation mechanism 3350 in a manner similar to that of pliers. When the handles are widened, the mesh can be tensioned by virtue of the protrusions 3302 inserted into the mesh loops. The applicator can also include a hole or window 3303 to allow for application of anchors or tacks after the mesh has been tensioned and positioned over the fascia. In this manner, a surgeon can rapidly tension a mesh strip, position the mesh strip over the fascia, and insert fasteners or tacks to affix the mesh strip. FIGS. 34A-34B illustrate another applicator in accordance with the disclosed subject matter. In connection with this embodiment, rotation mechanism 3450 is configured such that closing the handles widens the tensioning arms 3401*a* 3401*b* and thus tensions the mesh.

With reference to FIG. 1C, and in accordance with an exemplary embodiment, the system can include a tray 170 adapted to hold the mesh strip 150 and integrated fasteners 100. The tray 170 can include one or more wells 175 that are adapted to receive the anchors 110 of the fasteners 100 such that, while in the tray, the pre-assembled mesh strip 150 is maintained at a predetermined horizontal and vertical tension. This can allow for efficient mating and/or interfacing with the tension arms 210*a* and 210*b* of the applicator.

As used herein, for purpose of clarity, horizontal tension refers to tension in the direction of a force applied by the tension arms 210*a* and 210*b* and vertical tension refers to tension in a direction orthogonal to the horizontal direction.

In accordance with an exemplary embodiment, the applicator can also include a tensiometer. The tensiometer can measure and display how much tension the mesh is placed under. In this manner, surgeons can understand how much tension the mesh is placed under to gauge how much tension benefit may be achieved. One of skill in the art will appreciate that the tension applied can impact the efficacy of the mesh augmentation and can vary the tension based as desired. For purpose of illustration, and not limitation, application of approximately 1-10 mm of mesh tensioning can occur in accordance with an exemplary embodiment of the disclosed subject matter, which can generate a force of several N.

In accordance with another exemplary embodiment, the tray can be adapted to house a plurality of mesh strips. For example, with reference to FIG. 5, the tray 570 can be adapted to house mesh strips 150*a*, 150*b*, and 150*c*. In this manner, the applicator 590 can be utilized to mate with a first strip, e.g., 150*a*, affix the first mesh strip to a fascial incision, and mate with a second strip, e.g., 150*b* for subsequent affixation.

Figure 13A:
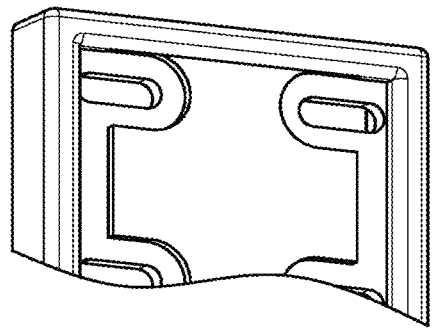
FIG. 13A illustrates a tray in accordance with an exemplary embodiment of the disclosed subject matter.
Figure 13B:
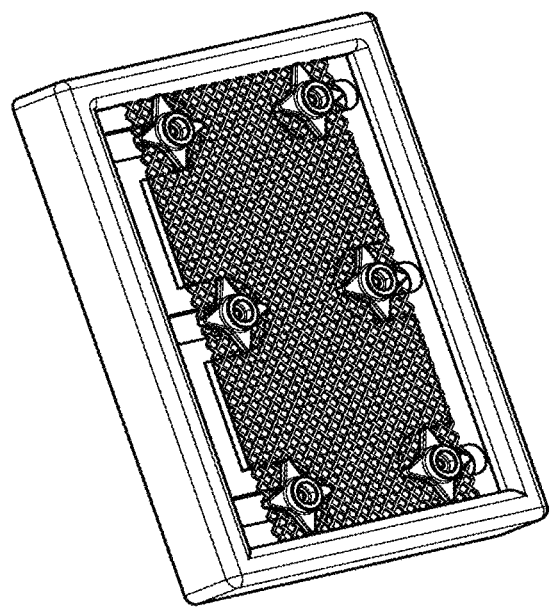
FIG. 13B illustrates a tray with a mesh strip and pre-integrated fasteners in accordance with an exemplary embodiment of the disclosed subject matter.
Figure 13C:
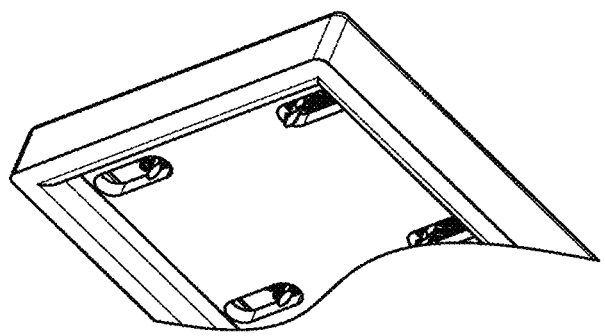
FIG. 13C illustrates a bottom view of the tray of FIG. 13B.

In connection with certain embodiments, as illustrated by FIGS. 13A-13C, the tray can include holes through which the barbed affixation of the fastener can be inserted. These holes can be adapted such that the radial posts of the fasteners are supported by the tray. In connection with fasteners having a mating interface including a hole into which elements of the tensioning arms of the applicator are inserted, this configuration can provide structural support during docking. For example, the tension arms of the applicator and be aligned with the tops of the fasteners supported by the tray, and the surgeon can apply a downward force to "snap" structural elements on the bottom of the tension arms into the mating interface holes of the fasteners. The tray can provide structural support to the radial arms of the fastener, such that the barbed affixations of the fasteners are not damaged during mating with the applicator. Trays can be stacked for packaging and rapid intra-operative use so that they may be slide off to reveal the next mesh strip.

As noted above, the mesh strip 150 can be integrated with a plurality of fasteners 100 and tension arms 210*a* and 210*b* can be adapted to receive the fasteners 100 such that vertical tension in the mesh 150 is maintained. Additionally, in accordance with an exemplary embodiment, the applicator may include a handle (e.g., handle 590 depicted in FIG. 5). The handle can be coupled with the tension arms (e.g., 210*a*, 210*b* of FIGS. 2A-2C or 510*a*, 510*b* of FIG. 5) such that the tension arms can be spread to control the horizontal tension of the mesh 150. For example, the handle can be coupled with the tension arms about an axis. That is, for example, the handle can be a scissor-style handle and can be coupled with the tension arms at a joint area including a pivot point. One eye ring of the handle can be coupled to the first tension arm 210*a* and the other eye ring of the handle can be coupled to the second tension arm 210*b*, such that movement of the eye rings causes a rotation around the pivot point and thereby spreads the tension arms. FIG. 2C depicts a mesh 150 with four fasteners 100 mated with tension arms 210*a* 210*b* such that both vertical and horizontal tensions are applied.

In accordance with the disclosed subject matter, the applicator interfaces and mates with the fastener mating interface allowing incremental, controlled, reproducible device-mediated mesh tensioning and subsequent application. After the applicator has been mated with the fastener mating interface and after mesh tensioning, the fasteners, and thus the mesh strip, may be affixed to the fascia by application of force either via the applicator or by hand. The fastener anchors can penetrate the fascia and thereby affix the mesh strip.

In accordance with certain embodiments, the force applied to the fasteners can be mediated mechanically or electro-mechanically through the applicator and by interfacing with the fastener mating interface and transduced into the mesh construct to allow for pre-tensioned application into fascia.

Figure 14A:
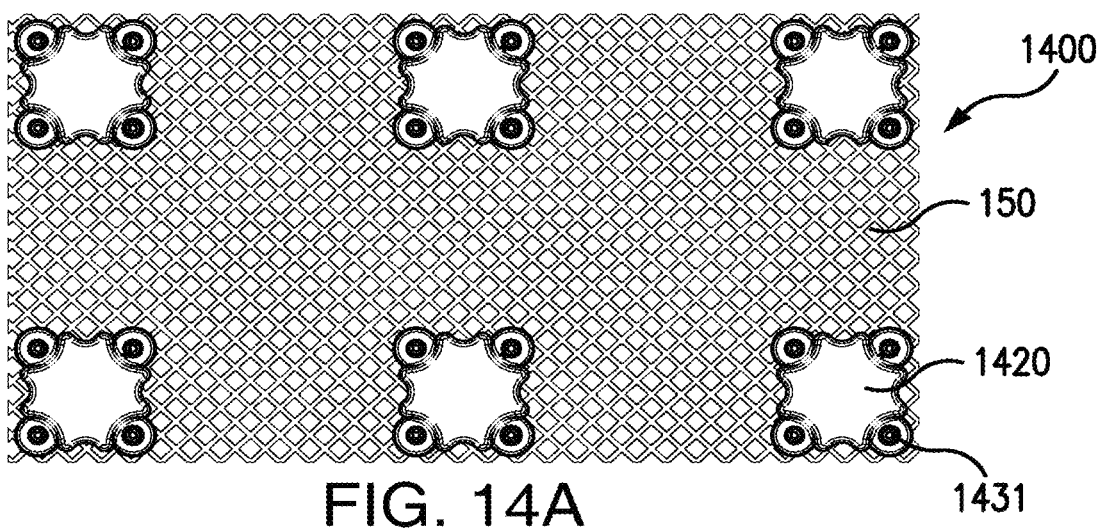
FIG. 14A illustrates a top view of a top portion of fasteners inserted into a mesh strip in accordance with another exemplary embodiment of the disclosed subject matter.
Figure 14B:
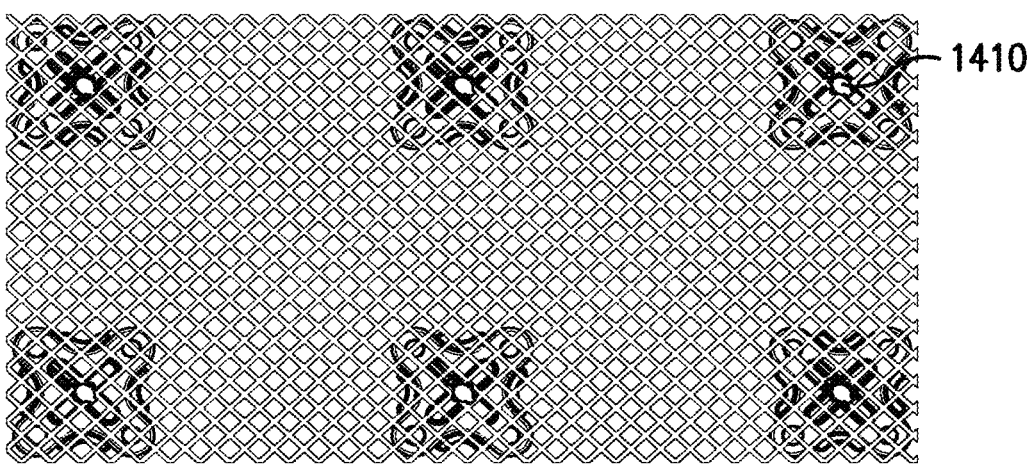
FIG. 14B is a bottom view of the mesh strip with inserted fasteners of FIG. 14A.

For purpose of illustration, and not limitation, description will now be made to another exemplary embodiment of the disclosed subject matter with reference to FIGS. 14A-17B. In connection with this embodiment, the mesh strip 150 can be integrated with six fasteners (e.g., fastener 1400) as illustrated in FIGS. 14A-14F. As embodied herein and as described above, each fastener 1400 can include a mating interface 1425 and a barbed affixation 1410. As illustrated by FIG. 14A, the fastener can include a top portion 1420 which is coupled to the barbed affixation 1410. The top portion 1420 can include holes 1431 at radial edges thereof. The barbed affixation 1410 can be inserted into a hole or loop of the mesh 150. FIG. 14A illustrates a top view of a mesh 150 with the barbed affixations 1410 of six fasteners (e.g., fastener 1400) inserted therein. FIG. 14B illustrates a bottom view of FIG. 14A, FIG. 14D illustrates a top perspective view of FIG. 14A, and FIG. 14E illustrates a bottom perspective view of FIG. 14A.

Figure 14C:
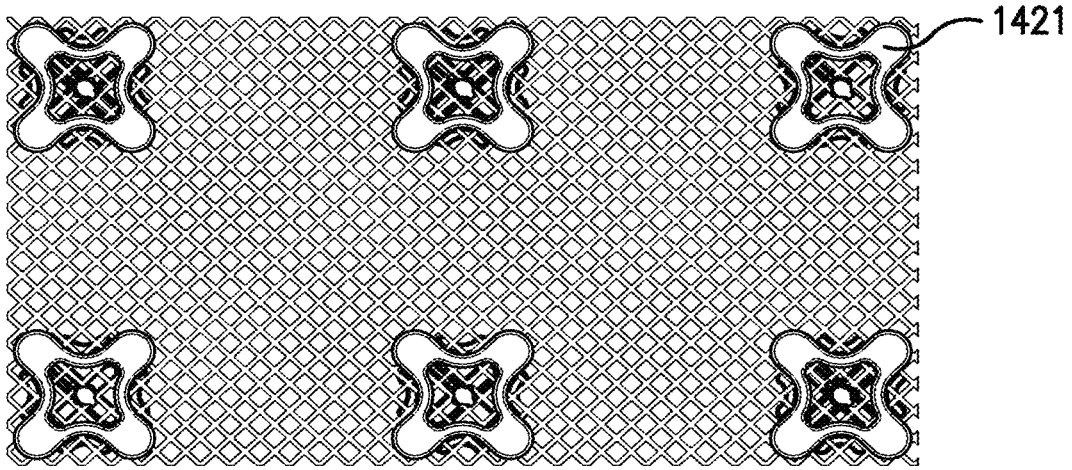
FIG. 14C is a bottom view of the mesh strip of FIGS. 14A and B after bottom pieces of the fasteners have been added to integrate the fasteners with the mesh.
Figure 14D:
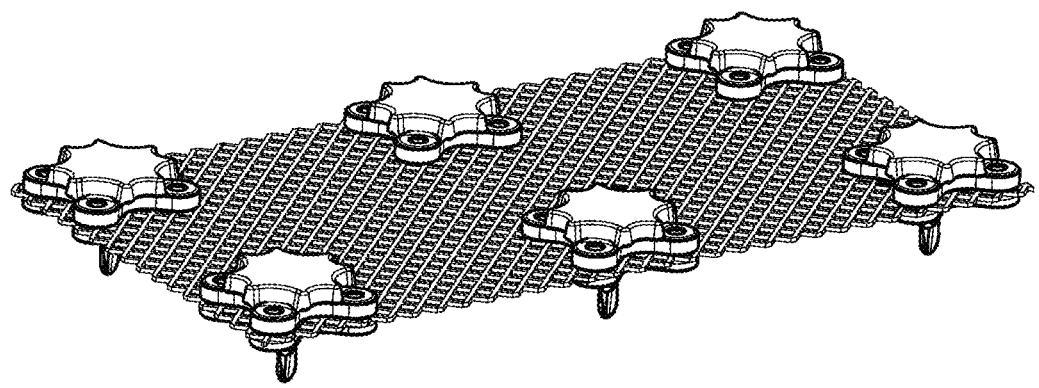
FIG. 14D is a top perspective view of the mesh strip with inserted fasteners of FIG. 14A.
Figure 14E:
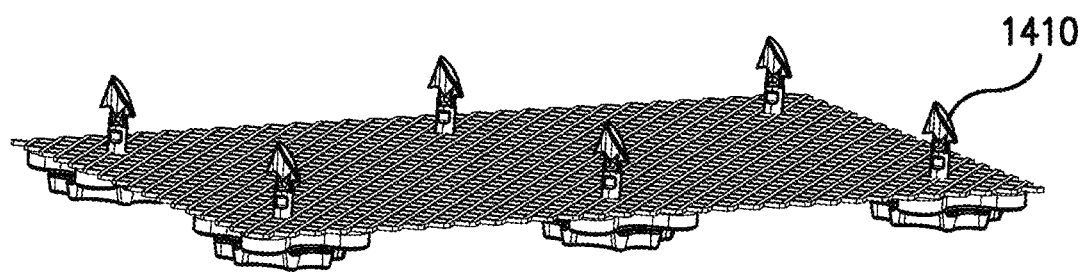
FIG. 14E is a bottom perspective view of the mesh strip with inserted fasteners of FIG. 14A.
Figure 14F:
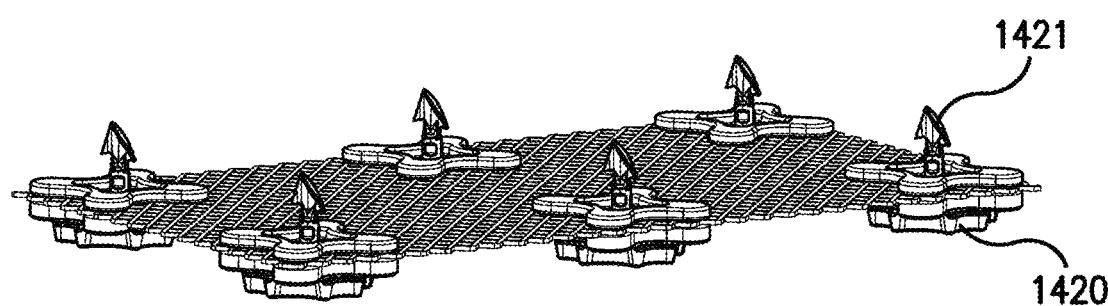
FIG. 14F is a bottom perspective view of the mesh strip with integrated fasteners of FIG. 14C.

Additionally, as illustrated by FIG. 14C and FIG. 14F, the fasteners 1400 can include a bottom retainer 1421. The bottom retainer 1421 can be aligned with the top portion of the fastener 1420 on an opposite side of the mesh. That is, for example, if the top portion 1420 of the fastener 1400 is aligned such that the barbed affixation 1410 is inserted through the top of the mesh, the bottom retainer 1421 can be positioned on the bottom of the mesh. The bottom retainer 1421 can then be permanently coupled to the top portion 1420. For example, and not limitation, the bottom retainer 1421 can include posts adapted to be inserted, through holes or loops of the mesh 150, into the holes 1431 of the top portion 1420 of the fastener 1400. In this fashion, the fastener 1400 can be integrated with the mesh 1400 in a manner that enhances the stability of the mesh during tensioning. FIG. 14C is a bottom view of the mesh 150 and fasteners (e.g., fastener 1400) of FIG. 14A after the bottom retainer 1421 has been coupled with the top portion 1420. FIG. 14F is a perspective view of FIG. 14A.

The integrated mesh and fasteners of FIGS. 14A-14F can be adapted for use with an applicator 1500. In accordance with an aspect of the disclosed subject matter, the applicator 1500 can have a shape resembling the capital letter Ω (Omega) of the Greek alphabet. For purpose of illustration, and not limitation, such an applicator 1500 is referred to herein as an "omega" applicator.

Figure 15A:
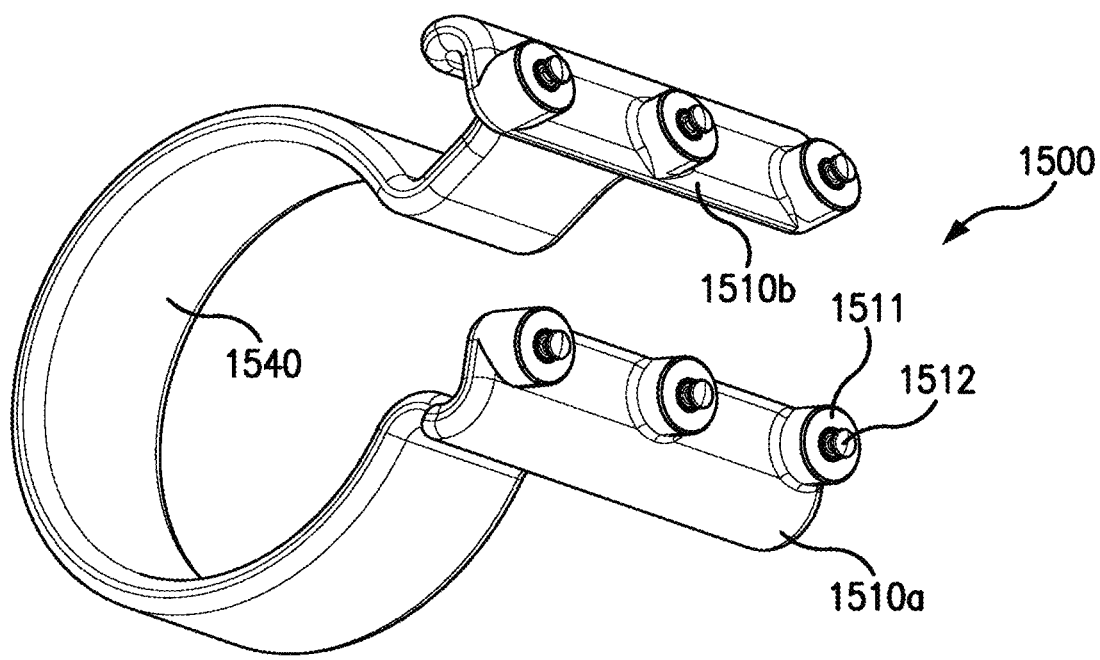
FIG. 15A illustrates an applicator in accordance with an exemplary embodiment of the disclosed subject matter in an expanded state.

The omega applicator 1500 can include a handle 1540 in the shape of a loop coupled with tensioning arms 1510a and 1510b. The loop 1540 can be formed from an elastic material having a suitable spring constant such that, in an expanded or resting state, the applicator 1500 has an omega shape and, upon application of force, e.g., by squeezing, the tensioning arms 1510a and 1510b can be brought together as illustrated by FIG. 15A (depicting an expanded state) and FIG. 15B (depicting a contracted state). One of skill in the art will appreciate that the loop 1540 can be fabricated from a variety of suitable materials and in a variety of different configurations to achieve a suitable spring constant. Moreover, one of skill in the art will appreciate that the loop 1540 and tensioning arms 1510a and 1510b can be formed as a single structure or different structural elements bonded or affixed together.

Figure 15B:
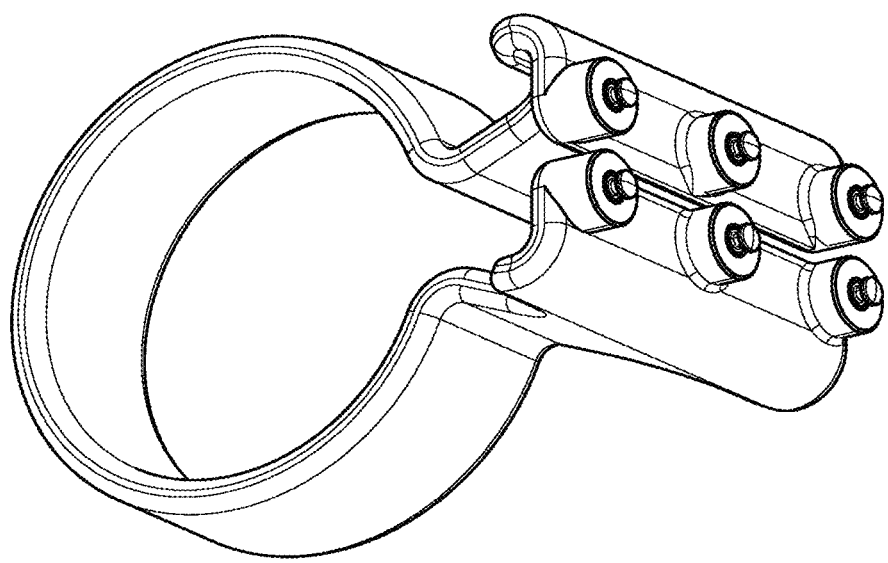
FIG. 15B illustrates the applicator of FIG. 15A in a contracted state.
Figure 16A:
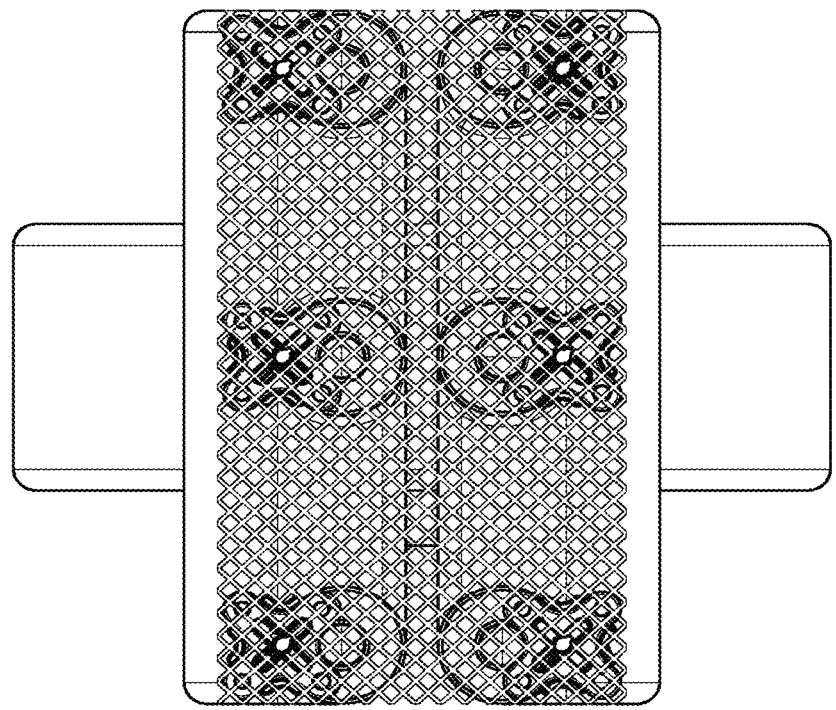
FIG. 16A illustrates a bottom view of the applicator of FIG. 15A after mating with the mesh strip of FIGS. 14A-F.
Figure 16B:
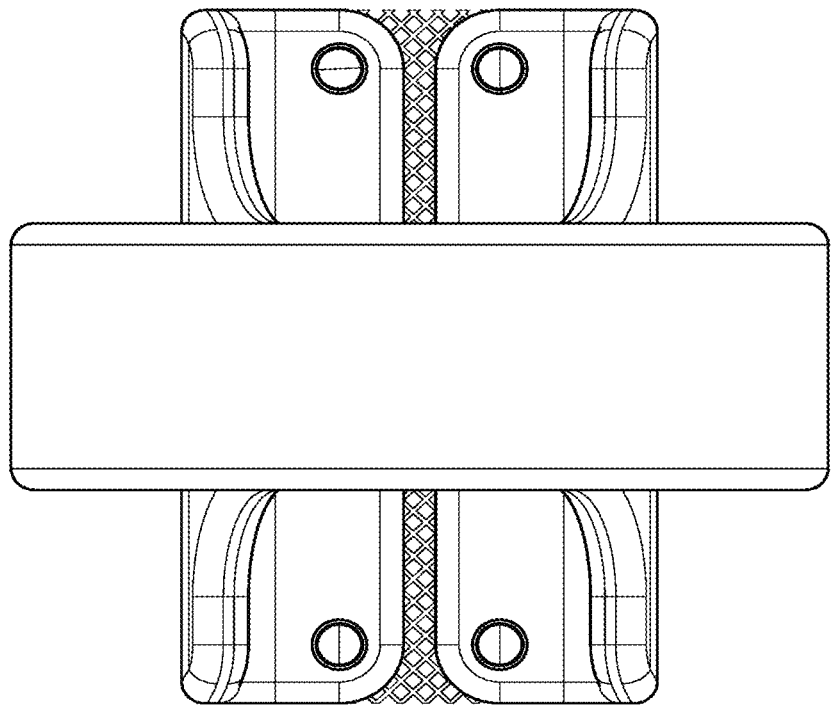
FIG. 16B shows a top view of the applicator of FIG. 16A.
Figure 16D:
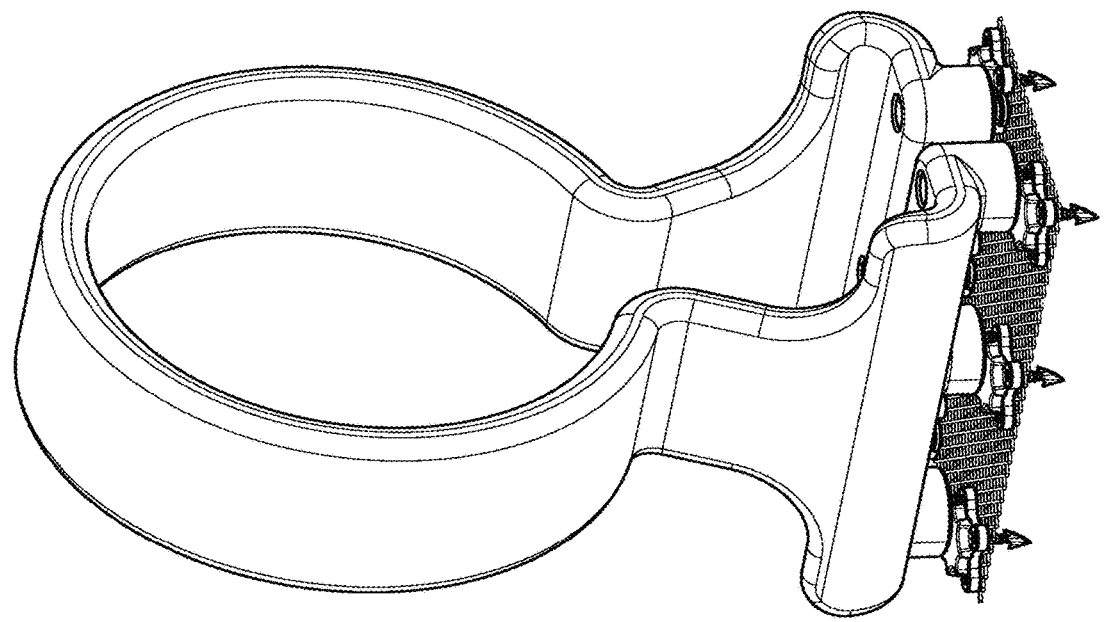
FIG. 16D shows a perspective view of the applicator of FIG. 16A.
Figure 16C:
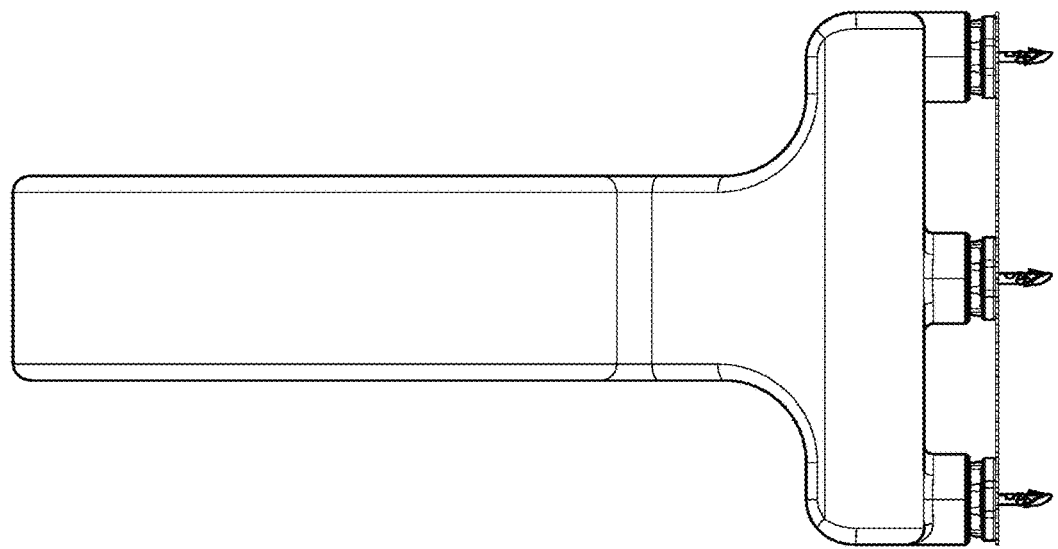
FIG. 16C shows a side view of the applicator of FIG. 16A.

The tensioning arms 1510a and 1510b of the omega applicator 1500 can include protrusions 1511 spaced at locations corresponding to the location of the fasteners 1400 as aligned on the mesh 150. For example, as illustrated by FIGS. 15A-15B, each tension arm (1510a and 1510b) can include three protrusions (e.g., 1511) and, as illustrated by FIG. 16A, each protrusion can align with a fastener of the mesh 150.

Figure 17B:
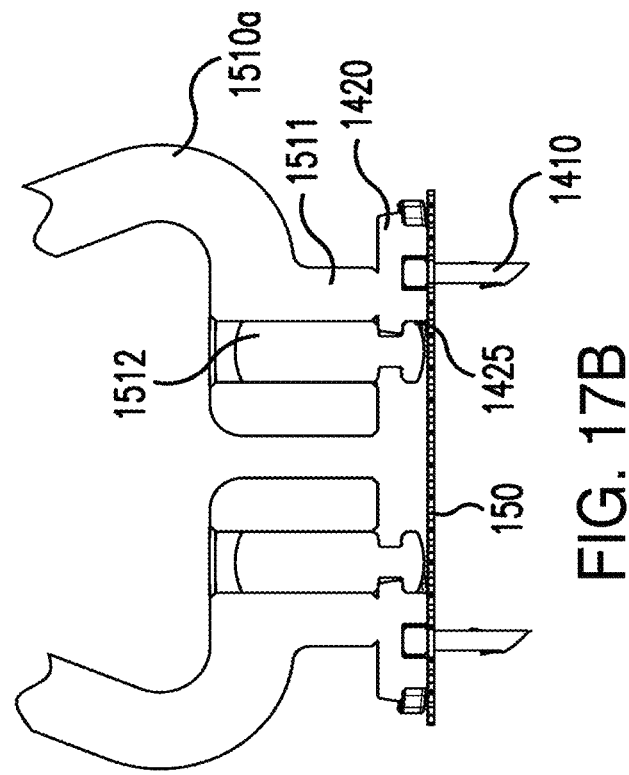
FIG. 17B is a zoomed in view of the mating interface between the applicator and mesh strip of FIG. 17A.
Figure 17A:
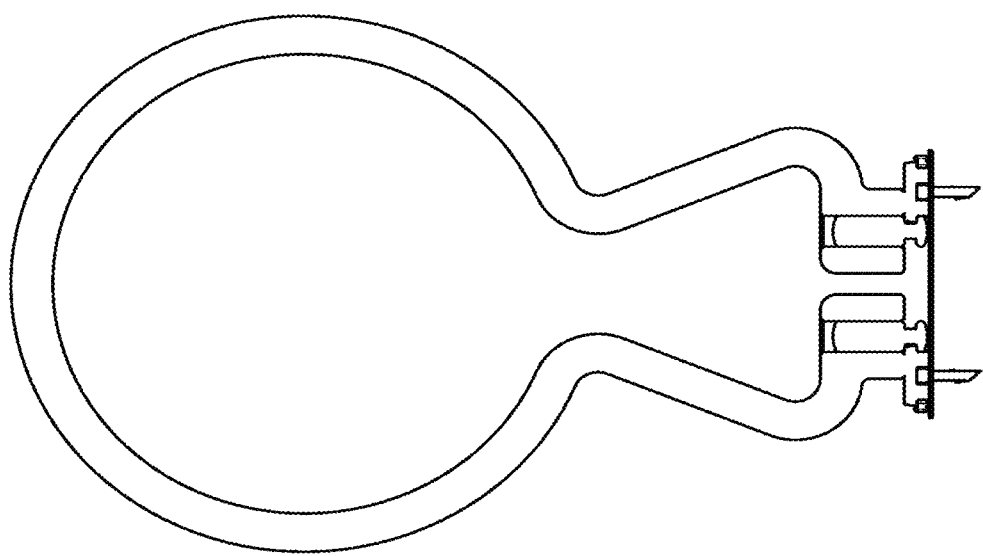
FIG. 17A depicts a cross-sectional view of the applicator of FIG. 16A-D mated with the mesh strip of FIGS. 14A-F in accordance with an exemplary embodiment of the disclosed subject matter.
Figure 18:
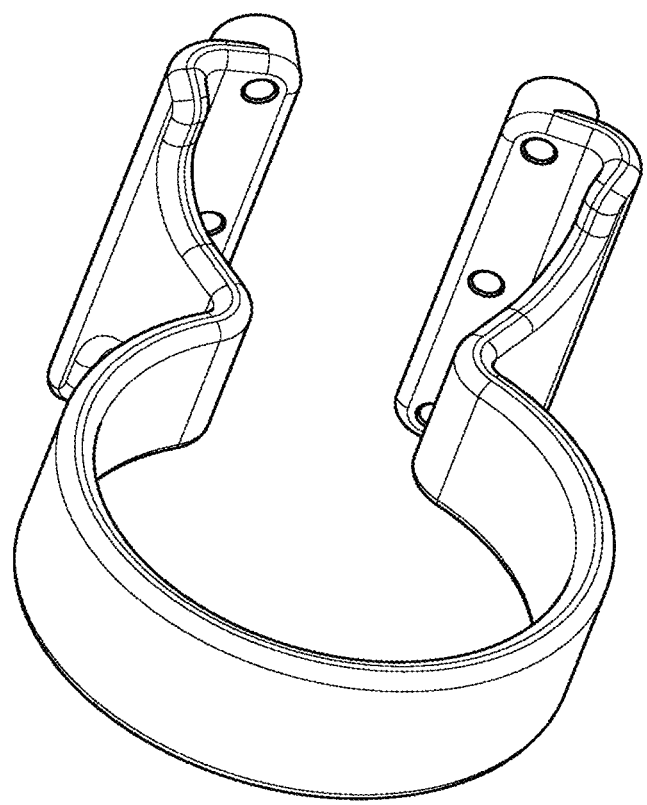
FIG. 18 is an image of an applicator in accordance with an exemplary embodiment of the disclosed subject matter.

Each protrusion 1511 can include a post 1512 for mating with the mating interface 1425 of the fasteners 1400. In accordance with an exemplary embodiment, the posts 1512 can be formed from a different material than the handle and tensioning arms of the applicator. For example, the posts 1512 can be formed from metal and can be received within an opening in the protrusions 1511 of the tensioning arms, as illustrated in FIG. 17B. Alternatively, the posts 1512, tensioning arms 1510a and 1510b, and handle 1540 can be formed from the same material as a single structural unit. Additionally or alternatively, the posts 1512 may be received by the tensioning arms but not permanently affixed. For example, the posts 1512 may be movable to allow for engagement and disengagement with the mating interface 1425 of the fasteners 1400.

FIGS. 16A-16D and 17A-17B illustrate an omega applicator 1500 mated with the integrated mesh strip 150 and fasteners 1400 of FIGS. 14A-14F. Generally, for purpose of illustration and not limitation, the applicator 1500 can first be squeezed into its contracted state (illustrated by FIG. 15B). The protrusions 1511 can be aligned with the fasteners 1400 such that the posts 1512 align with the mating interface 1425 of the fasteners. As illustrated by FIG. 17B, and in connection with an exemplary and non-limiting embodiment, the top portion 1420 of the fasteners 1400 can include an overhand to thereby create a mating interface 1425 for receiving the posts 1512 laterally. For example, the posts 1512 can have a knob shape which is adapted to be received within and under the overhang of the top portion 1425 of the fasteners 1400. The applicator 1500 can then be relaxed, thereby mating the posts 1512 of the tensioning arms 1510a and 1510b to the fasteners 1400 and creating a horizontal tension across the mesh 150b.

In accordance with certain embodiments, the applicator 1500 can be configured such that, once mated to the fasteners and without the application of force (i.e., in a relaxed state), a predetermined amount of horizontal tension be applied to the mesh. For example, and not limitation, the handle 1540 of the applicator 1500 can be formed to achieve a desired spring constant by altering its shape, thickness, and material composition such that when relaxed, the applicator 1500 experts a predetermined tension on the mesh 150 via the tensioning arms 1510a and 1510b.

Moreover, in accordance with certain embodiments, the applicator 1500 can be configured such that, once mated to the fasteners and without the application of force (i.e., in a relaxed state), the angle of the force exerted by each tensioning arm 1510a and 1510b is substantially horizontal. For example, and not limitation, the applicator 1500 can be configured such that the tensioning arms 1510a and 1510b are coupled to the handle 1540 at a predetermined angle such that, when relaxed to the point of mating with the fasteners 1400 the force exerted by the tensioning arms 1510a and 1510b is substantially horizontal (i.e., in the direction of the plane of the mesh 150). The predetermined angle at which the tensioning arms are attached to the handle of the applicator can be determined by a variety of factors, including the dimensions and geometry of the applicator, mesh strip, and distance between the fasteners. For example, one of skill in the art will appreciate that due to the elastic nature of the mesh 150, the mesh 150 will expand upon initially mating with the tensioning arms 1510a and 1510b but eventually stabilize. The angle at which the tension arms are attached to the handle can be determined, for example, with reference to the distance between the fasteners 1400 once the mesh stabilizes under horizontal tension and with reference to the dimensions of the handle 1540.

After the applicator 1500 has been mated with the integrated mesh strip and fasteners, as illustrated by FIGS. 16A-16D, a surgeon can align construct over an incision. The surgeon can then apply a downward force to insert the barbed affixations 1410 into the fascia and thereby affix the mesh construct. For example, and not limitation, the protrusions 1511 can be configured such that when mated with the mesh construct, at least a portion of a protrusion 1511 is aligned over the top portion 1420 of a fastener 1400, such that a downward force to the applicator as a whole can be directed to the fasteners 1400. Once the mesh construct is affixed, the surgeon may again squeeze the handle 1540 of the applicator 1500 to disengage the posts 1512 from the mating interface 1425.

In accordance with certain exemplary embodiments, the omega applicator 1500 can also include an extension arm to allow for affixation of mesh constructs in areas that may be difficult to reach by hand. For example, an extension arm can be disposed at the apex of the handle loop 1540 so that the entire applicator 1500 may be inserted past layers of tissue or fat to reach the fascia. In certain embodiments, the extension arm can be removable for convenience.

In certain embodiments, the system described herein can include a tissue spreader, in addition to the tray, pre-integrated mesh fasteners, and applicator. The tissue spreader can be a square or rectangular shaped tissue spreader, and can be adapted for spreading tissue and soft tissue retraction to neatly expose the fascia surrounding an incision such that the applicator can then be aligned over the incision without obstruction and hand in glove passed through or between the tissue spreader and onto the fascia. Such a system in accordance with the disclosed subject matter can streamline the process of PMA.

For example, pre-integration of mesh strips with fastener-anchors in accordance with the disclosed subject matter couples and streamlines an otherwise time-consuming set of independent intra-operative steps, saving precious and costly operating room minutes. By simplifying the process and structure of PMA, the system provides an effective solution to a complex task while preserving biomechanical benefit. Additionally, the pre-assembled nature of the mesh-anchor system and simple, but effective applicator system, make the process reliable and standardized for surgeons. The disclosed subject matter allows for more widespread adoption of PMA, and can provide for improved or optimized strategy to PMA by leveraging biomechanical principles, feature and task integration, and stream-lined device design dictated by end-user input.

For purpose of illustration, and not limitation, additional embodiments of the mesh strip will be described.

As described herein, the mesh strip is the material that is affixed onto the fascia in a vertical orientation in order to biomechanically augment the anterior abdominal fascia during surgical access to the abdomen. The fasteners are the unidirectional anchors that are attached to the mesh strip in order to serve 2 purposes: (i) to interact with the fascia by penetrating and affixing onto it; and (ii) To interact with the applicator and allow for full control and the ability to quantify the amount of tension being put on the mesh strip.

The mesh strip can include, for example, Phasix mesh or polyprophylene monofilament. One of skill in the art will appreciate that any type of mesh strip can be used, such as, for example and not limitation, those described in V. Shankaran et al., *A Review of Available Prosthetics for Ventral Hernia Repair*, 253 Annals of Surgery 16 (Jan. 2011), which is hereby incorporated by reference in its entirety.

The mesh strip can be cut in a variety of orientations. For example, the mesh strip can be cut in a horizontal configuration, a vertical configuration, or at an angle, such as 45 degrees. The mesh strip can also have a variety of dimensions as desired. In connection with an exemplary embodiment, the mesh strip can be 3 cm×5 cm. Alternatively, the mesh strip can be 3.5 cm×6.5 cm. The number of fasteners on each side of the mesh can also be varied. For example, the mesh strip can have 2 or 3 fasteners per side. As described above, the number of penetrating tacks on each fastener can be varied. For example, in accordance with an exemplary embodiment, the fasteners can have 8 penetrating tacks. In another embodiment, each fastener can have a single penetrating tack.

Figure 6:
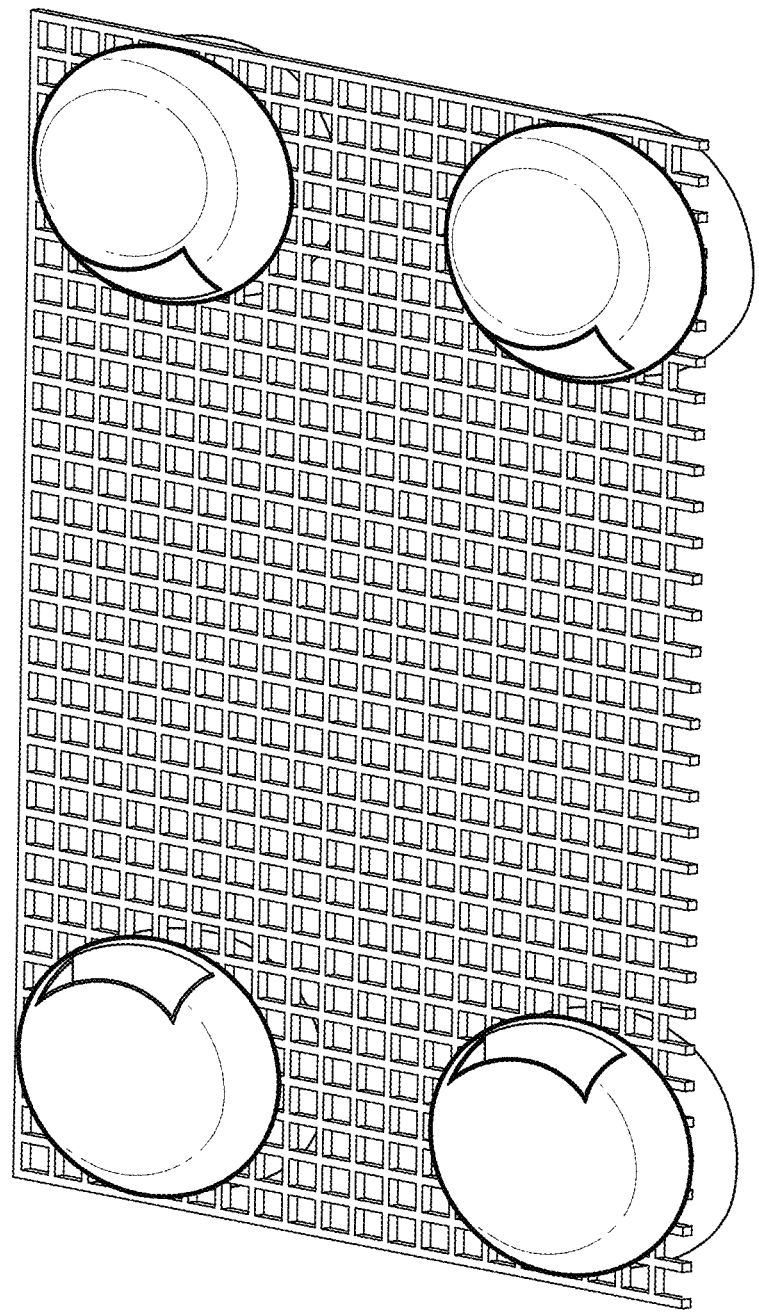
FIG. 6 illustrates a pre-integrated mesh-fastener in accordance with another exemplary embodiment of the disclosed subject matter.

With reference to FIG. 6, which depicts an embodiment of a mesh strip in accordance with the disclosed subject matter, the mesh strip can have a total of 4 fasteners, each one made of two adjoining pieces. The two pieces of this fastener in particular can be attached via a snap-lock mechanism. For example, 4 small (1 mm in diameter) cylindrical protrusions on the top piece can snap into matching holes on the bottom piece. This embodiment can include 4 fasteners to allow attachment of the mesh strip onto the fascia in a horizontal orientation. In connection with this embodiment, the fasteners can have a thick structure (3.5 mm in thickness) to make the fasteners as strong as possible.

With reference to FIG. 7, which depicts another embodiment of a mesh strip in accordance with the disclosed subject matter, the mesh strip can have 4 fasteners that are each made up of two adjoining pieces. However, the two pieces in this embodiment are connected via one large snap lock feature in the center instead of 4 smaller ones. The bottom portion of the fastener can be composed of a main circular hub that is 11 mm in diameter. This hub can be 1 mm thick and it can have a t-shaped center (spoke-like) support for structural stability. Evenly spaced around the bottom circumference of the hub can be 8 tacks with barbs. These tacks can be 1 mm in diameter and can come to a point, so as to penetrate the fascia. The barbs can allow for more reliable affixation, as they catch on to the fascia, anchoring the mesh/fastener assembly. The top portion of the fastener can be t-shaped as well, so as to minimize material, while still maintaining its structural integrity. It can also be 11 mm around its outer diameter and 1 mm thick. Protruding from the top of the post is a cylinder to allow for engagement with the applicator and therefore allow stretching of the mesh. The cylinder can act as a post, as it is the main feature that allows for the mesh to be supported in the applicator. It can protrude out 1.5 mm high.

FIG. 8 depicts another embodiment of a mesh strip in accordance with the disclosed subject matter. The embodiment depicted in FIG. 8 is similar to the embodiment depicted in FIG. 7, except that the fasteners in this embodiment have 4 penetrating tacks instead of 8 and the two pieces of the fasteners are adjoined on the top part of the fastener instead of on the bottom. The pieces are adjoined at the top in order to prevent having an added layer of material between the mesh and the fascia when the mesh strip is affixed.

Figure 9:
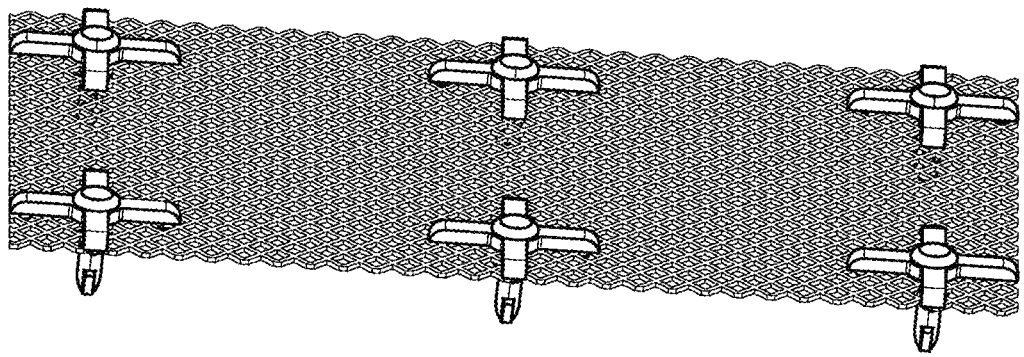
FIG. 9 illustrates a pre-integrated mesh-fastener in accordance with another exemplary embodiment of the disclosed subject matter.

FIG. 9 depicts another embodiment of a mesh strip in accordance with the disclosed subject matter. This embodiment can be suitable for attachment to the fascia in a vertical orientation. Attaching in a vertical orientation can allow for the use of only 2 strips for the average incision, instead of the 3 that would be necessary if the strips were attached horizontally. This can conserve the amount of mesh needed for each procedure, and reduces the time needed to complete the procedure. Because the strip is to be attached vertically, the dimensions can be selected to accommodate for the average incision length. The length of the strip depicted in FIG. 9 is 65 mm and the width is 35 mm. Because the mesh strip of FIG. 9 is longer, one more fastener is can be per side, bringing the total number of fasteners up to 6. This can reduce the "bowing" effect that can occur in the middle of the strip as it is stretched. The mesh strip of FIG. 9 was cut at a 45-degree angle instead of cut horizontally. Cutting at a 45-degree angle can change the stretching characteristics of the mesh. Cutting at this angle can give the mesh a higher stiffness, making it so that it is more difficult to stretch the piece of mesh. The team is currently running tests in order to further quantify the mechanical characteristics of the mesh in this and other orientations. The embodiment of FIG. 9 utilizes one tack.

Figure 10:
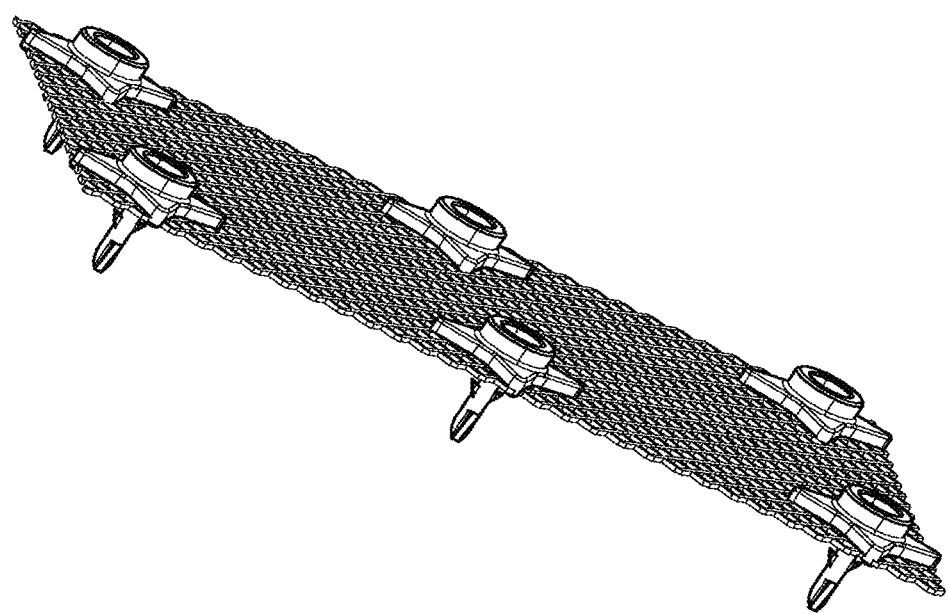
FIG. 10 illustrates a pre-integrated mesh-fastener in accordance with another exemplary embodiment of the disclosed subject matter.

FIG. 10 depicts another embodiment of a mesh strip in accordance with the disclosed subject matter. This embodiment includes 2 pieces that adjoin together. The top piece can be injection molded, while the tack piece can be either molded or machined. The two pieces can be glued together. The fasteners in this embodiment can engage with the applicator via a 2 mm deep hole on the top. This embodiment also a mesh with the 3.5 cm×6.5 cm dimensions. Because of this, there are 3 fasteners per side so as to avoid bowing in when tensioned. The 45-degree orientation of the mesh can increase its stiffness and therefore requires more force to stretch.

FIGS. 14A-14F depict another embodiment of a mesh strip in accordance with the disclosed subject matter. This embodiment can provide an improved engagement mechanism with the applicator. By using a side engagement, where a pin on the applicator arms slide into the lip on each of the 6 fastener, there can be enough secure contact between the two to adequately secure the mesh strip onto the applicator. The fastener of the embodiment depicted in FIGS. 14A-14F can be comprised of 3 separate pieces. The top two pieces that create the lip for engagement can be attached via a snap-lock feature and can be strengthened with glue. The third piece is the tack component that can be machined or injection molded and would be attached by gluing into cavity on bottom side of fastener.

Figure 24A:
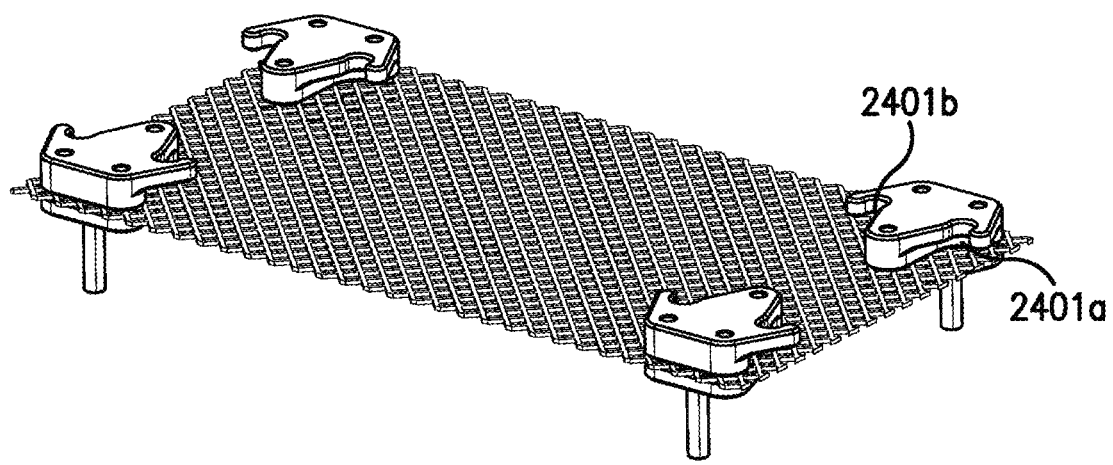
FIG. 24A illustrates a pre-integrated mesh-fastener in accordance with another exemplary embodiment of the disclosed subject matter.
Figure 24B:
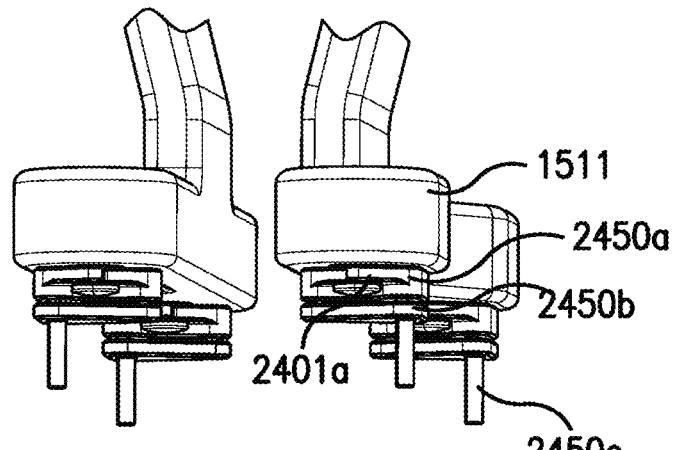
FIG. 24B illustrates the pre-integrated mesh-fastener of FIG. 24A mated with an applicator in accordance with the disclosed subject matter.
Figure 24C:
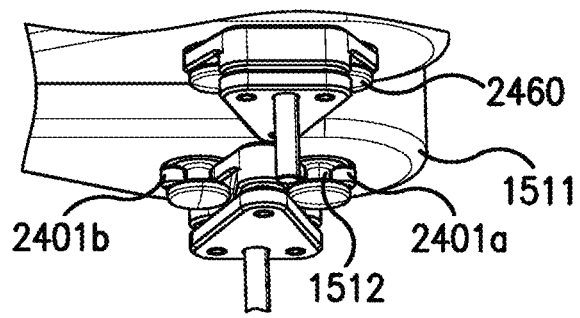
FIG. 24C is a close-up bottom perspective view of the mating interface of FIG. 24B.

FIGS. 24A-24C depict another embodiment of a mesh strip in accordance with the disclosed subject matter. The fastener of the embodiment depicted in FIGS. 24A-24C can provide another means of engaging with the applicator. In this embodiment, each fastener can have two lips (2401*a*, 2401*b*), one on each side. Two pins (e.g., 1512) on the applicator can slide under the lips (2401*a*, 2401*b*) of the fasteners, securely engaging with them, giving the applicator and therefore the user full control of the fasteners and mesh strip. This embodiment can be suitable for use with biodegradable phasix mesh, which can be thicker and has smaller pores than the polypropylene mesh. The fasteners in this embodiment can be comprised of 3 separate pieces (2450*a*, 2450*b*, 2450*c*). The top two pieces (2450*a*, 2450*b*) can be connected with micro-pins (2460) that fit through the small pore size of the phasix mesh. The tack piece (2450*c*) can be attached by gluing into cavity on bottom side of fastener.

The disclosed subject matter is not intended to be limited to the specific embodiments of the mesh strips explicitly described herein. One of skill in the art will understand that a variety of configurations and modifications are contemplated by the foregoing disclosure. For example, the anchor portion of the fastener-anchors can include any number of barbed affixations of a variety of sizes suitable for insertion into the fascia. For purpose of illustration, and not limitation, the anchors can be between 1 mm and 1 cm. In certain embodiments, longer anchors can be used, for example, for diagonal insertion into the fascia. Additionally and/or alternatively, a fastener a plurality of shorter anchors, including anchors less than 1 mm, can allow for affixation in a manner akin to velcro. Additionally or alternatively, the anchors can be curved.

Figure 28:
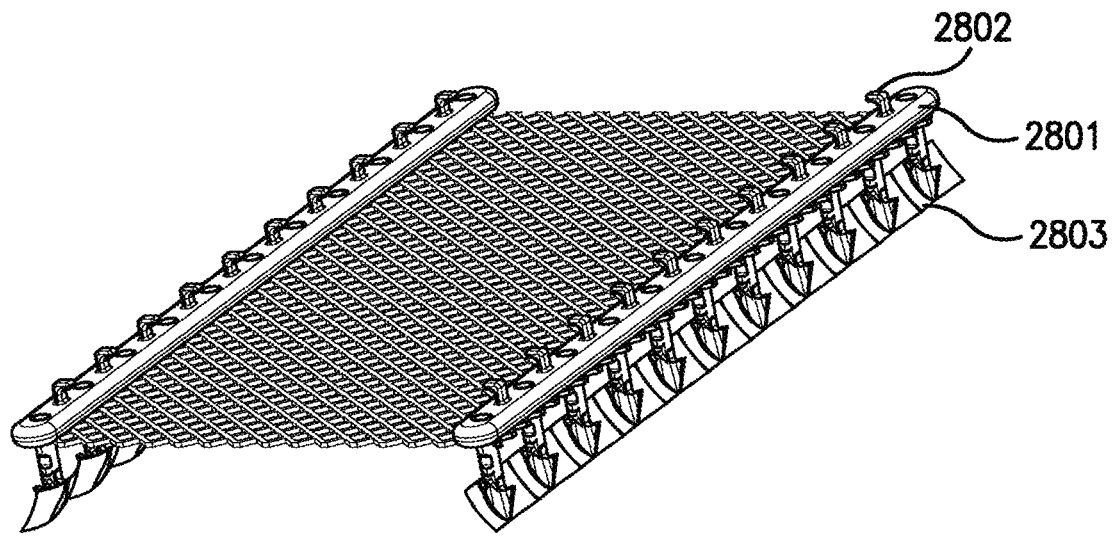
FIG. 28 depicts a mesh strip integrated with fastener anchors in accordance with another embodiment of the disclosed subject matter.

In accordance with another aspect of the disclosed subject matter, the fastener anchors can be mechanically coupled to one another along a side edge of the mesh. For example, with reference to FIG. 28, the fastener anchor mechanisms can be bridged across the edge of the mesh. Although depicted in FIG. 28 as a single strut 2801, a plurality of separate fasteners 2802 and/or the anchors 2803 can alternatively be connected using separate connectors, snaps, glue, or the like. The strut concept can provide a connection between the anchors 2803 in which the strut system can allow for placement of multiple smaller anchors while reducing the amount of material required and can also facilitate uniform stretching of a longer piece of mesh. In connection with this embodiment, the fastener anchor mechanism can engage in complementary fashion with an interface of the applicator that binds to and engages with the strut mechanism. In certain embodiments, these struts can have smaller anchors in them as well to further enhance affixation to the fascia.

Additionally, in accordance with certain embodiments, the strut system can be pre-integrated into the most lateral portion of the mesh and then the mesh can be trimmed to fit. Application of the mesh can then occur with an applicator that has a complementary strut that meets with the mesh anchor strut allowing it to be engaged and tensioned and applied. Additionally other embodiments can include a mechanism whereby removable attachments on either side of the mesh construct which are attached via the anchor strut mechanism can allow hand or manual application followed by hand or manual tensioning and application of the other side.

In accordance with certain embodiments, a plurality of mesh strips can be used to augment or reinforce an incision. For example, for longer fascial incisions, two or more mesh strips can be affixed adjacent each other along the length of the incision. In connection with these embodiments, the fasteners can be integrated into the mesh strips such that the strips can be affixed in sequence. For example, and not limitation, fasteners can be integrated on one edge of a first mesh strip such that a predetermined amount of excess mesh extends beyond the fasteners. In this manner, fasteners on an edge of a second mesh strip can be inserted into the loops of the excess mesh such that the first and second mesh strips overlap. Alternatively, the fasteners on opposite sides of the mesh strips can be arranged at positions that do not overlap to allow for application of a plurality of overlapping mesh strips in sequence. For example, the fasteners integrated at a first side of the strips can be positioned toward the edge of the strip and the fasteners integrated at the second side of the strips can be toward the center of the strip. In this manner, the first and second sides of a plurality of mesh strips may be affixed so as to overlap in sequence.

Figure 30A:
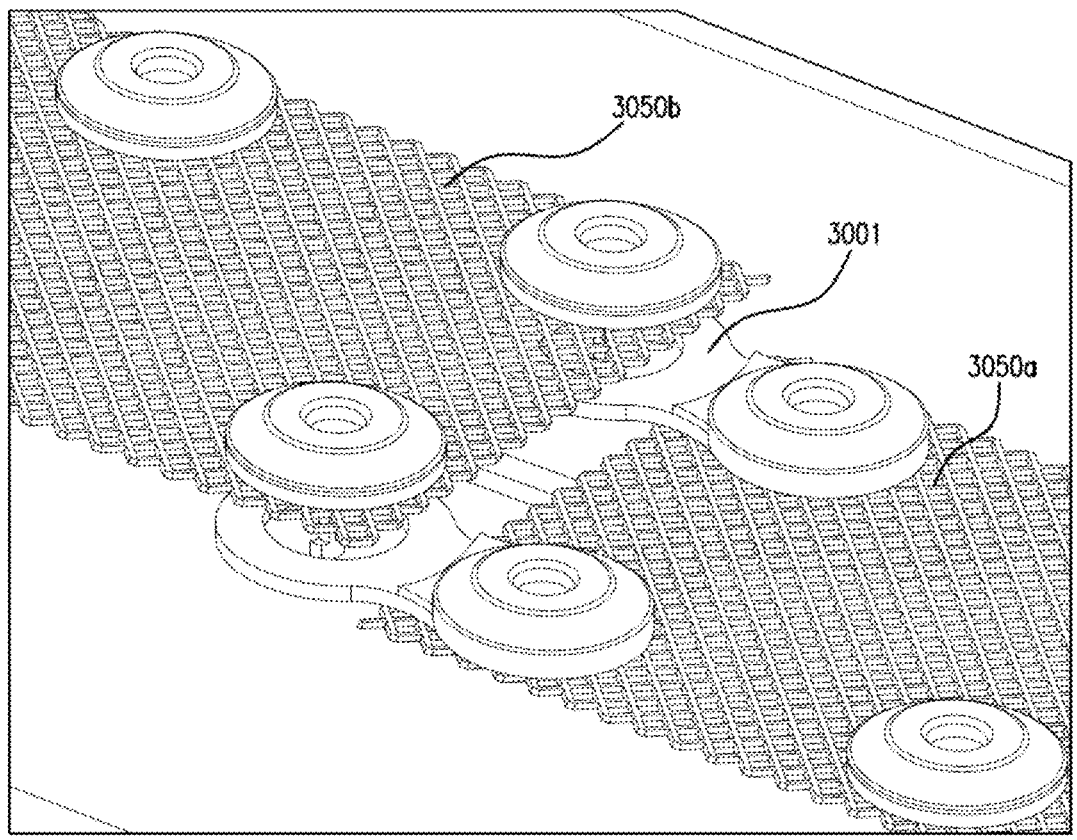
FIG. 30A depicts fastener extenders for sequentially affixing mesh strips in accordance with an embodiment of the disclosed subject matter.

In accordance with certain embodiments, with reference to FIG. 30A two or more mesh strips (3050*a*, 3050*b*) can be sequentially affixed to one another using fastener extenders (e.g., 3001). For example, and not limitation, to allow for the surgeon operator to place consecutive mesh strips (3050*a*,

3050b), the most distal or proximal portion of the mesh strip 3050b can have a fastener that has an extender 3001 and target for subsequent consecutive mesh strip placement. In this manner, the faster anchor of the subsequent mesh strip 3050a can be applied through the faster anchor extended 3001 of the other previously affixed mesh construct 3050b to allow for seamless intraoperative connecting of strips and to prevent weakness associated with placement of non-connected adjacent strips.

Figure 30B:
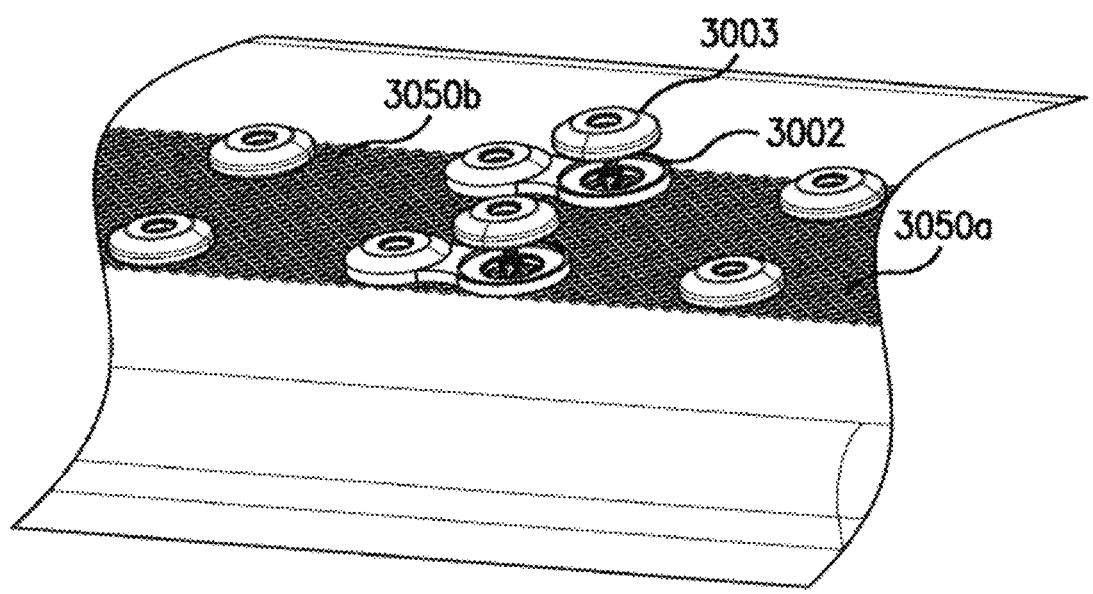
FIG. 30B depicts fastener extenders for sequentially affixing mesh strips in accordance with another embodiment of the disclosed subject matter.

Alternatively, in connection with certain embodiments and with reference to FIG. 30B, two or more mesh strips (3050a, 3050b) can be sequentially affixed to one another using fastener extenders (e.g., 3002). For example, and not limitation, the most distal or proximal portion of a first mesh strip 3050b can have a mesh region without integrated fasteners. A second mesh strip 3050a can include at its most distal or proximal edge a fastener extender 3002 which can be aligned over the mesh strip 3050b after mesh strip 3050b has been affixed, and can include a target for subsequent insertion of fastener anchor 3003.

For purpose of illustration, and not limitation, additional embodiments of the applicator will be described.

The applicator is the component of the system that facilitates the tensioning process. The applicator can have arms that securely engage with the fasteners on the mesh strip, giving the user full control of the mesh strip and allowing him/her to tension the strip to the desired amount. The applicator can serve at least the following purposes: (i) securely engage with the fasteners; (ii) provide information about the amount of tension being applied to the mesh strip; and (iii) indicate optimal amount of tension.

The applicator can be formed from various materials, including metal or plastic (ABS), and disposable or non-disposable composite material. The applicator, as disclosed herein, can be designed to engage the fasteners on the side or on the top. The applicator, as disclosed herein, can have a variety of grip styles. For example, the applicator can have a scissor-like grip, an "omega" style grip, or a pistol grip. Further, the omega style grip can be disposed to be either opened or closed in a resting state.

FIGS. 2A-2C depict an embodiment of an applicator in accordance with the disclosed subject matter. This embodiment of the applicator can use the Kolbel Soft Tissue Weitlaner as the base structure can be modified to fit the specific requirements of the applicator. The prongs can be grinded off of the weitlaner and sleeves can be fit onto the arms of the weitlaner. Each sleeve can have two slots and the distance between the slots can corresponded to the distance between the centers of the fasteners in order to allow for the knobs of each of the fasteners to slide into the slots. The sleeves can be 3D printed out of ABS. The weitlaner includes two interlocking arms, when the handles are squeezed, the arms separate. This mechanism is what facilitates the tensioning of the mesh. After the knobs on the mesh strip fasteners are slid into the slots on the custom designed sleeves, squeezing the weitlaner moves the fasteners away from each other and as a result, the mesh strip would be tensioned.

FIGS. 15A-18 depict another embodiment of an applicator in accordance with the disclosed subject matter. This embodiment has an "omega" style grip. This embodiment provides another method of engagement with the fasteners and can be less obstructive of the incision line. The normally-opened device is shaped like the Greek letter omega, with an arch/parabolic shaped top leading down to two opened arms. The distance between these arms can be determined by the amount of stretch/tension that is desired.

Since the fasteners on opposing sides of the mesh strip are nominally 24 mm apart when the mesh is unstretched, in order to achieve 4 mm of stretch, the nominal distance between the 2 arms on the omega can be 28 mm. The omega applicator can be made of ABS plastic. The flexibility of the ABS plastic makes it so that when one squeezed the normally-opened applicator, the arms to deflect inward, closing the gap between the two arms. When released, the elastic properties of the ABS plastic allow for the arms to return to the nominal 28 mm separation. This spring-like elasticity is what creates the force needed to tension the mesh. This system also allows for controlled and reproducible device-mediated mesh tensioning and subsequent application.

In order to engage with the fastener/mesh strip system, the user simply has to squeeze the omega so that the arms fit in between the fasteners and align the arms with the lips on the fasteners. On the bottom side of the arms of the omega are the pins that interact with the fasteners. Each fastener can interact with two pins, one on each side, in order to prevent tipping of the fasteners. For example, with 4 fasteners on the mesh strip, there can be a total of 8 pins on the omega. Each pin can have a head of slightly larger diameter. This head can fit into an overhang on the fasteners, allowing for both easy and secure engagement. After tensioning and affixing the mesh, by squeezing the applicator again, the heads on the pins slide out of the overhang on the fasteners allowing for an easy disengagement as well.

Figure 25:
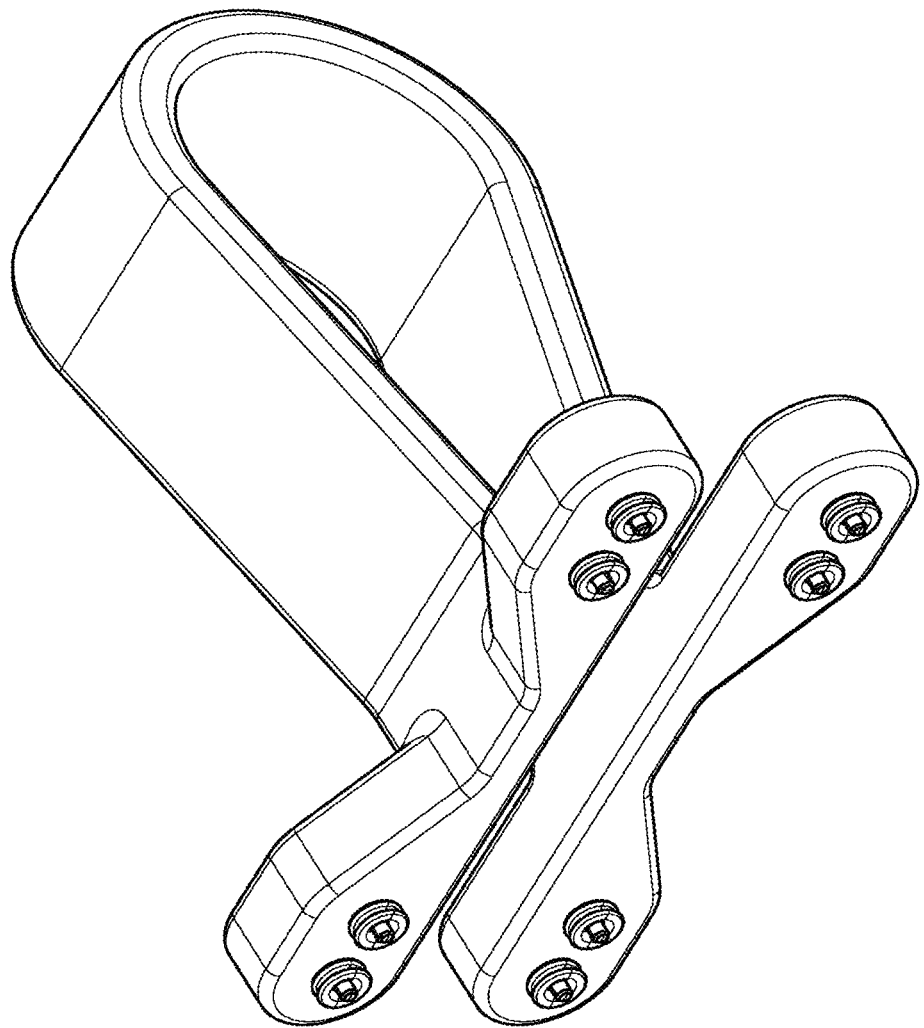
FIG. 25 depicts an embodiment of an applicator in accordance with the disclosed subject matter.
Figure 26A:
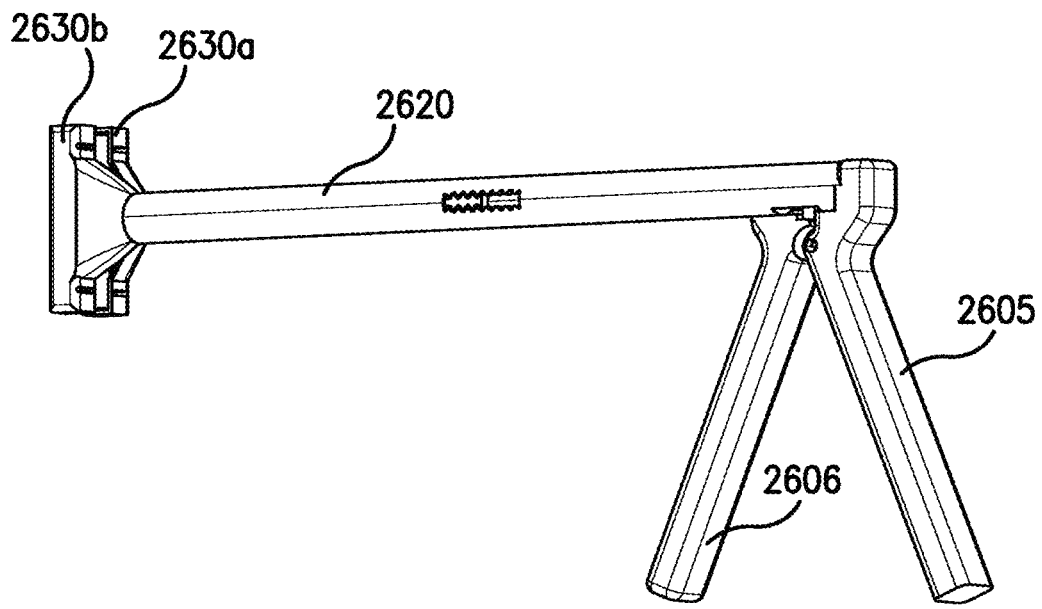
FIG. 26A depicts a pan view of an embodiment of an applicator in accordance with the disclosed subject matter.
Figure 26B:
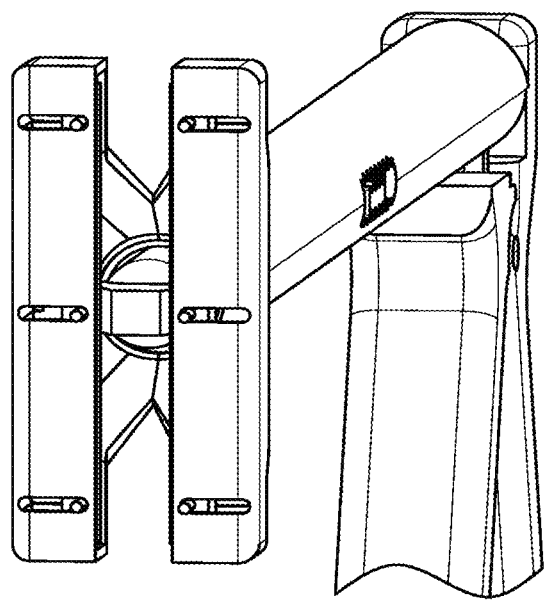
FIG. 26B depicts a view of the tensioning arms of the applicator of FIG. 26A.
Figure 26C:
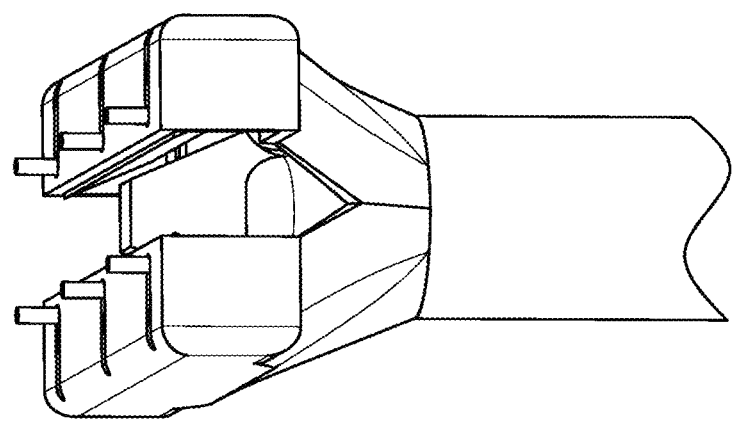
FIG. 26C depicts a close-up of the tensioning arms of the applicator of FIG. 26A.
Figure 26D:
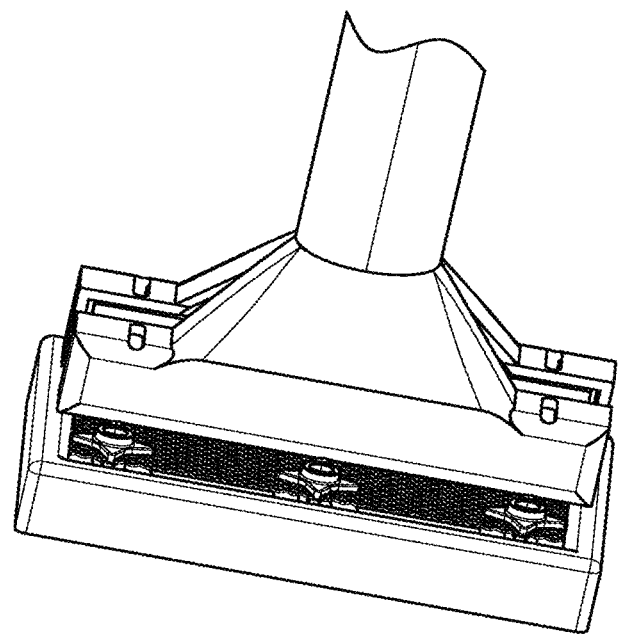
FIG. 26D depicts the applicator of FIG. 26A mated with a mesh strip in accordance with the disclosed subject matter.

FIG. 25 depicts another embodiment of an applicator in accordance with the disclosed subject matter. This embodiment is similar to the embodiment depicted in FIGS. 15A-18. However, this embodiment can have a smaller frame in order to minimize how much of the user's view is obstructed during use. Each arm can have a divot in order to allow for a better view of the work area when approaching the incision line. In addition to this, this embodiment has two pins per fastener and can engage with only 4 fasteners.

Although the embodiments of FIGS. 24A-24C and FIG. 25 depict an "omega" style applicator having an open resting state, other embodiments can include an applicator having a normally closed resting state. For example, and not limitation, the normally-closed applicator can open its arms as it is squeezed while the normally-opened omega closes its arms when squeezed. Further, in certain embodiments, the applicator can include a ratchet mechanism that can be calibrated to show the amount of tension that is being put on the mesh strip with each increment of the ratchet mechanism. That is, for example, the ratchet can be calibrated with respect to force vs. displacement data obtained by sampling such that each "click" on the ratchet corresponds to a defined incremental increase in tension. The ratchet mechanism can also have a meter on it to show the user how much tension each "click" corresponds to and therefore how much tension is exerted on the mesh.

FIGS. 26A-26D depict another embodiment of an applicator in accordance with the disclosed subject matter. The applicator of this embodiment can include a pistol grip 2605 and trigger 2606 to allow the user to tension the mesh. This applicator can also include a long shaft 2620 to allow fitting the device through soft tissue or fat retractor. This embodiment can include a trigger 2606 mechanism that when squeezed pushes an inner shaft forward. At the front end of the inner shaft is a wedge 2607 that fits in between the mating wedges (2608a, 2608b) in the front casing (2630a, 2630b). These mating wedges (2608a, 2608b) contain the pins (2609a, 2609b) that engage with the holes on the fasteners. After the pins are inserted into the holes, squeezing the trigger 2606 stretches and tensions the mesh strip.

For purpose of illustration, and not limitation, additional embodiments of the mesh tray will be described.

The mesh tray can standardize and simplify the process of docking the applicator onto the fasteners on the mesh strip. The tray can be configured such that the fasteners are always in the correct orientation to allow for correct and adequate engagement with the applicator. In order to obtain even tension throughout the mesh, the fasteners can be placed in their predefined, evenly spaces locations. The mesh tray can (i) contain the fasteners in their predefined locations in order to facilitate even tensioning; and (ii) assist in attaching the fasteners to the mesh strip.

FIGS. 13A-13C depict a mesh tray in accordance with an exemplary embodiment of the disclosed subject matter. This embodiment can allow for tensioning to occur within the tray itself. By allowing the tensioning to happen in the tray, another level of security can be added in terms of the fasteners being aligned securely. This embodiment also allows for both the docking and tensioning steps to happen sequentially, which reduces variability caused by slippage of the engagement if the mesh were to be pulled out before being tensioned. The embodiment depicted in FIGS. 13A-13C can be used, for example, with the mesh strip with 6 fasteners depicted in FIG. 10.

Figure 27:
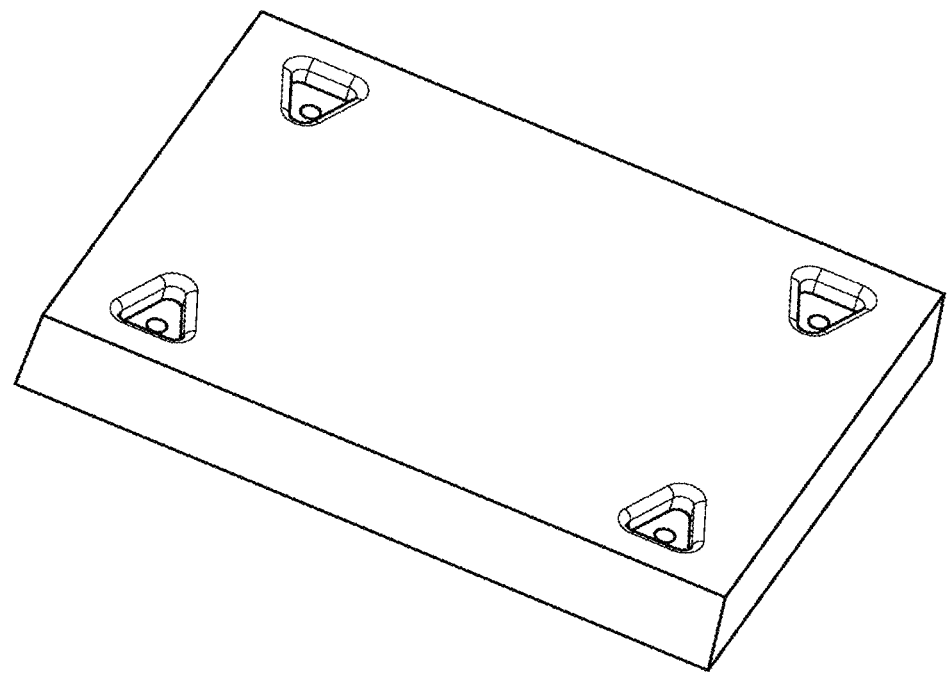
FIG. 27 depicts an embodiment of a mesh tray in accordance with the disclosed subject matter.

FIG. 27 depicts another embodiment of a mesh tray in accordance with the disclosed subject matter. This embodiment can interface with the mesh strip of the embodiment depicted in FIGS. 24A-24C. The geometry of the fastener cavities can correspond to the dimensions of the fasteners of embodiment FIGS. 24A-24C.

Figure 31A:
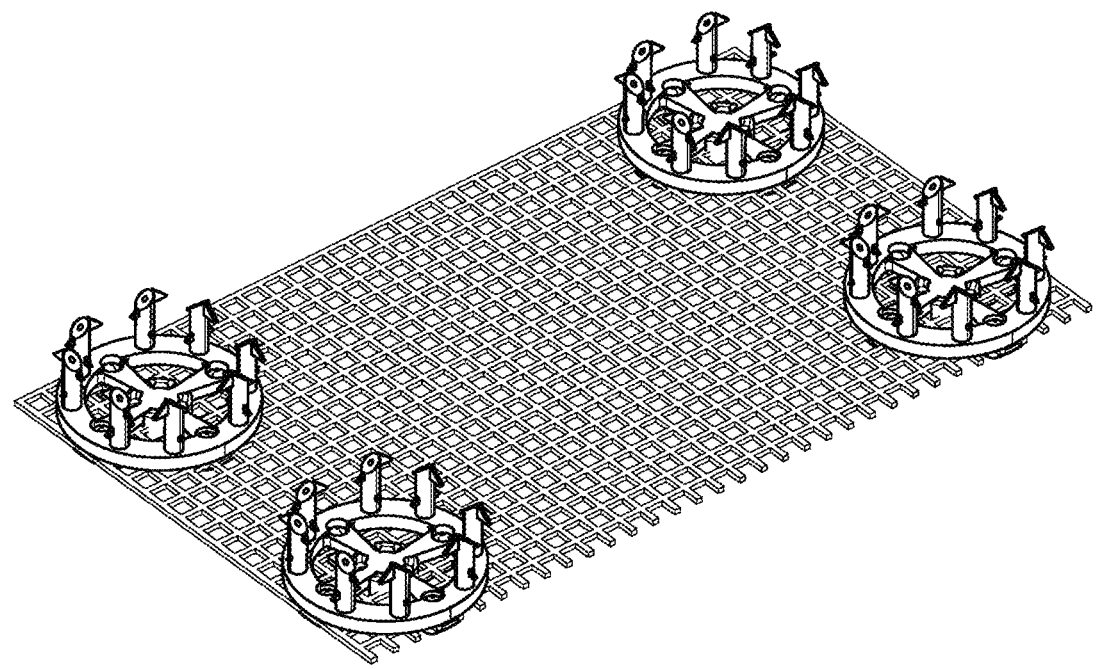
FIGS. 31A and 31B depict a device for inserting and integrating fastener anchors into a mesh strip in accordance with an embodiment of the disclosed subject matter.
Figure 31B:
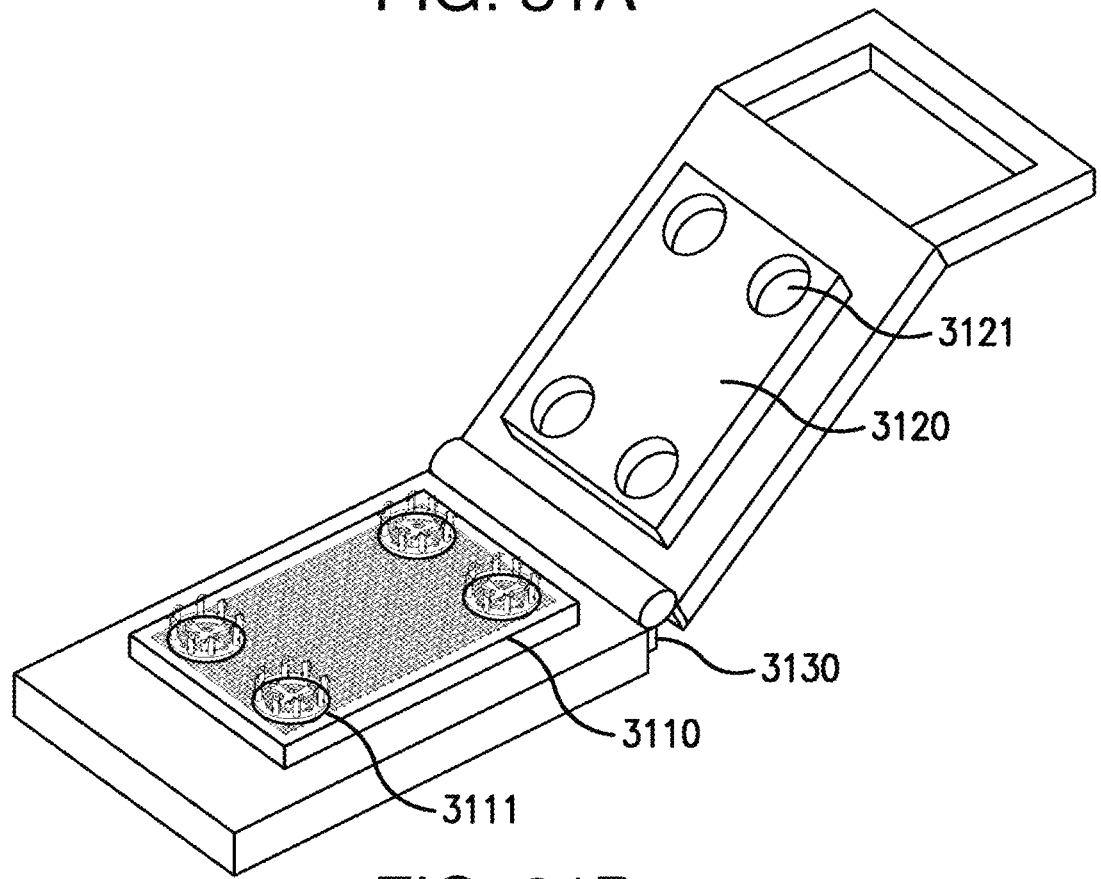

In accordance with another aspect of the disclosed subject matter, a system for integrating fastener anchors into a mesh strip is disclosed. In connection with an exemplary embodiment, with reference to FIGS. 31A and 31B, a device for integrating fastener anchors can include an lower portion 3110 and an upper portion 3120 connected by a hinge 3130. The upper and lower portion can include a plurality of wells or constructs adapted to hold the pieces of the fastener anchors. For example, the lower portion 3110 can include structural feature 3111 which can be adapted to hold the fastener portion of the fastener, such as described above with reference to FIGS. 4A-4D, and the top portion 3120 can include structural feature 3121 which can be adapted to hold the bottom portion of the fastener.

In connection with an exemplary embodiment, a mesh strip can be positioned in between the top portion 3120 and bottom portion 3110 containing the top and bottom pieces of the fasteners, respectively. The upper portion 3120 can rotate about the hinge such that the structural elements 3111 and 3121 align and the top and bottom pieces of the fastener can be integrated, e.g., by a snap lock feature, with each other with the mesh in between, thereby integrating the fasteners into the mesh.

Another aspect of the disclosed subject matter relates to a system and device to automatically and rapidly affix as on an onlay technique a mesh on any defect of the abdominal wall where there is an opportunity to place an onlay mesh inclusive of hernia repairs. The device can be composed of a component that will hold a roll of mesh and a chamber or reservoir with tacks. Once the fascial incision or anterior fascia has been secured with sutures the device can be used to lay the mesh on top of it and fastened to the surrounding fascia with tacks. The device can work by unrolling the mesh over the sutured incision and fastening to the sides with tacks simultaneously. The device and affixed mesh share the load of the sutures to prevent the sutured site from weakening and leading to a hernia. The disclosed subject matter relates to an automated, disposable, electromechanical mesh affixation system capable of precisely affixing various mesh types to a primarily closed laparotomy incision or any fascial incision of the abdominal wall.

Further details regarding three features of an embodiment of the disclosed subject matter follow.

Mesh: the mesh can be used as an onlay to reinforce any fascial wound amenable to onlay mesh augmentation, for example a primary (sutured) midline laparotomy incision. It can be relatively small and designed to be custom fit to the length of the incision and overall be small in width. It can be set under tension using the device to unload the fascia. A variety of mesh types can be available, including various sizes and types. For example, any type of mesh can be suitable including permanent/synthetic, biologic mesh of any kind, vicryl (fast absorbing), and slow absorbing, or any hybrid mesh. The mesh can come in a spool and case which would have a very small width (2-3 cm) compared to prior art meshes (which are typically approximately 10 cm).

Tacking system: the device can accept or be pre-assembled a cartridge or reservoir of slow-absorbing, loading sharing tackers (e.g., curved) or tacks of any kind which recruit and medialize lateral abdominal wall and the mesh to allow for decreased tension across the primary suture repair of the abdomen. Other tacks can also be used, such as spiral tacks and unidirectional tacks.

Device: the device can be a hand-held, disposable mesh affixing apparatus. The device can accept spools of pre-rolled mesh, of which different sizes (widths and lengths) and types (biologic, slow-absorbing, and permanent) can be available. The device also can use disposable cartridges of tacking elements to affix the mesh (e.g., curved, tension sharing). The device can be tension setting such the primary repair is unloaded and thus the mesh serves as a load-sharing measure. To use the device, a mesh and tacks can be selected and the device can be placed on the fascia and covering the primary repair. The mesh can be engaged to the fascia with the press of a button (deploying tacks) and the mesh can be advanced a set distance with a user initial hand squeeze with or without more tacks.

Figure 19:
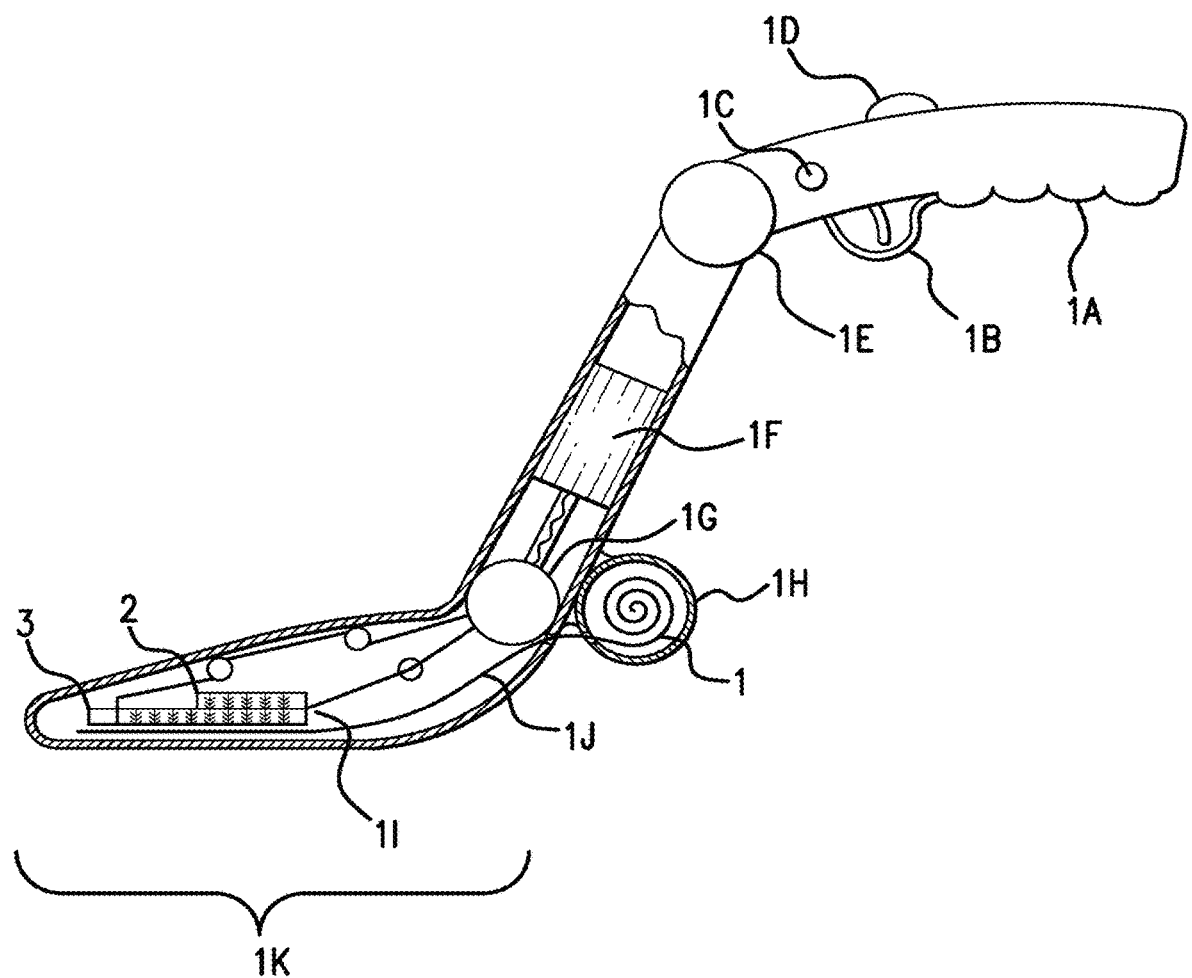
FIG. 19 is a side view of a mesh affixation system according to an embodiment of the disclosed subject matter.

FIG. 19 shows a mesh affixation system in accordance with an embodiment of the disclosed subject matter. The system can be made of medical grade, composite plastic and metal with ergonomic features suitable for hand-held intra-operative use. The system can include an ergonomic handle (1A). The handle can include several features, such as a safety-protected trigger for mesh cutting and termination (1B), a safety switch (1C), an electromechanical device activation button for mesh stretching, tacking, and advancement (1D), and an articulating hinge for improved or optimal 3-dimensional orientation and effacement with fascia to precise apply technique (1E).

The system can include a device chamber (1F) where the electromechanical apparatus that mediates mesh stretch via lateral displacement arms and device affixation through the tack driving system (see FIG. 20B) and mesh advancement motor (1G) can reside. The mesh can also be stretched by other means, such as mesh grasp and pull, or progression internal mesh displacement.

The system can also include a mesh reservoir (1H) in which the mesh is housed. The system can feature two mesh displacement apparatuses (1I and 1J) through which electromechanical or mechanical force can be transmitted resulting in controlled and standardized mesh displacement. Within these displacement arms can be pre-loaded tacking components with a spring-loaded advancement function for synchronized deployment. Mesh displacement and stretch can be generated via electromechanically mediated activation of the arms within the device with activation causing lateral displacement of arms and stretching of mesh by approximately 2-3 mm on each side (see FIG. 20B). The mesh can be advanced into the affixation apparatus, displaced and simultaneous tacked to the abdominal wall by an electromechanical tack delivery system (see FIG. 20B).

Figures 20A, 20B:
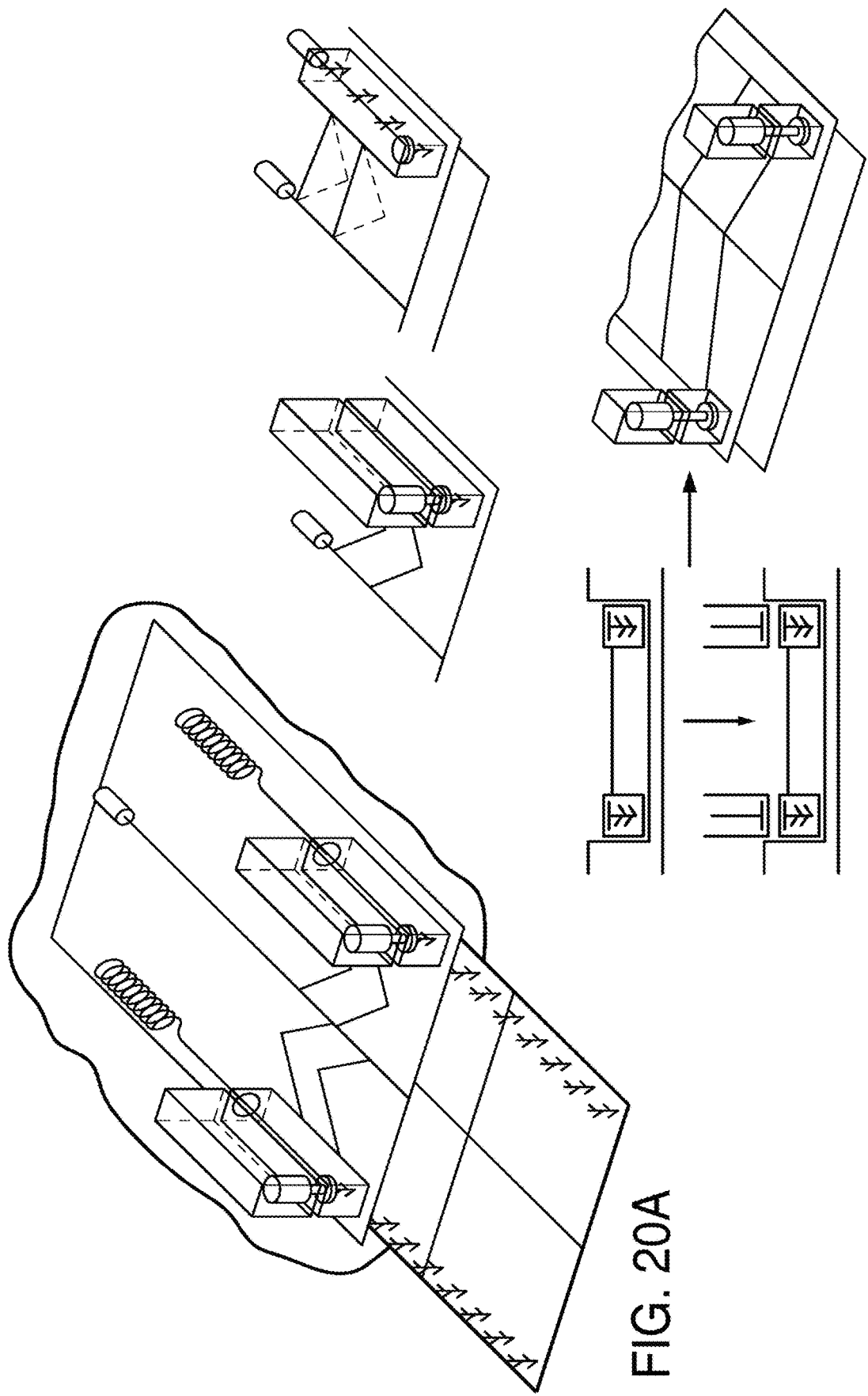
FIGS. 20A and 20B show an overview of the system of FIG. 19.

FIG. 20A shows an overview of the system of FIG. 19. FIG. 20B shows a demonstration of the mesh activation and displacement using the system of FIG. 19. FIG. 20B shows further details about the mesh stretching and tacking system of FIG. 19.

Figure 21:
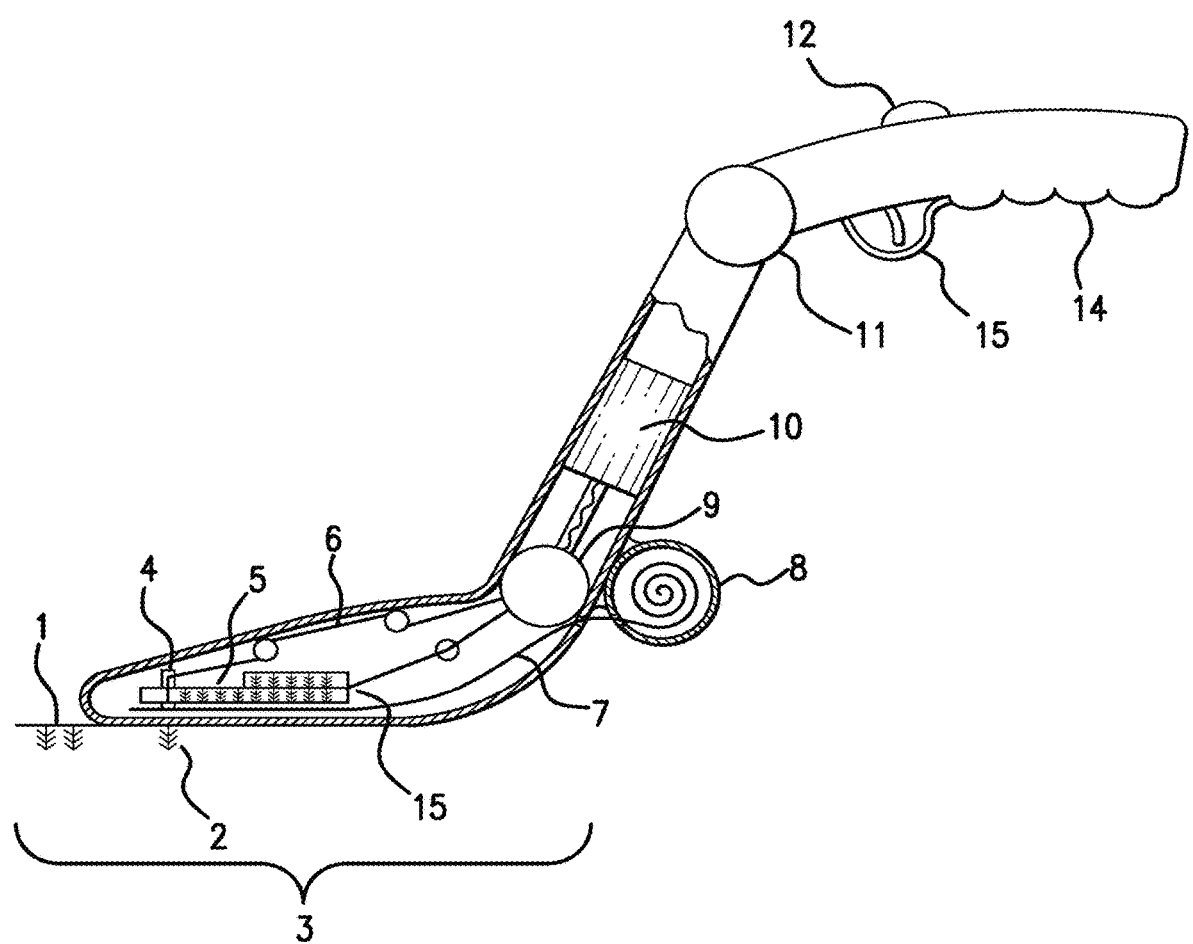
FIG. 21 is a side view of a mesh affixation system according to an embodiment of the disclosed subject matter.

FIG. 21 shows a mesh affixation system in accordance with another embodiment of the disclosed subject matter. The system can include a mesh termination trigger (13) and handle (14). The handle can include a device activation switch (12). An articulating arm (11) can be connected to the handle which can facilitate alteration of pitch. The system can include a motor and electronics board (10) for controlling advancement of the mesh. A mesh advancement wheel (9) can be included to communicate with the motor.

The system can also include a mesh reservoir (8) for storing mesh (7). The system can include a synchronized electromechanical apparatus (6) for coordinating mesh advancement and tacking/stretching. A mesh stretching apparatus (5) can communicate with the synchronized apparatus (6). The mesh stretching apparatus (5) can act to laterally displace mesh (e.g., set the tension of the mesh). In addition, the apparatus (5) can allow access for piston-like driving of tack through mesh into fascia through a superior access port.

A tack delivery apparatus (4) can communicate with the mesh stretching apparatus (5). The apparatus (4) can include an electro-mechanically driven, piston-like apparatus and delivery chamber. On the opposite end of the handle (14), the system includes a functional end (3) used for interfacing with abdominal fascia. The system can be used to deliver a tack (2) into the mesh (7) and fascia.

Figure 22A:
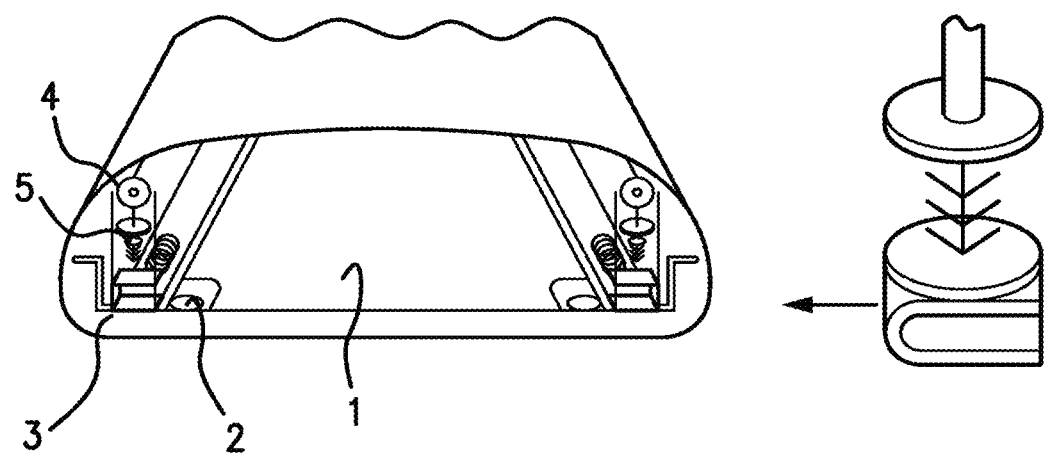
FIGS. 22A and 22B show device tension setting and affixation diagrams according to an embodiment of the disclosed subject matter.
Figure 22B:
Figure 22B:
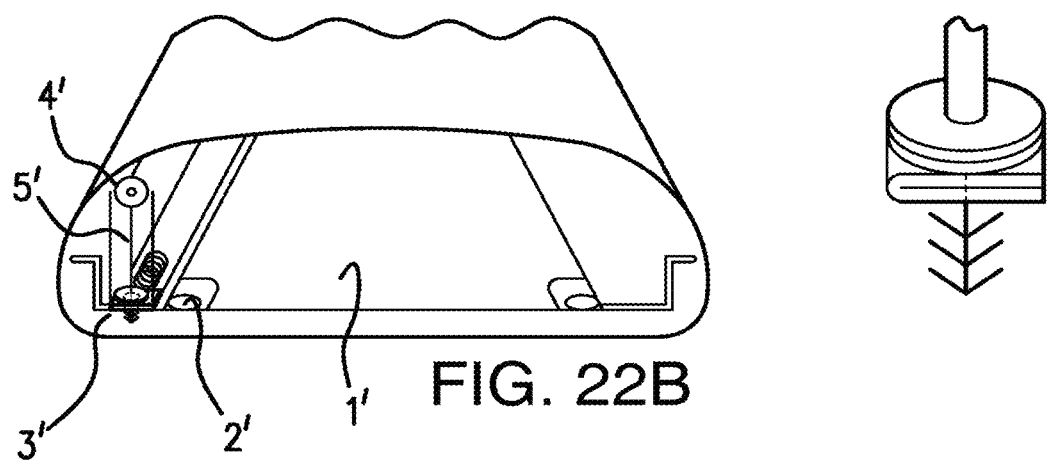

FIGS. 22A and 22B show device tension setting and affixation diagrams according to an embodiment of the disclosed subject matter. Regarding FIG. 22A, the mesh is shown within the device prior to tension setting (1). The tension setting apparatus (2) grasps the mesh with opening for tack delivery. The embodiment also includes a mechanical apparatus (3) to deliver tack through the mesh info fascia. A tack reservoir system (4) includes a preloaded spring mediated delivery system. The interface (5) for mechanical tack delivery is shown in neutral.

Regarding FIG. 22B, the mesh is shown in tension setting at affixation (1'). The tension setting apparatus (2') displaces the mesh and allows tack delivery. Activation of the mechanical apparatus (3') delivers tack into the mesh and fascia. The reservoir system (4') is shown pre-tack re-fill. The interface (5') for mechanical tack delivery is shown following activation.

Figure 23:
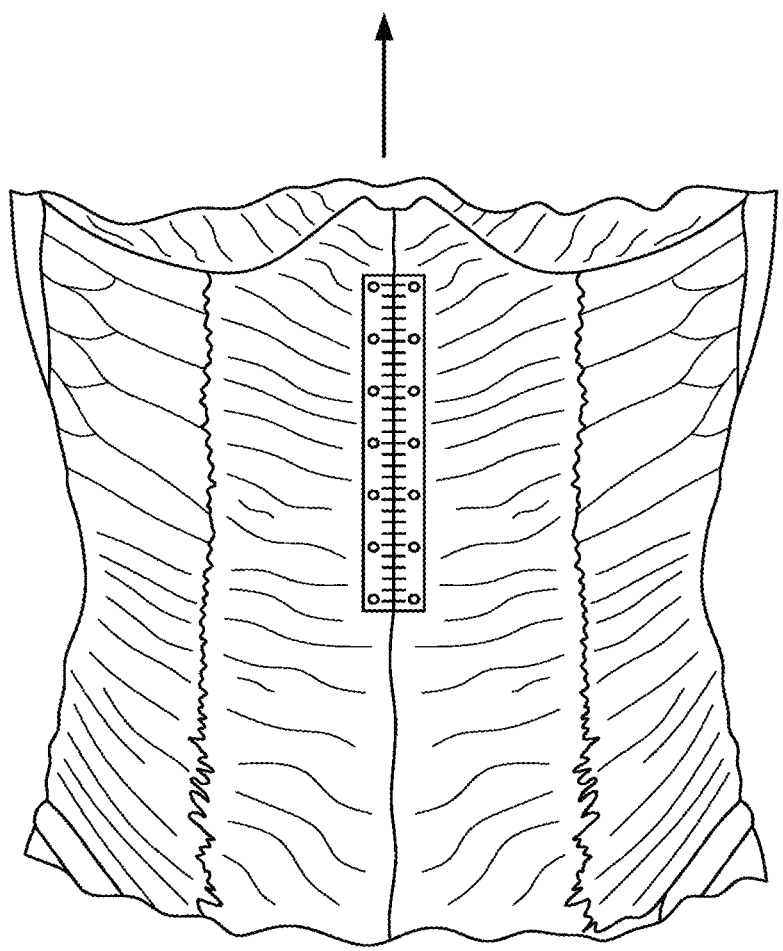
FIG. 23 shows a mesh augmented repair of the abdominal wall fascia and the relationship of the mesh to the rectus complex according to an embodiment of the disclosed subject matter.
Figure 23:
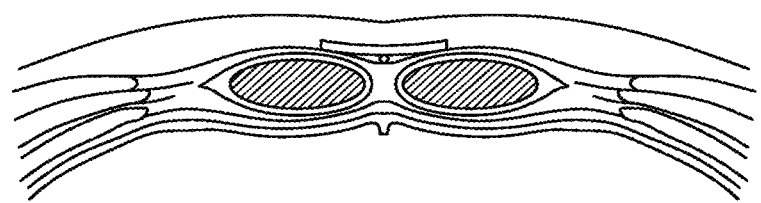

FIG. 23 is overview drawing of the abdominal wall and demonstrates a mesh augmented repair of the abdominal wall fascia and the relationship of the mesh to the rectus complex. The ultimate result of device mediate mesh augmentation is demonstrated in which a close fascial incision can be augmented with a tension-set, precisely applied mesh onlay in which the mesh can be affixed to the anterior fascia lateral to sure closure and in a precise low profile, wrinkle-free fashion.

Figure 29A:
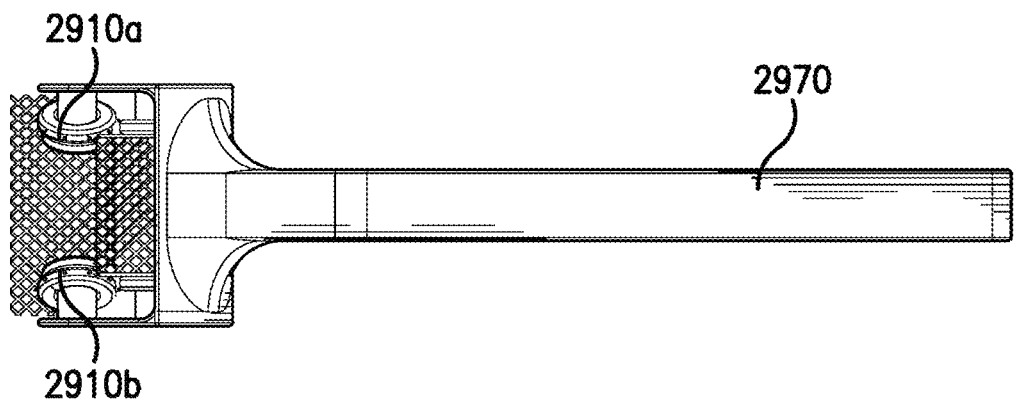
FIG. 29A is a top view of a mesh roller in accordance with an embodiment of the disclosed subject matter.
Figure 29B:
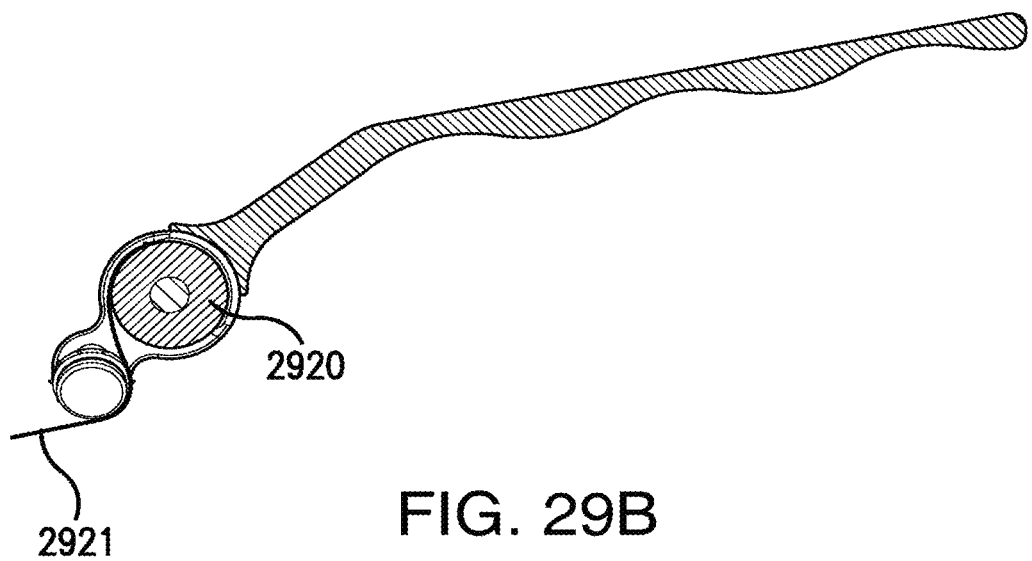
FIG. 29B is a side view of the mesh roller of FIG. 29A.
Figure 29C:
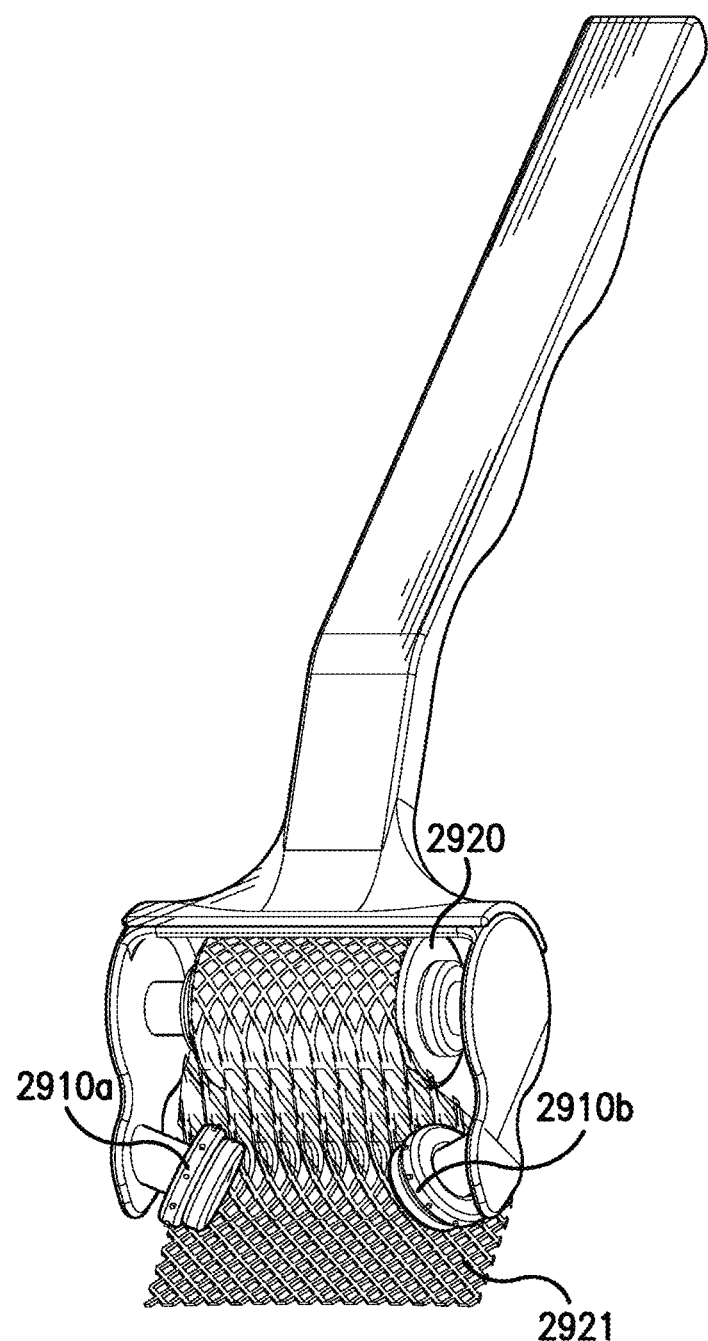
FIG. 29C is a perspective view of the mesh roller of FIG. 29A.

In accordance with another aspect of the disclosed subject matter, mesh can be delivered via an applicator system that functions as a mesh roller. For example, with reference to FIGS. 29A-29C, The mesh 2921 can be prepackaged in the distal portion of the applicator and pre-rolled (2920) such that with manual pressure and application the mesh can be rapidly placed onto the midline closure. Within the mesh following system can be a mechanical or electromechanical mesh tensioning function which also allows for faster integration. Additionally, the mesh can be applied with or without tension using glue or a glue reservoir. The mesh types can include self-adherent or nonadherent mesh types.

The roller can also include a handle 2970 for interoperative gripping. In certain embodiments, application of manual pressure onto the fascia can result in displacement of the mesh 2921, via roll mechanisms (2910a, 2910b), and tensioning of the mesh can occur such at the mesh is continually displaced with manual pressure and application. For example, rollers (2910a, 2910b) can be disposed at an angle such that the axis of rotation is offset from the plane of the mesh 2921. Additionally, the rollers (2910a, 2910b) can include barbs or protrusions about their radial edges. Upon application of pressure, the barbs can hook into loops of the mesh to provide tensioning. Additionally and/or alternatively, the mesh can be integrated with mini anchors to further allow for fixation.

As embodied herein, the mesh roller device can be a handheld operator controlled or automated roller device for application and deployment of surgical mesh of any length and type described herein to a surgical incision for the prevention of incisional hernia formation. The mesh can be anchored by any of the anchors described herein, a bead of medical adhesive of any type along the edges, medical tape affixed to the edges, total saturation with medical adhesive of any type including fibrin glue, cyanoacrylates, or the like, or any combination thereof. Embodiments of the applicator include designs for application of mesh by either forward (pushing) or backward (pulling) deployment. The applicator can include functional elements to accomplish the tasks associated with the primary function, including loading, tensioning, dispensing and deployment of the mesh, orientation and tissue engagement, loading and deployment of anchors, and cutting the mesh, examples of which are described herein.

Figure 35:
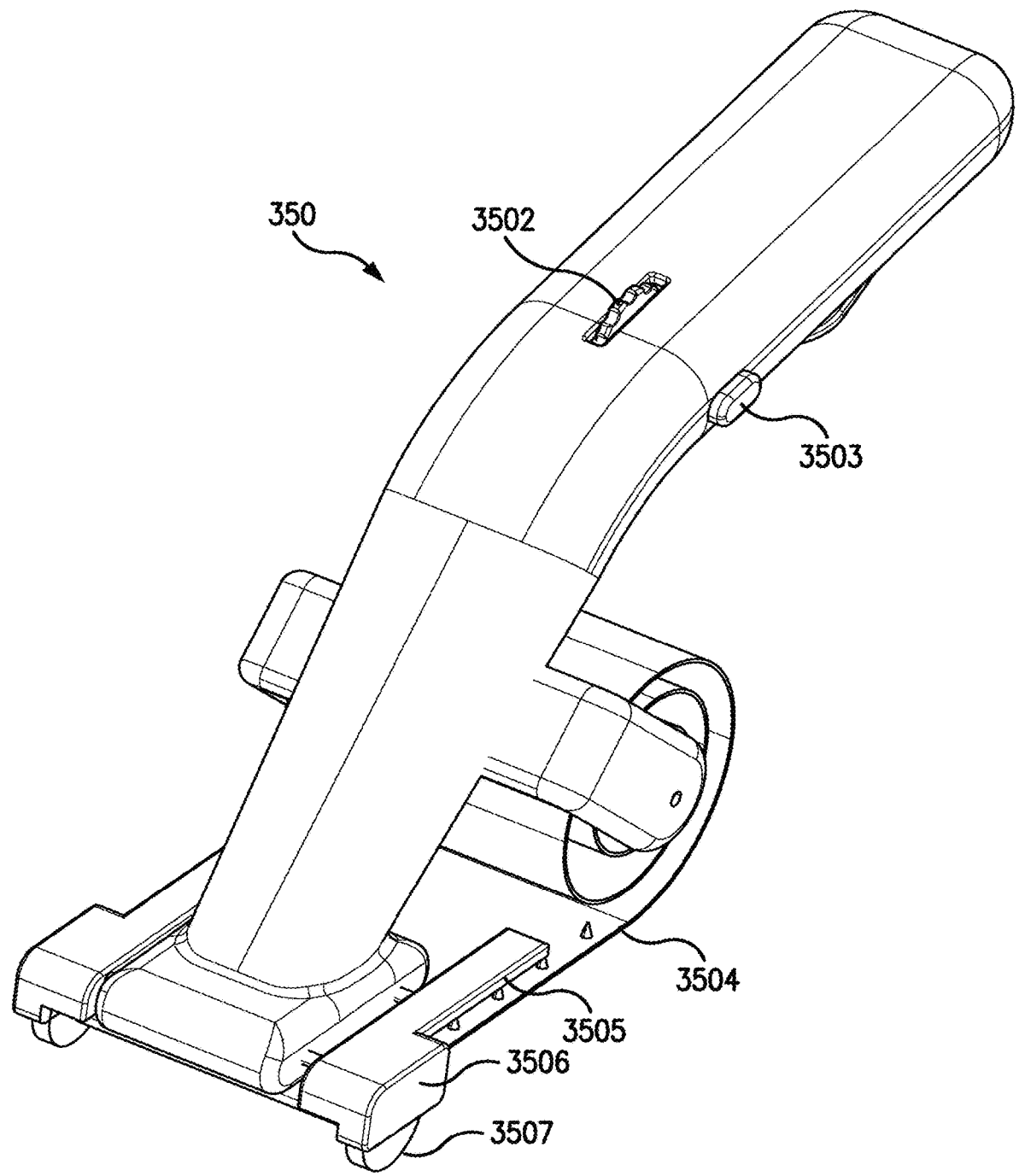
FIG. 35 is a perspective view of a mesh roller in accordance with an embodiment of the disclosed subject matter.

In connection with certain embodiments, and with reference to FIG. 35, a mesh roller can include an applicator handle for applying mesh with or without mechanical anchors integrated in the mesh. The mesh roller can include an ergonomic handle 3501 and can include a mechanism 3502 for manual adjustment of mesh advancement (e.g. electronic or mechanically). The roller can also include safety release 3503 (e.g thumb operated button) to allow actuation of other user feature for cutting (e.g. a separate button under the handle). In connection with this embodiment, hardware 3504 can be pre-loaded onto the mesh. A member 3505 on each side can provide tension to the mesh. The roller can also include a beading element 3506 incorporated near the point of application. It can also include a tube stored in a housing of the beading element 3506 which can be squeezed, metering adhesive, a reservoir of adhesive, and/or a tape roll that is applied to mesh. The roller can further include guidance 3507 (e.g. a wheel) that can additionally incorporate guiding/driving mesh advancement (e.g. a stepped shaft to capture the mesh as the wheel).

Figure 36:
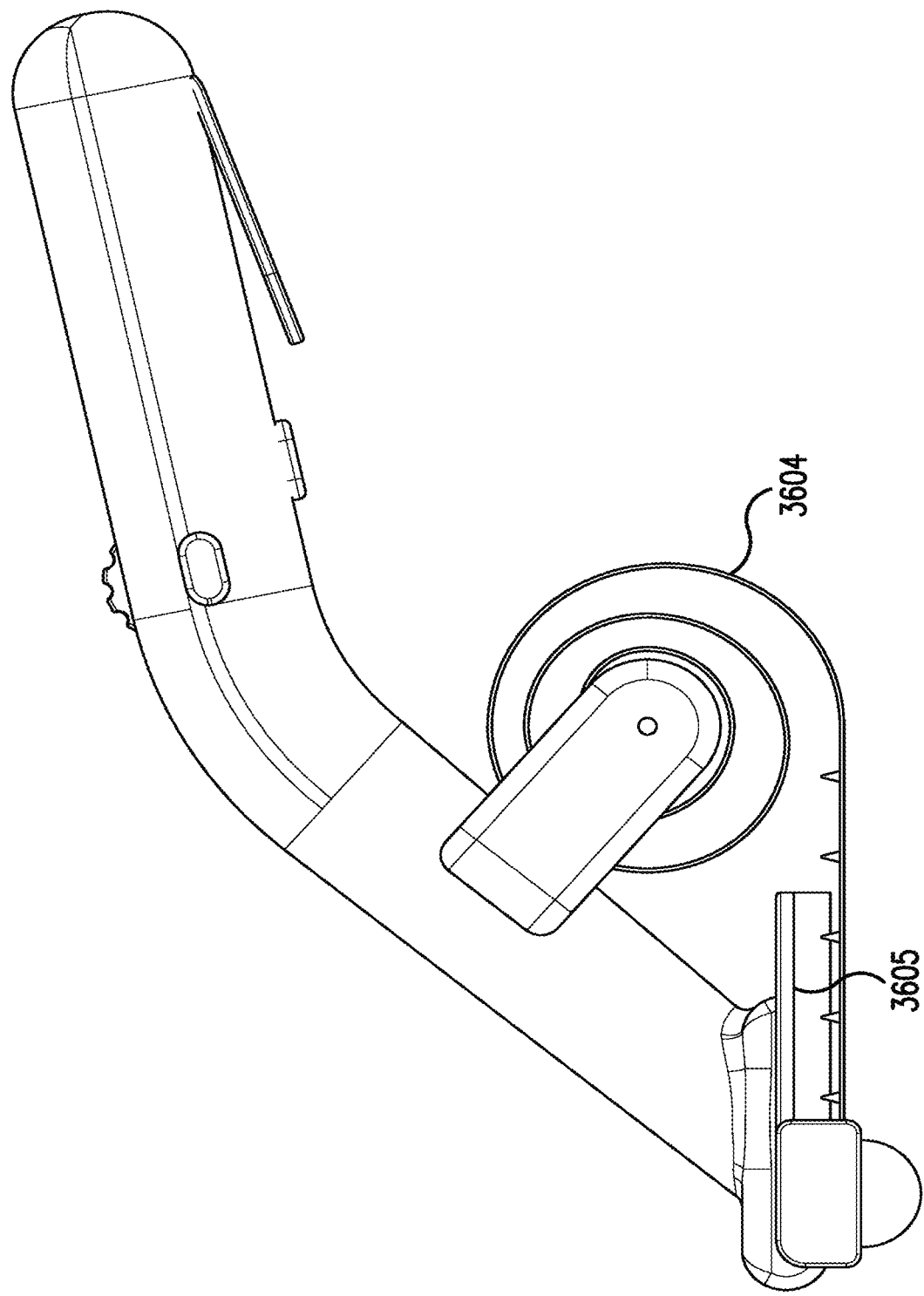
FIG. 36 is a side view of a mesh roller in accordance with an embodiment of the disclosed subject matter.
Figure 37A:
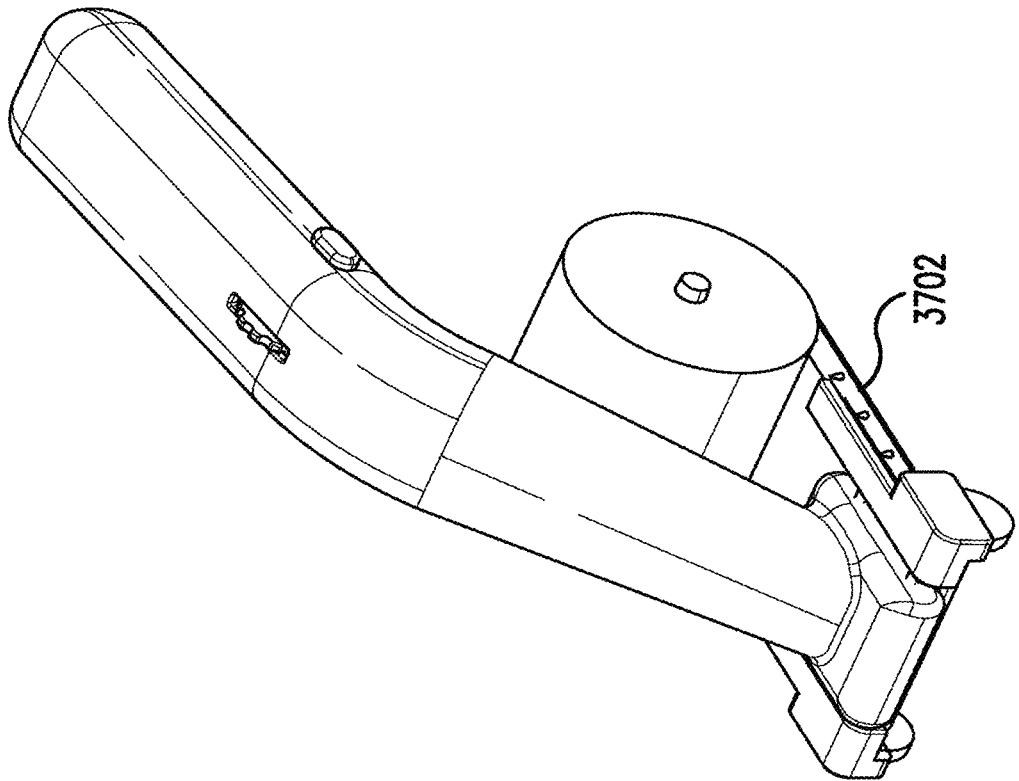
FIG. 37A illustrates a mesh assembly pre-loaded in an enclosure of a mesh roller in accordance with an embodiment of the disclosed subject matter.
Figure 37B:
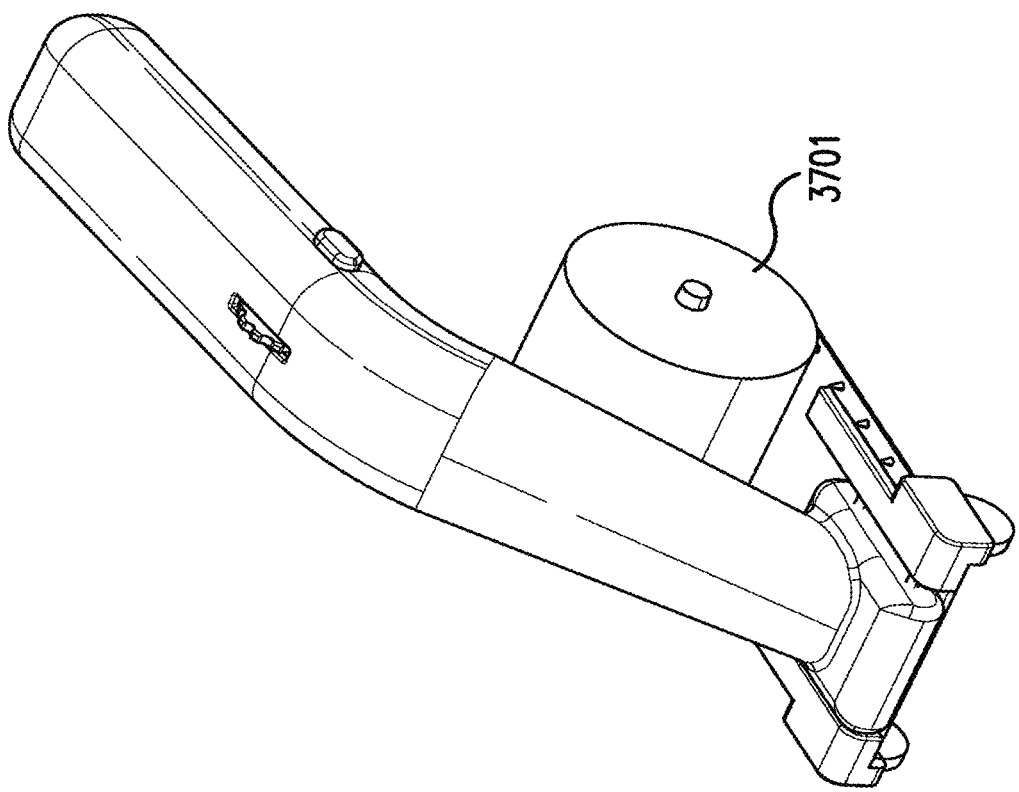
FIG. 37B illustrates a mesh assembly with adhesive pre-loaded in an enclosure of a mesh roller in accordance with an embodiment of the disclosed subject matter.

With reference to FIG. 36, in connection with certain embodiments, the hardware can be pre-loaded onto the mesh (3604). A member 3605 on each side can provide tension to the mesh. Additionally, the roller can include a mechanism 3606 for the user to apply tension to the mesh. For example, and not limitation, a lever 3606 can be squeezed as part of holding the handle, which in turn pushes out the members 3605, tensioning the mesh. Further, in connection with certain embodiments and with reference to FIG. 37A, the hardware and/or mesh assembly can be pre-loaded in an enclosure 3701 to facilitate easy loading/swapping of a new or different roll. For example, the roller can include a canister with an exit orifice for the mesh assembly. Additionally or alternatively, with reference to FIG. 37B, the mesh assembly can optionally be pre-loaded with mechanical anchors or adhesive in the enclosure. For example, as illustrated by FIG. 37B, the mesh assembly can include an adhesive or tape 3702 applied to the edge.

Figure 39:
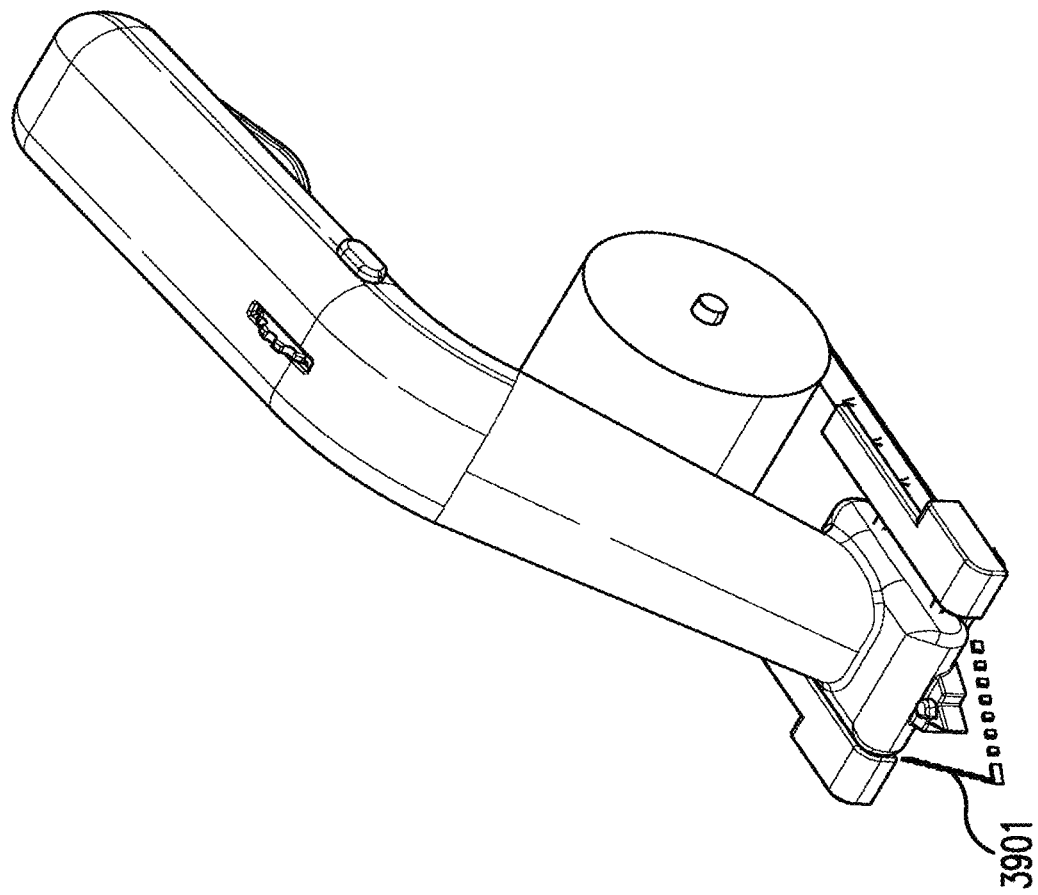
FIG. 39 illustrates a mesh roller with a tissue spreader in accordance with an embodiment of the disclosed subject matter.
Figure 38:
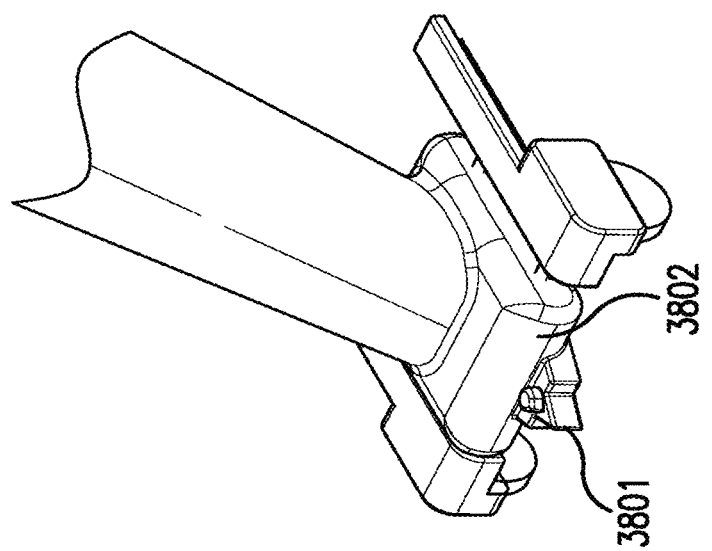
FIG. 38 illustrates a mesh roller with a feature to register the center of the mesh and a feature to adjust the angle of the cutter device in accordance with an embodiment of the disclosed subject matter.

With reference to FIG. 38, and in connection with certain embodiments, the mesh roller can include a feature to register the center of the mesh with the incision 3801. For example, and not limitation, the roller can include an indicator arrow or a see-through window to the center of the mesh. Additionally or alternatively, the roller can include a feature 3802 to adjust the angle of the cutter device when the incision changes path. For example, the feature 3802 can be configured to change the angle of the cutter device to partially cut the mesh to allow an angular shift in the applicator. Additionally, in connection with certain embodiments and with reference to FIG. 39, the mesh roller can also include a tissue spreader to provide clear tissue margins for mesh deployment. For example, and not limitation, mesh roller can include a tissue spreader 3901 integrated with a front portion of the roller. As embodied herein, the tissue spreader can be any of the types described herein.

Figure 40:
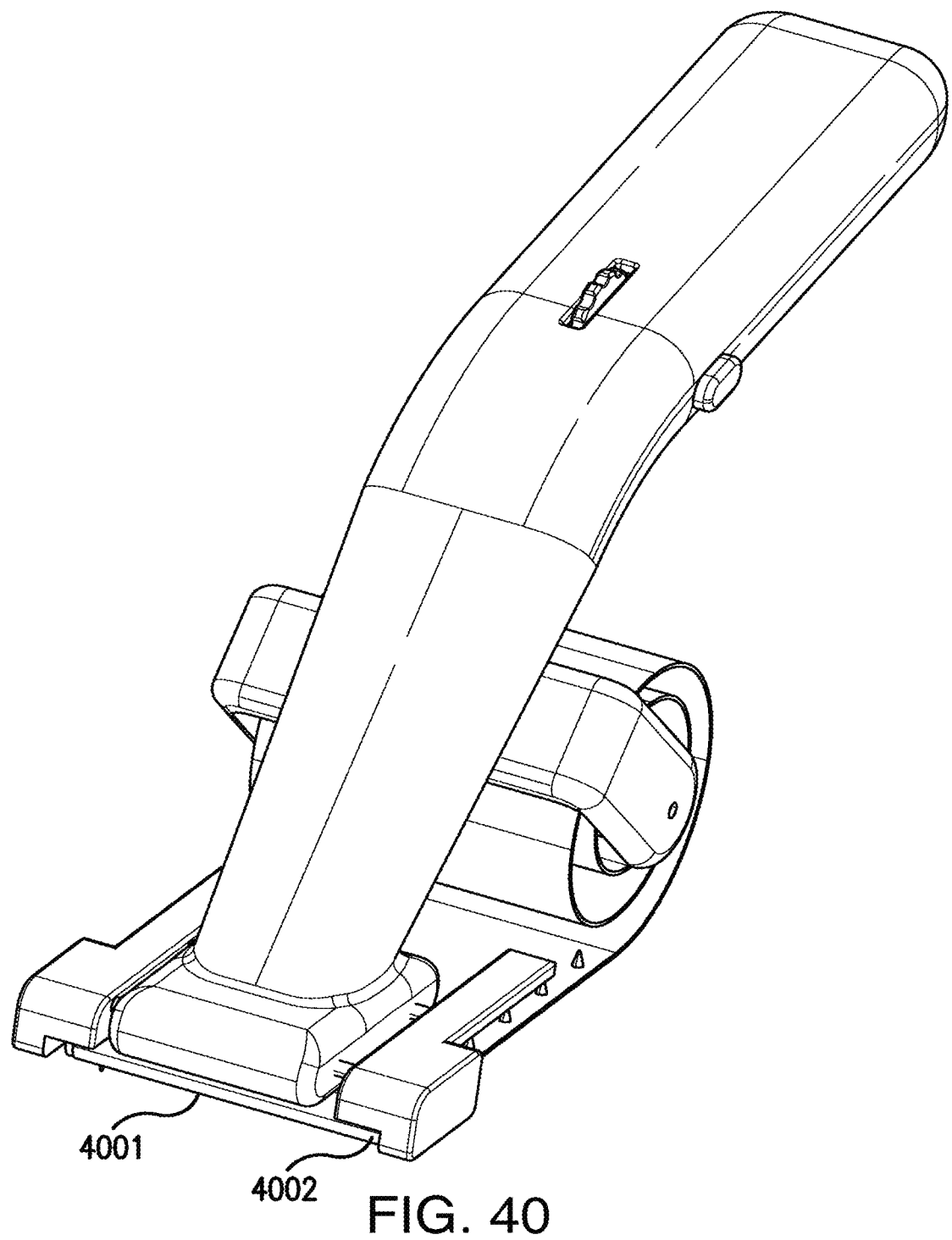
FIG. 40 illustrates a mesh roller with a platen in accordance with an embodiment of the disclosed subject matter.

In connection with certain embodiments, with reference to FIG. 40, a mesh roller in accordance with the disclosed subject matter can include a feature 4001 adapted such that the mesh travels over feature 4001 so that the mesh is the only item in direct contact with tissue. For example, and not limitation, feature 4001 can be a platen or a roller across the front of the device. Depressing the platen 4001 with pressure against tissue can activate the adhesive application 4001 at the same time as the mesh application.

Figure 41B:
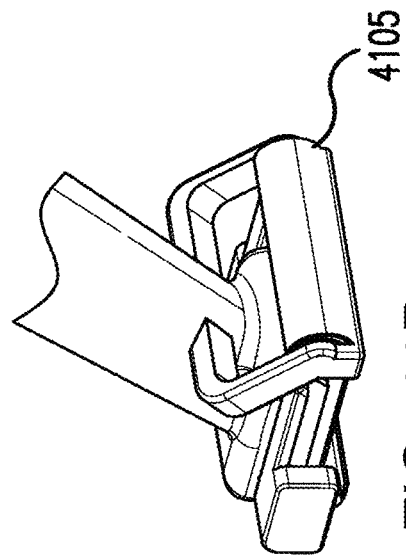
FIG. 41B is a back perspective view of the mesh roller of FIG. 41A.
Figure 41C:
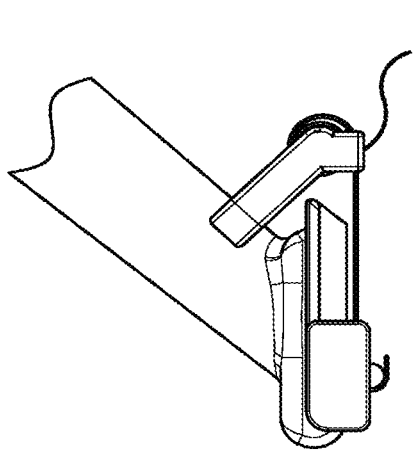
FIG. 41C is a side view of the mesh roller of FIG. 41A.
Figure 41A:
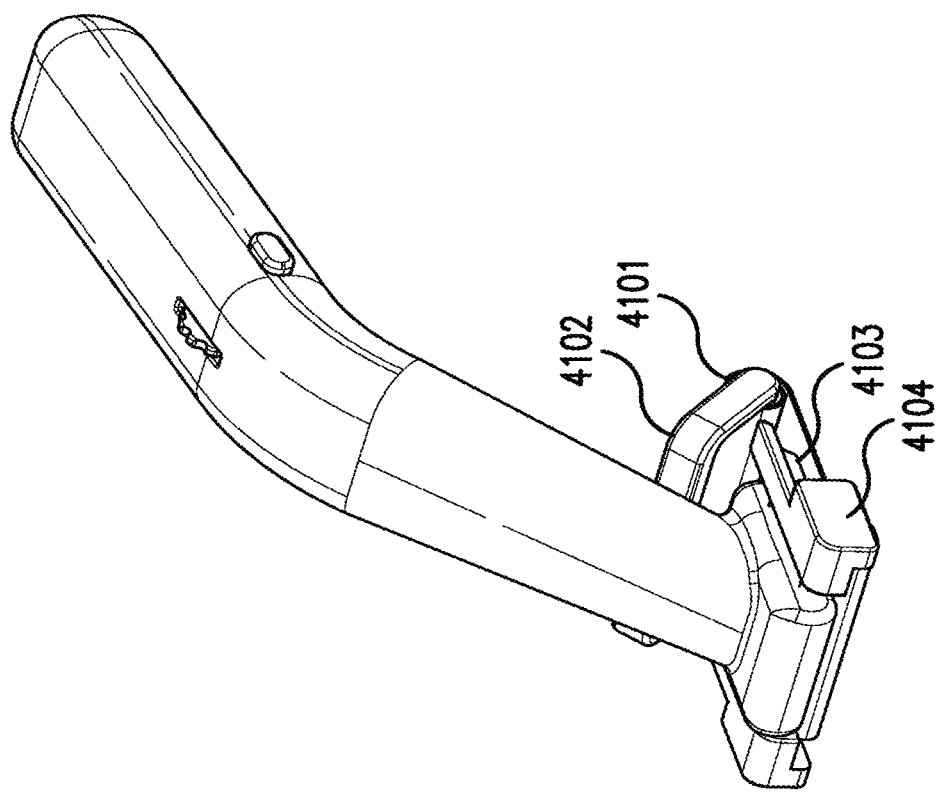
FIG. 41A illustrates a mesh roller with an adhesive applicator in accordance with an embodiment of the disclosed subject matter.

FIGS. 41A-41C depict another embodiment of a mesh roller in accordance with the disclosed subject matter. In connection with this embodiment, the roller can include a roll of mesh on a carrier 4101 (e.g. refillable or pre-loaded on the device). The roller can also include a carrier arm 4102 to hold the mesh, and can apply longitudinal tension as needed. Tension members 4103 can provide lateral tension to the mesh. The tension members 4103 can interface to mesh in a variety ways. For example, and not limitation, tension members 4103 can interface with the mesh using an indexing wheel in arm, pins that protrude into the mesh, or clamping of the mesh between two different elements of the arm. The roller of this embodiment can also include an adhesive beading element 4104, such as the adhesive beading element described with reference to the embodiment depicted in FIG. 35, to apply edge bead. Alternately, adhesive tape can be pre-applied to the mesh. FIG. 41A depicts a perspective view of a mesh roller in accordance with this embodiment; FIG. 41B depicts a back perspective view illustrating an adhesive applicator at the mesh roller 4105. For example, the adhesive applicator can include a tray 4106 as depicted in FIG. 41C. Alternatively, the adhesive applicator can include a canister as described herein with reference to other embodiments.

Figure 42B:
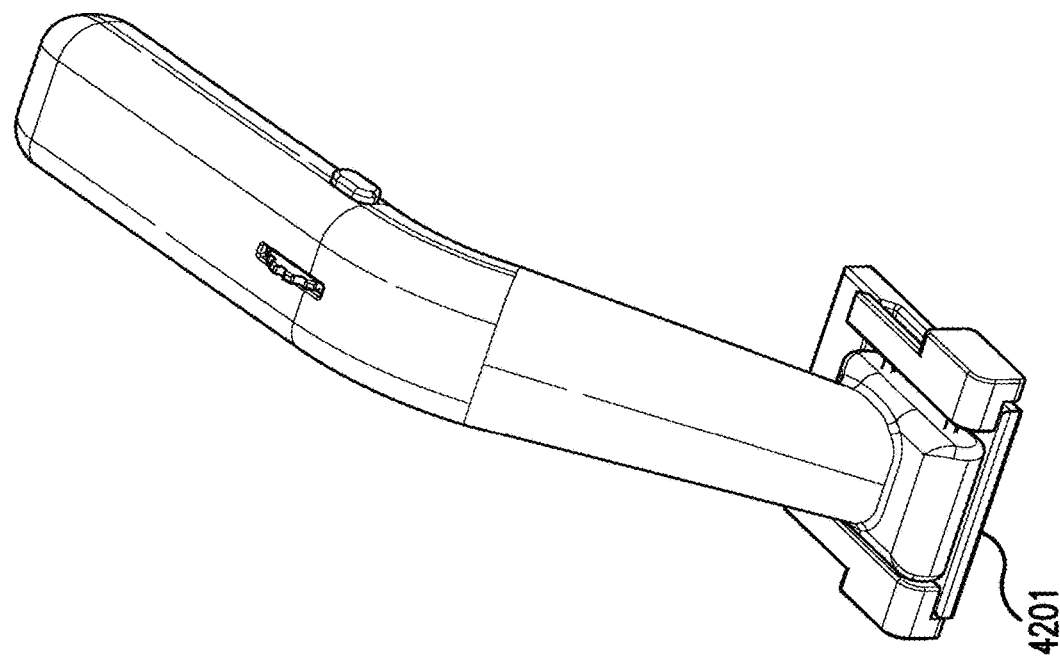
FIGS. 42A and 42B illustrate a mesh roller with a cartridge in accordance with an embodiment of the disclosed subject matter.
Figure 42A:
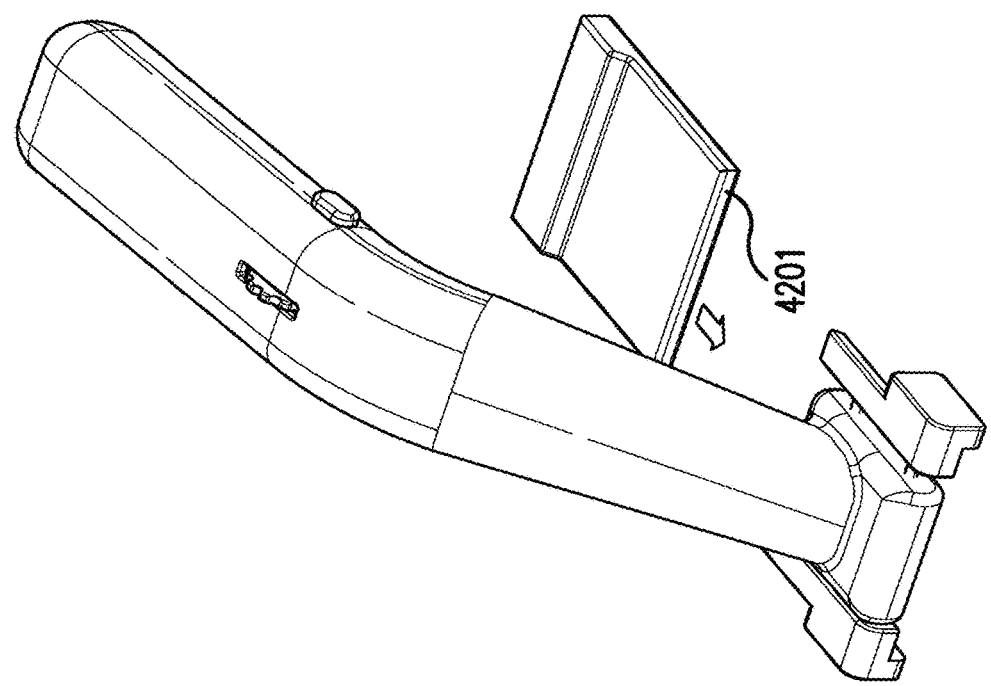

In connection with certain embodiments of the disclosed subject matter, and with reference to FIGS. 42A and 42B, the mesh roller can be adapted to apply shorter lengths of mesh. For example, and not limitation, the roller can include a cartridge 4201 which is adapted to store shorter lengths of mesh instead of a spool as described above. The cartridge 4201 as described herein can be used with any of the fasteners or adhesives described herein.

Figure 43:
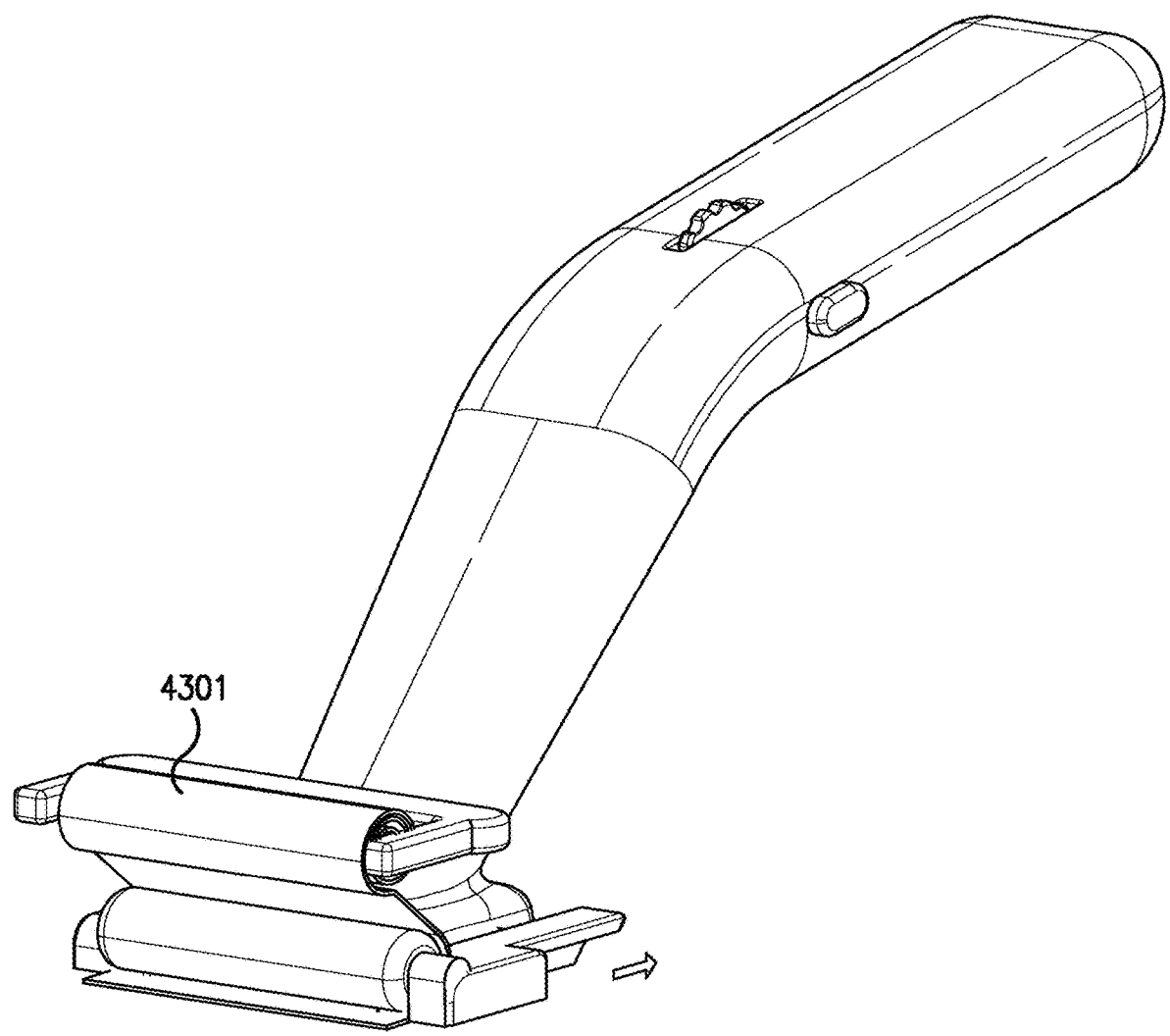
FIG. 43 illustrates a mesh roller in accordance with another embodiment of the disclosed subject matter.

In connection with certain embodiments, and with reference to FIG. 43, a mesh roller can be configured so that a user may pull the roller to apply the mesh instead of pushing. For example, the mesh can be loaded on a spool 4301 located at the front of the device, such that when a user applies pressure and pulls the device in a rearward direction the mesh is applied. One of skill in the art will appreciate that all of the features described above can also be included in this embodiment.

Figure 44:
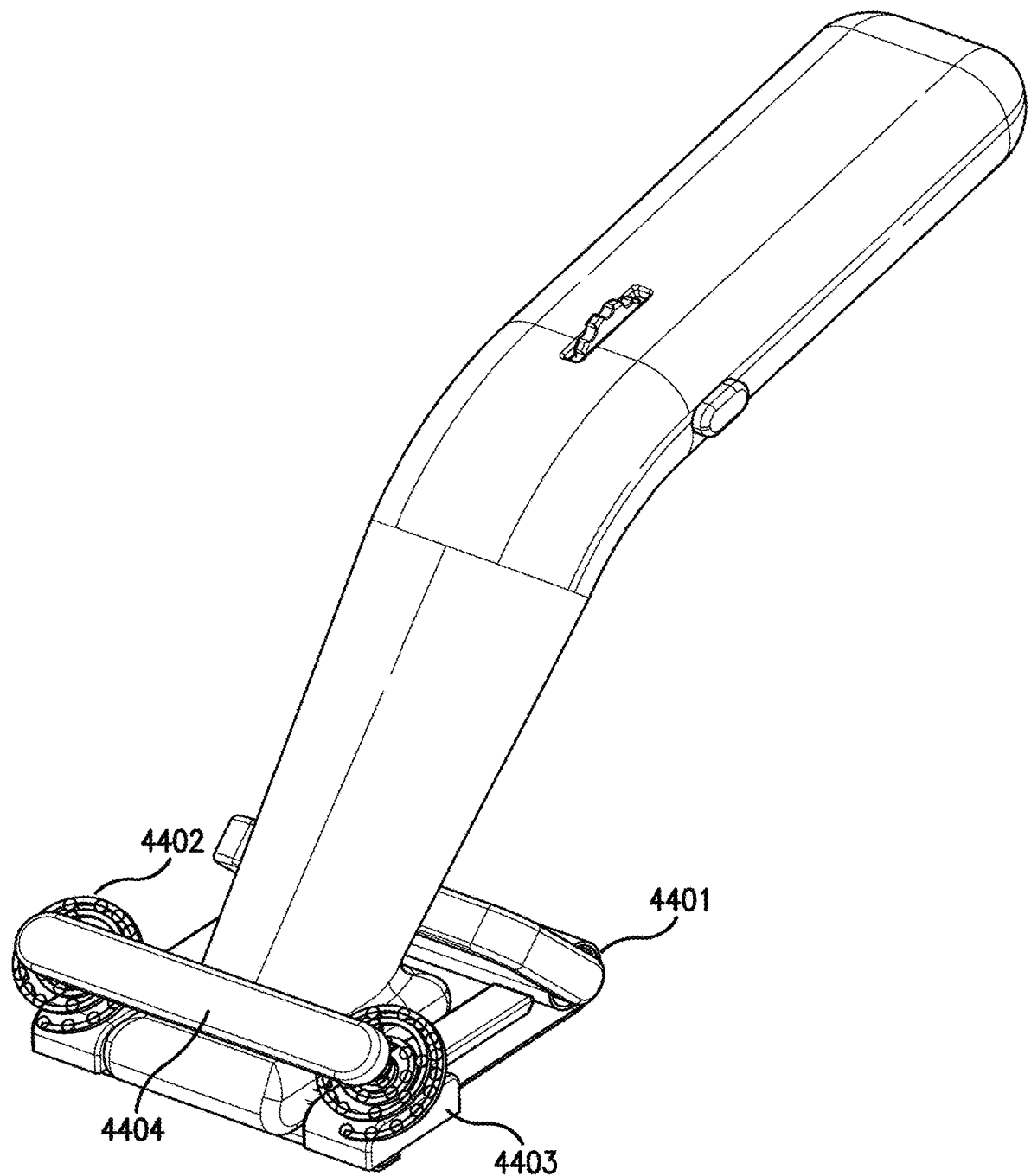
FIG. 44 illustrates a mesh roller configured to load mechanical anchors in accordance with an embodiment of the disclosed subject matter.

FIG. 44 depicts an embodiment of a mesh roller in accordance with the disclosed subject matter where mechanical anchors are loaded into the mesh as part of operation. The roller can include mesh pre-loaded 4401 as previously described. In connection with this embodiment, the hardware 4402 can be loaded separately. For example, and not limitation, the hardware can be loaded on a roll 4402 as depicted in the figure. Additionally or alternatively, the hardware can be loaded in a linear fashion, or in a bundled arrangement where components can be broken off and/or separated prior to attachment. The roller can also have a feature 4403 that can align and feed the fastener down into the mesh. Additionally, the roller can include a mounting member 4404 for the hardware which can allow for easy reloading.

Figure 45B:
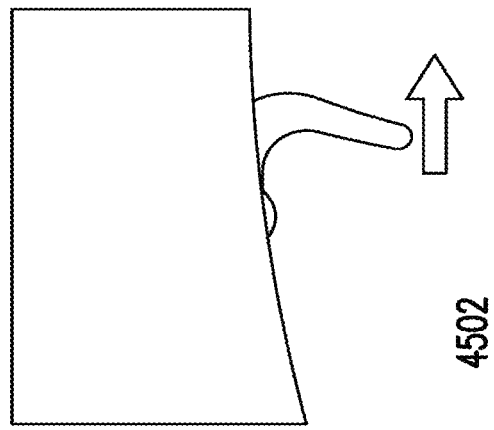
FIGS. 45A and 45B illustrate a two stages trigger for use in a mesh roller in accordance with an embodiment of the disclosed subject matter.
Figure 45A:
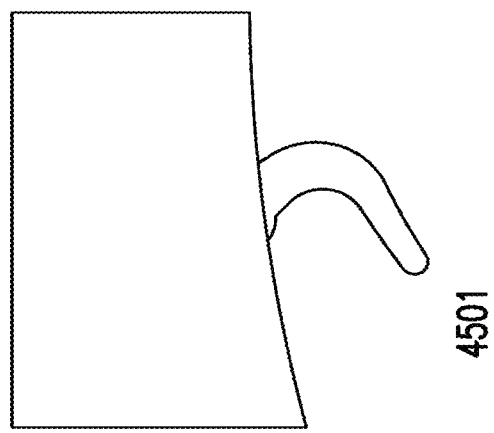

As embodied herein, mesh rollers can include a mechanism to unlock the system and initiate deployment and a mechanism to cut the mesh after it has been applied. For example, various embodiments of the mesh roller can include a two stage trigger mechanism. With reference to FIGS. 45A and 45B, the trigger can be pulled to rotate up to unlock the system and initiate deployment (4501). Pulling on the trigger through the second stage can result in a second operation 4502, such as cutting of the mesh.

Example

To apply the mesh, custom-printed extension arms were created to attach onto an existing surgical tissue spreading device (9-inch Weitlaner) (FIGS. 2A-2C). The tension-applicator arms 210*a* 210*b* were fabricated from an acrylonitrile butadiene styrene (ABS) material using the Fused Deposition Modeling (FDM) process. These arms are responsible for interfacing with the fasteners posts to allow incremental tensioning of the mesh. The tensioned mesh strip can then be affixed under tension to anterior abdominal wall fascia. The mesh spreads evenly using this system, and can be assembled, tensioned, and applied in 120±40 seconds (5 applications). The mesh-anchors achieve adequate tissue penetration through the fascia to permit fixation based on initial pilot testing of the device (approximately 3.5 mm of fascia penetration).

Figure 3:
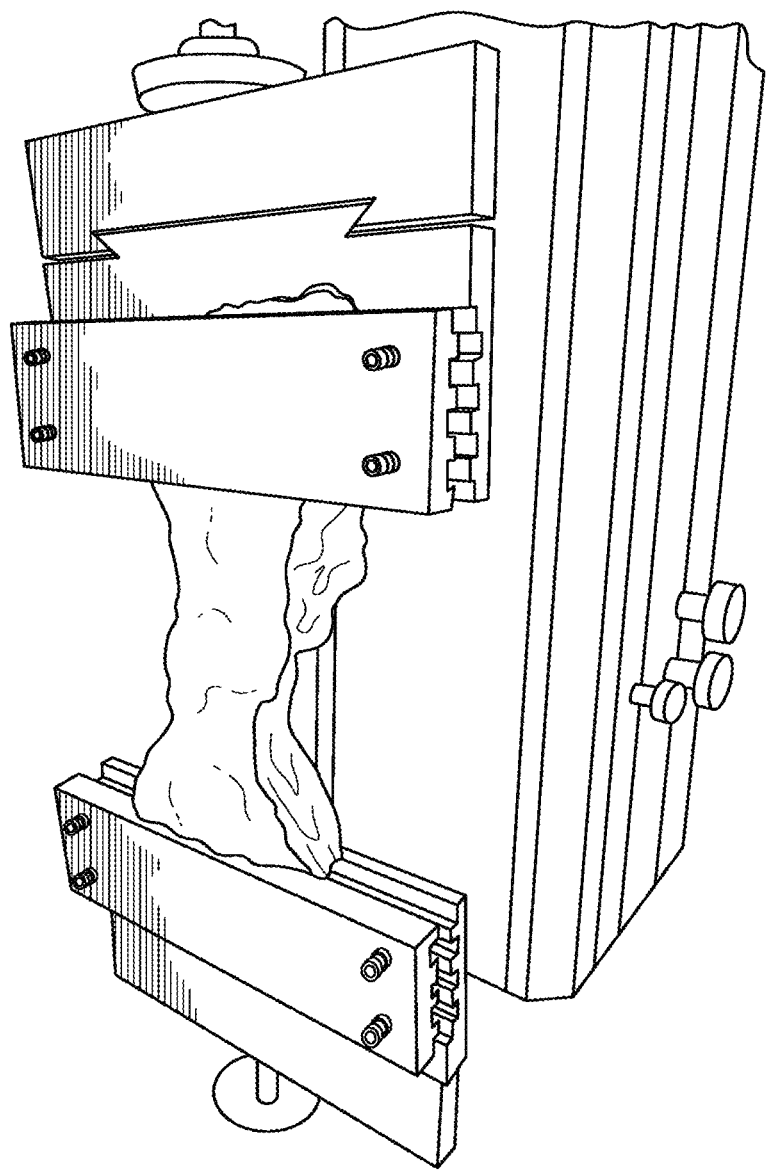
FIG. 3 illustrates a demonstration of milled, aluminum clamps and mesh augmented porcine specimen tested within the Instron 5543 Electromechanical Testing Machine performing uni-axial tension assessment in accordance with the disclosed subject matter.

To prepare for biomechanical testing of cadaveric tissue samples using the Instron 5543 Electromechanical Testing Machine, a pair of customized large clamps were machined from Aluminum 6061-T6 (FIG. 3). The clamps are composed of three pieces, the male block, the male faceplate, and the female block. The two pieces are tightened around the test specimen by screwing in 6-32 screws. To test the clamps and to assess the relative strength of a mesh augmented closure, uni-axial tension testing was performed, demonstrating 75 N at failure.

The presently disclosed subject matter is not to be limited in scope by the specific embodiments herein. Indeed, various modifications of the disclosed subject matter in addition to those described herein will become apparent to those skilled in the art from the foregoing description and the accompanying figures. Such modifications are intended to fall within the scope of the appended claims.

The invention claimed is:

1. A method for positioning and onlay affixation of a pretensioned reinforcing material to abdominal wall fascia to reinforce and augment a fascial incision closure, comprising:
   aligning the reinforcing material over the fascial incision using an applicator;
   tensioning the reinforcing material by using the applicator to increase a distance between opposing sides of the reinforcing material from a first distance to a second distance, wherein the tensioned reinforcing material is in a planar condition when the opposing sides are at the second distance; and
   mechanically anchoring the reinforcing material under tension to an anterior abdominal wall fascia.

2. The method of claim 1, wherein the reinforcing material is mechanically anchored over a primary repair of the fascial incision such that the reinforcing material decreases a tension across the primary repair.

3. The method of claim 2, wherein mechanically anchoring the tensioned reinforcing material unloads the primary repair.

4. The method of claim 2, wherein the primary repair comprises sutures.

5. The method of claim 1, wherein the reinforcing material is affixed to the facial incision after incisional access to the abdomen during an index abdominal surgical procedure.

6. The method of claim 1, wherein the second distance is between 1 to 10 mm larger than the first distance.

7. The method of claim 1, wherein the reinforcing material comprises one or more of a permanent synthetic material, a biologic material, a bio-absorbable material, and combinations thereof.

8. The method of claim 1, wherein the reinforcing material includes a mesh.

9. The method of claim 1, wherein a plurality of fasteners are arranged on opposing sides of the reinforcing material to form one or more opposing fastener pairs, each fastener including at least one anchoring mechanism adapted for affixation to anterior abdominal wall fascia and a mating interface; and
   wherein tensioning the reinforcing material includes engaging the applicator with the mating interfaces of the fasteners and increasing a distance between fasteners in one or more opposing fastener pairs from the first distance to the second distance, wherein the applicator applies a force on the fastener mating interfaces that is transduced into the reinforcing material by one or more opposing fastener pairs; and
   wherein mechanically anchoring the tensioned reinforcing material includes applying a force to the fasteners to thereby achieve tissue penetration of the anchoring mechanisms of the one or more opposing fastener pairs.

10. The method of claim 9, wherein the reinforcing material is rectangular and includes a fastener proximate each corner forming two opposing fastener pairs.

11. The method of claim 9, wherein the anchoring mechanism of each fastener comprises a barbed affixation with a barb adapted for a predetermined amount of fascia penetration.

12. The method of claim 9, wherein the mating interfaces include one or more of: a post, a knob, a snap, or a structural element having a hole therein adapted to engage with the applicator.

13. The method of claim 9, wherein the plurality of fasteners are integrated with the reinforcing material.

14. The method of claim 1, wherein mechanically anchoring the tensioned reinforcing material includes applying one or more of a biologic or biomedical adhesive or glue.

15. The method of claim 1, wherein the applicator further comprises a tensiometer configured to measure and display a horizontal tension of the reinforcing material.

16. The method of claim 15, wherein the applicator has an omega shape, wherein the handle of the applicator comprises the spring.

17. The method of claim 1, wherein the applicator further comprises a spring to facilitate out of plane affixation of the reinforcing material to the fascia.

18. The method of claim 1, wherein the applicator includes an electromechanical actuator to affix fasteners and the reinforcing material to the fascia.

19. The method of claim 1, wherein the applicator includes a reservoir for storing the reinforcing material and affixing the reinforcing material includes displacing the reinforcing material from the reservoir.

20. The method of claim 19, further comprising at least one of cutting the reinforcing material and terminating the reinforcing material.

21. A method for positioning and onlay affixation of a pretensioned reinforcing material to abdominal wall fascia to reinforce and augment a fascial incision closure, comprising:
   aligning the reinforcing material at an anterior surface of the abdominal wall fascia over the fascial incision using an applicator;
   tensioning the reinforcing material, using the applicator to increase a distance between opposing sides of the reinforcing material from a first distance to a second distance; and
   mechanically anchoring the reinforcing material under tension to the anterior surface of the abdominal wall fascia.

* * * * *